(12) United States Patent
Wang et al.

(10) Patent No.: US 11,771,759 B2
(45) Date of Patent: Oct. 3, 2023

(54) IMMUNOPOTENTIATOR, IMMUNOTHERAPEUTIC PHARMACEUTICAL COMPOSITION AND ITS PREPARATION AND USE

(71) Applicant: FUDAN UNIVERSITY, Shanghai (CN)

(72) Inventors: Bin Wang, Shanghai (CN); Weidong Zhao, Shanghai (CN); Gan Zhao, Shanghai (CN); Yiwei Zhong, Shanghai (CN)

(73) Assignee: Fudan University, Shanghai (CN)

( * ) Notice: Subject to any disclaimer, the term of this patent is extended or adjusted under 35 U.S.C. 154(b) by 699 days.

(21) Appl. No.: 16/491,550

(22) PCT Filed: Jan. 24, 2018

(86) PCT No.: PCT/CN2018/073916
§ 371 (c)(1),
(2) Date: Sep. 5, 2019

(87) PCT Pub. No.: WO2018/166298
PCT Pub. Date: Sep. 20, 2018

(65) Prior Publication Data
US 2022/0175912 A1   Jun. 9, 2022

(30) Foreign Application Priority Data

Mar. 13, 2017 (CN) .......................... 201710021679.6
Jan. 15, 2018 (CN) .......................... 201810035029.1

(51) Int. Cl.
*A61K 39/29* (2006.01)
*A61P 35/00* (2006.01)
*A61K 39/00* (2006.01)
*A61K 39/09* (2006.01)
*A61K 39/39* (2006.01)
*C12N 7/00* (2006.01)
*C07K 14/52* (2006.01)
*C07K 14/535* (2006.01)
*C07K 14/565* (2006.01)

(52) U.S. Cl.
CPC ...... *A61K 39/29* (2013.01); *A61K 39/001157* (2018.08); *A61K 39/001186* (2018.08); *A61K 39/001193* (2018.08); *A61K 39/092* (2013.01); *A61K 39/39* (2013.01); *A61P 35/00* (2018.01); *C07K 14/52* (2013.01); *C07K 14/535* (2013.01); *C07K 14/565* (2013.01); *C12N 7/00* (2013.01); *A61K 2039/545* (2013.01); *A61K 2039/55522* (2013.01); *A61K 2039/804* (2018.08); *A61K 2039/812* (2018.08); *A61K 2039/868* (2018.08); *A61K 2039/884* (2018.08); *A61K 2039/892* (2018.08); *C12N 2730/10011* (2013.01); *C12N 2730/10034* (2013.01); *C12N 2730/10134* (2013.01)

(58) Field of Classification Search
CPC ............ A61K 39/29; A61K 39/001157; A61K 39/001186; A61K 39/001193; A61K 39/092; A61K 39/39; A61K 2039/545; A61K 2039/55522; A61K 2039/804; A61K 2039/812; A61K 2039/868; A61K 2039/884; A61K 2039/892; A61K 2039/5256; A61K 2039/55505; A61K 2039/6081; A61K 39/001153; A61K 39/001156; A61K 39/001182; A61K 39/12; A61K 2039/82; A61K 2039/836; A61K 2039/844; A61K 2039/55516; A61K 39/0011; A61K 39/21; A61K 39/292; A61K 2039/541; A61K 2039/80; A61P 35/00; A61P 31/00; A61P 31/18; A61P 31/20; A61P 1/16; C07K 14/52; C07K 14/535; C07K 14/565; C07K 14/005; C12N 7/00; C12N 2730/10011; C12N 2730/10034; C12N 2730/10134; C12N 15/86; C12N 2710/20034; C12N 2740/16034; C12N 2750/14143
See application file for complete search history.

(56) References Cited

U.S. PATENT DOCUMENTS

2016/0136265 A1* 5/2016 Wang .................... A61K 47/60
424/85.1

FOREIGN PATENT DOCUMENTS

CN   104338132 A  *  2/2015  .......... A61K 31/513
EP   3025730       6/2016

OTHER PUBLICATIONS

Li S, Luo S, Lei Q, Meng Z. Hepatitis B Surface Antigen Seroconversion by Interferon-α2b Combined with Granulocyte-Macrophage Colony-Stimulating Factor and Hepatitis B Vaccine: A Case Report. Viral Immunol. Mar. 2020;33(2):122-125. doi: 10.1089/vim.2019. 0119. Epub Dec. 26, 2019. (Year: 2019).*

(Continued)

*Primary Examiner* — Rachel B Gill
(74) *Attorney, Agent, or Firm* — K&L Gates LLP

(57) ABSTRACT

An immune enhancer comprising at least an interferon and a granulocyte-macrophage colony-stimulating factor, and an immunotherapeutic phar-maceutical composition comprising at least an antigen and the above-mentioned immune enhancers is disclosed. A preparation method of the immunotherapeutic pharmaceutical composition, the use of the immune enhancer and the immunotherapeutic pharmaceutical composition are also disclosed. The immune enhancer can be applied to disease and tumor treatments caused by viruses, bacteria, and other microorganisms.

25 Claims, 20 Drawing Sheets
Specification includes a Sequence Listing.

(56) References Cited

OTHER PUBLICATIONS

Van Thiel DH, Friedlander L, Kania RJ, Molloy PJ, Hassanein T, Faruki H. A preliminary experience with GM-CSF plus interferon in patients with HBV and HCV resistant to interferon therapy. J Viral Hepat. 1997;4 Suppl 1:101-6. (Year: 1997).*

Tilg H, Vogel W, Tratkiewicz J, Aulitzky WE, Herold M, Gruber M, Geissler D, Umlauft F, Judmaier G, Schwulera U, et al. Pilot study of natural human interleukin-2 in patients with chronic hepatitis B. Immunomodulatory and antiviral effects. J Hepatol. Sep. 1993;19(2):259-67. (Year: 1993).*

Zhao W, Zhao G, Zhang S, Wang X, Yu X, Wang B. Clearance of HBeAg and HBsAg of HBV in mice model by a recombinant HBV vaccine combined with GM-CSF and IFN-α as an effective therapeutic vaccine adjuvant. Oncotarget. Jul. 13, 2018;9(76):34213-34228. (Year: 2018).*

"Leukine (Sargramostim)". RxList.com. Cunha JP, ed., accessed Aug. 17, 2022, last updated May 12, 2022. (Year: 2022).*

Pilla L, Patuzzo R, Rivoltini L, Maio M, et al. A phase II trial of vaccination with autologous, tumor-derived heat-shock protein peptide complexes Gp96, in combination with GM-CSF and interferon-alpha in metastatic melanoma patients. Cancer Immunol Immunother. Aug. 2006;55(8):958-68. Epub Oct. 8, 2005. (Year: 2005).*

European Search Report for App. No. 18768314.9 dated Dec. 23, 2020 (10 pages).

Lorenzo Pilla et al: "A phase II trial of vaccination with autologus, tumor-derived heat-shock protein peptide complexes Gp96, in combination with GM-CSF and intereron-[alpha] in metastatic melanoma patients",Cancer Immulonogy, Immunotherapy, Springer, Berlin, DE, vol. 55. no. 8, Aug. 1, 2006, pp. 958-968.

Carreno V. et al., "randomized controlled trial of recombinant human granulocyte-macrophage colony-stimulating factor for the treatment of chronic hepatitis c", Cytokine, Academic Press Ltd., Philadelphia, PA, US, vol. 12, No. 2, Feb. 1, 2000, pp. 165-170.

Duggan, Megan C. et al., "A phase I study of recombinant (r) vaccinia-CEA (6D)-TRICOM and rFowlpox-CEA(6D)-TRICOM vaccines with GM-CSF and IFN-[alpha]-2b in patients with CEA-expressing carinomas", Cancer Immunology, Immunotherapy, Springer, Berlin/Heidelberg, vol. 65, No. 11, Aug. 31, 2016, pp. 1353-1364.

G. Parmiani et al., "Opposite immune functions of GM-CSF administered as vaccine adjuvant in cancer patients", Annals of Oncology, vol. 18. No. 2, Nov. 20, 2006, pp. 226-232.

Wang et al.; Overcoming HBV immune tolerance to eliminate HBsAG-positive hepatocytes via pre-administration of GM-CFS as a novel adjuvant for a hepatitis B vaccine in HBV trangenic mice; Cellular & Molecular Immunology (2016) 13, © 2016 CSI and USTC. All rights reserved 1672-7681/16; www.nature.com/cmi; pp. 849-861.

Fruttaldo et al.; Anti-HBV vaccination before therapy with interferon (IFN) in chronic B hepatitis; Abstract; Eur Rev Med Pharracol Sci Nov.-Dec. 1997 1(6) 197-201. (2 pages).

* cited by examiner

SEQUENCE LISTING

```
<160> NUMBER OF SEQ ID NOS: 12

<210> SEQ ID NO 1
<211> LENGTH: 16
<212> TYPE: PRT
<213> ORGANISM: Artificial Sequence
<220> FEATURE:
<223> OTHER INFORMATION: PROSTATE CANCER

<400> SEQUENCE: 1

Cys Met Ser Ala Met Thr Asn Leu Ala Ala Leu Phe Pro Pro Glu Gly
1               5                   10                  15

<210> SEQ ID NO 2
<211> LENGTH: 18
<212> TYPE: PRT
<213> ORGANISM: Artificial Sequence
<220> FEATURE:
<223> OTHER INFORMATION: BREAST CANCER

<400> SEQUENCE: 2

Cys Tyr Thr Trp Asn Gln Met Asn Leu Ser Leu Gly Glu Gln Gln Tyr
1               5                   10                  15

Ser Val
```

<210> SEQ ID NO 3
<211> LENGTH: 10
<212> TYPE: PRT
<213> ORGANISM: Artificial Sequence
<220> FEATURE:
<223> OTHER INFORMATION: COLORECTAL CANCER

<400> SEQUENCE: 3

Tyr Leu Ser Gly Ala Asp Leu Asn Leu Cys
1               5                   10

<210> SEQ ID NO 4
<211> LENGTH: 33
<212> TYPE: PRT
<213> ORGANISM: Artificial Sequence
<220> FEATURE:
<223> OTHER INFORMATION: COLORECTAL CANCER E6

<400> SEQUENCE: 4

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

Cys

<210> SEQ ID NO 5
<211> LENGTH: 14
<212> TYPE: PRT
<213> ORGANISM: Artificial Sequence
<220> FEATURE:
<223> OTHER INFORMATION: HEPATOCELLULAR CARCINOMA (HCC)

<400> SEQUENCE: 5

Cys Arg Pro Gly Trp Arg Ala Ala Cys Asn Gln Lys Ile Leu
1               5                   10

<210> SEQ ID NO 6
<211> LENGTH: 19
<212> TYPE: PRT
<213> ORGANISM: Artificial Sequence
<220> FEATURE:
<223> OTHER INFORMATION: MULTIPLE MYELOMA (MAGE-A3)

<400> SEQUENCE: 6

Lys Val Ala Glu Leu Val His Phe Leu Phe Leu Trp Gly Pro Arg Ala
1               5                   10                  15

Leu Val Cys

<210> SEQ ID NO 7
<211> LENGTH: 17
<212> TYPE: PRT
<213> ORGANISM: Artificial Sequence
<220> FEATURE:
<223> OTHER INFORMATION: RENAL CELL CARCINOMA ACTIGEN (hTERT)

<400> SEQUENCE: 7

Glu Ala Arg Pro Ala Leu Leu Thr Ser Arg Leu Arg Phe Ile Pro Lys
1               5                   10                  15

Cys

<210> SEQ ID NO 8
<211> LENGTH: 29
<212> TYPE: PRT

```
<213> ORGANISM: Artificial Sequence
<220> FEATURE:
<223> OTHER INFORMATION: TYPE A STREPTOCOCCUS ANTIGEN (J8)

<400> SEQUENCE: 8

Gln Ala Glu Asp Lys Val Lys Gln Ser Arg Glu Ala Lys Lys Gln Val
1               5                   10                  15

Glu Lys Ala Leu Lys Gln Leu Glu Asp Lys Val Gln Cys
            20                  25

<210> SEQ ID NO 9
<211> LENGTH: 42
<212> TYPE: PRT
<213> ORGANISM: Artificial Sequence
<220> FEATURE:
<223> OTHER INFORMATION: HIV (C4-V3)

<400> SEQUENCE: 9

Lys Gln Ile Ile Asn Met Trp Gln Glu Val Gly Lys Ala Met Tyr Ala
1               5                   10                  15

Arg Pro Asn Cys Asn Thr Arg Lys Ser Ile His Ile Gly Pro Gly Arg
            20                  25                  30

Ala Phe Tyr Thr Thr Gly Glu Ile Ile Cys
        35                  40

<210> SEQ ID NO 10
<211> LENGTH: 255
<212> TYPE: PRT
<213> ORGANISM: Artificial Sequence
<220> FEATURE:
<223> OTHER INFORMATION: HBV (CODON OPTIMIZED PRES)

<400> SEQUENCE: 10

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Glu Ala Pro Lys Cys
        35                  40                  45

Pro Gly Gln Asn Leu Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
        115                 120                 125

Gln Gly Thr Ser Met Phe Pro Ser Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Leu Met Met Trp Tyr Trp Gly Pro Ser Leu Tyr Asn Ile
        195                 200                 205
```

```
Leu Arg Pro Phe Leu Pro Leu Leu Pro Ile Phe Phe Cys Leu Trp Val
            210                 215                 220

Trp Gly Pro Leu Gly Phe Phe Pro Asp His Gln Leu Asp Pro Ala Phe
225                 230                 235                 240

Gly Ala Asn Ser Asn Asn Pro Asp Trp Asp Phe Asn Pro Ser Ser
                245                 250                 255

<210> SEQ ID NO 11
<211> LENGTH: 768
<212> TYPE: DNA
<213> ORGANISM: Artificial Sequence
<220> FEATURE:
<223> OTHER INFORMATION: HBV (CODON OPTIMIZED PRES CDNA)

<400> SEQUENCE: 11
atggagagca ccacatctgg cttcctggga ccactgctgg tgctgcaggc tggcttcttt    60
ctgctgacca ggatcctgac aatccctcag tccctggaca gctggtggac ctccctgaac   120
tttctgggcg aggctcctaa gtgtccaggc cagaacctgc agtctccaac atccaatcac   180
agccccacct cttgtccccc tacatgccct ggctacagat ggatgtgcct gaggcggttc   240
atcatcttcc tgtttatcct gctgctgtgc ctgatctttc tgctggtgct gctggactat   300
cagggaatgc tgcccgtgtg ccctctgctg ccaggcacct ccaccacaag cacaggcccc   360
tgtaagacct gcacaatccc tgcccagggc accagcatgt tcccatcttg ctgttgcacc   420
aagccctctg atgcaactg tacatgcatc ccaatccct ccagctgggc cttcgctaga   480
tttctgtggg agtgggcttc cgtgcgcttt tcttggctgt ccctgctggt gcctttcgtg   540
cagtggtttg tgggcctgtc cccaaccgtg tggctgagcg tgatcctgat gatgtggtac   600
tggggcccaa gctgtataa atcctgagg cccttcctgc ctctgctgcc aatcttcttt   660
tgtctgtggg tgtggggccc cctgggcttc tttcctgacc atcagctgga tcccgccttc   720
ggcgctaact ctaacaatcc tgactgggac ttcaacccat cttcctga                768

<210> SEQ ID NO 12
<211> LENGTH: 119
<212> TYPE: PRT
<213> ORGANISM: Artificial Sequence
<220> FEATURE:
<223> OTHER INFORMATION: HUMAN PROSTATE CANCER

<400> SEQUENCE: 12

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala His Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Val Ala Pro Pro Pro Ala Ser
                85                  90                  95
```

-continued

```
Thr Asn Arg Gln Ser Gly Arg Gln Pro Thr Pro Ile Ser Pro Pro Leu
            100                 105                 110

Arg Asp Ser His Pro Gln Ala
        115
```

IMMUNOPOTENTIATOR, IMMUNOTHERAPEUTIC PHARMACEUTICAL COMPOSITION AND ITS PREPARATION AND USE

CROSS-REFERENCE TO RELATED APPLICATIONS

This application represents the national stage filing of PCT/CN2018/073916, filed Jan. 24, 2018, which claims priority to Chinese Application No. 201710021679.6 filed on Mar. 13, 2017, and Chinese Application No. 201810035029.1 filed Jan. 15, 2018, the entire content of which are incorporated herein by reference in this application.

FIELD OF THE INVENTION

The present invention relates to the field of biomedicine, in particular to an immune enhancer, an immunotherapeutic pharmaceutical composition and its preparation and use.

BACKGROUND OF THE INVENTION

With the nutritional status, health conditions and medical levels greatly improved, life expectancy increased steadily. However, major infectious diseases such as hepatitis B, AIDS, and tuberculosis, as well as persistent infectious diseases caused by other pathogenic microorganisms and tumors, have become the major problems endangering public health. Hepatitis B, AIDS and HPV, tuberculosis are major infectious diseases in the world. According to the statistics report by the Ministry of Health of China in 2008, there were 93 million people infected with hepatitis B virus in China, accounting for one-third of the total globally. Some of these patients needed effective clinical treatments which were lacking. The death toll from AIDS in China showed a sharp increase, occupying the first place for the death of infectious diseases for 4 consecutive years. HIV infection has shown a tendency to spread from the high-risk population to the general population. Multiple drug resistance and extensive drug resistance in tuberculosis treatment are becoming more serious problems. Tuberculosis resistance rate is climbing up to 28% in China. HPV infections are the other severe public health problem disregarding that fact that there are HPV vaccines available since 2000. In addition, there are many refractory chronic bacterial infections, such as chronic urinary tract infections, lung infections, not only causing recurrent attacks on patients but also representing the root of resistance stains.

According to data of the National Cancer Statistics Center, the number of cancer deaths was more than half million in United States which accounted for the 2nd leading death in 2014, and it was 6.57 million in China in 2009 which accounted for 26% of the total number of deaths in that year. The incidence of cancer was significantly increased in younger generations. The incidence of liver cancer in China is 27/100000, of which 90% are related to the persistent infection from the hepatitis B virus.

Therefore, persistent infections and tumors have increased economic and social burden dramatically, becoming a major threat to the public health.

Among them, Hepatitis B Virus (HBV) infection is considerably a severe infectious disease that seriously endangers public health. About 2 billion people in the world have been infected with HBV, and among them about 240 million are chronically infected and about 650,000 die of hepatic failure, liver cirrhosis and liver cancer due to HBV infection each year. About 93 million people are chronically infected with HBV in China, and among them about 20 million are chronic hepatitis B (CHB) patients. Sustainable and effective inhibition of HBV replication and seroconversion of Hepatitis B e antigen (HBeAg) has been considered to be a satisfactory endpoint for clinical treatment of CHB.

Hepatitis B antigen (HBsAg) disappearance and HBsAg seroconversion are considered as a clinical cure during the clinical treatment of hepatitis B. Therefore, to achieve clinical cure in CHB patients with seroconversion of HBsAg is a goal for any approach to treat CHB. However, HBsAg seroconversion rates are 1-2% per year naturally. In a double-blind, randomized controlled clinical cohort study, HBsAg disappearance was achieved only in 3% among HBeAg-positive CHB patients treated with tenofovir dipivoxil for 1 year. In another randomized controlled clinical study, HBsAg disappearance was achieved in 8.5% among HBeAg-positive CHB patients treated with entecavir sequentially with PEGylated-interferon-alfa for 3-4 years. Another randomized controlled trial of PEGylated-interferon-alpha for HBeAg-negative CHB patients for 1 year, follow-up at 3 years after the end of treatment found that HBsAg of 8.7% of patients had been cleared. These data showed that clearance of HBsAg in CHB patients remains a most difficult task. Therefore, there is an urgent need to cure HBV (which has been called from WHO) by developing new drugs and treatments against hepatitis B chronic infections.

The primary reason that hepatitis B cannot be currently cured is the immune tolerance in CHB patients caused by the loss or failure of the HBV-specific cellular immune function in the patients. Hepatitis B therapeutic vaccine is a new approach for the hepatitis B treatment, and it targets on breaking the immune tolerance of HBV-infected patients, remodeling or stimulating patients to produce neutralizing antibodies and cellular responses against HBV. Currently, there are DNA based vaccines, DC based vaccines, genetic engineered protein based vaccines and antigen-antibody complexes based under clinical investigations to evaluate their efficacy. Noticeably, there are some foreseeable problems with the above therapeutic vaccines. For example, a poor immunogenicity is associated with the DNA vaccines. There are technical difficulties along with quality control issues and high costs in preparing DC vaccines as it requires in vitro loaded antigens, which are put back inside of a patient. Low ability to stimulate host cellular responses were associated with the recombinant protein vaccines on the basis of the existing clinical results. All these shortcomings may fail to break immune tolerance needed to achieve clinical benefits for CHB treatments.

Thus, there is an urgent need to develop an immunotherapeutic vaccine that can break immune tolerance and effectively treat diseases not only against persistent microbial infections but also against tumors.

The traditional vaccines refer to biological products prepared by attenuated, inactivated pathogenic organisms (bacteria, viruses, etc.) or genetic engineering antigen components. Modern vaccines are more related to genetic engineering antigen components. Vaccination not only protects individuals against the spread of infectious pathogens but also limits the spread of infectious pathogens in the population. The mechanism of vaccination is through the activation of the host immune system and eventually production of a specific immune memory in response to the corresponding pathogens to clear pathogens quickly once encountered the same pathogens, so as to achieve long-term preventions. Therapeutic vaccines have the same long-term efficacy as preventive vaccines. Unlike preventive vaccines which are used in healthy human subjects, therapeutic vaccines are targeted at pathogens which are already infected and hidden in tissues in patients through reactivating or repairing the host immune system to treat diseases. At the present, the research on therapeutic vaccines mainly focuses on major chronic diseases that do not have effective treatments, such as persistent infectious diseases as well as malignant tumors. As discussed above, these diseases have a huge patient population in China. Improving the development of therapeutic vaccines against these chronic diseases and malignant tumors can not only solve adverse effects often associated with small-molecule drugs, it can also have the significance of little side effects, long efficacy and good specificity.

Therapeutic vaccine becomes more and more inseparable from the role of adjuvants as therapeutic vaccine developments often require potent adjuvants. Especially, adjuvants are necessary for the therapeutic vaccines based on the recombinant protein antigens to achieve desired immunotherapeutic efficacy. Adjuvant is an agent which can assist therapeutic vaccine to enhance adaptive immune responses against the pathogens by breaking the immune tolerance, extending its duration of protection, and inducing specific type of immune responses. However, there are many difficulties in the use of or development of adjuvants for this purpose. Some of the difficulties include the side effects of adjuvants, the effectiveness of adjuvants and the issue how to effectively increase the immune response of an antigen in respect to an adjuvant's dose. Thus, one of the difficulties is how to choose a "right" adjuvant to achieve desired effectiveness.

SUMMARY OF THE INVENTION

In view of shortcomings of the current technology, the invention provides immune enhancers and immunotherapeutic pharmaceutical compositions, discloses a method for preparing the immunotherapeutic pharmaceutical compositions, and the use of immune enhancers and related immunotherapeutic drugs. The specific technical solutions of the invention are listed as follow:

In one aspect, the invention provides an immune enhancer comprising at least a recombinant interferon-alfa (rIFN-α) and a recombinant granulocyte-macrophage colony stimulating factor (rGM-CSF).

Preferably, in the above-mentioned immune-enhancer, the ratio of the content by weight of rIFN-α to the content of rGM-CSF is in the range of $(0.1 \times 10^4$ IU-$5 \times 10^6$ IU):(1 µg-200 µg), per dose.

More preferably, the ratio of the content of rIFN-α to the content of rGM-CSF is in the range of $(0.5 \times 10^4$ IU-$1 \times 10^5$ IU):(5 µg-150 µg), per dose.

More preferably, the ratio of the content of rIFN-α to the content of rGM-CSF is in the range of $(0.5 \times 10^4$ IU-$5 \times 10^4$ IU):(5 µg-50 µg), per dose.

Most preferably, the ratio of the content of rIFN-α to the content of rGM-CSF is in the range of $1 \times 10^4$ IU:10 µg, per dose.

In one preferred embodiment, the content of rGM-CSF in the above-mentioned immune-enhancing agent is in the range of about 1 µg to about 100 µg, per dose; preferably in the range of about 5 µg to about 50 µg, per dose; more preferably in the range of about 5 µg to about 20 µg, per dose; and most preferably about 10 µg, per dose.

In another preferred embodiment, the content of rIFN-α in the above-mentioned immune-enhancing agent is in the range of $1 \times 10^3$ IU-$9 \times 10^6$ IU, per dose, preferably in range of $5 \times 10^3$ IU-$5 \times 10^5$ IU, per dose, more preferably in the range of $8 \times 10^3$ IU-$2 \times 10^5$ IU, per dose, and most preferably in the range of about $0.5 \times 10^4$ IU-$1 \times 10^5$ IU, such as $1 \times 10^4$ IU, per dose.

In another preferred embodiment, the above-mentioned immune enhancer may further include an aluminum adjuvant, such as aluminum hydroxide and/or aluminum phosphate.

In one example, the amount of aluminum adjuvant is in the range of about 0.5 mg-about 10 mg, per dose; preferably in range of about 1 mg-about 3 mg, per dose; more preferably in the range of about 1.25 mg-about 2.5 mg, per dose. In another example, the amount of aluminum adjuvant is in the range of about 0.1 mg-about 3 mg, per dose; preferably in the range of about 0.8 mg-about 2 mg, per dose; most preferably about 1.25 mg, per dose. In yet another example, the amount of aluminum adjuvant is in the range of about 0.01 mg-about 3 mg, per dose; preferably in the range of about 0.05 mg-about 2 mg, per dose; most preferably in the range of about 0.1 mg-about 0.5 mg, per dose, such as about 0.125 mg, per dose.

In one example, the weight ratio of aluminum adjuvant to rGM-CSF is in the range of (about 0.01 mg to about 1 mg):(about 1 µg to about 200 µg), per dose; preferably in the range of (about 0.05 mg to about 0.5 mg):(about 5 µg to about 150 µg), per dose; more preferably the ratio is in the range of (about 0.1 mg-about 0.25 mg):(about 5 µg-about 50 µg), per dose; most preferably, the weight ratio is about 0.125 mg:about 10 µg, per dose. In another example, the weight ratio of aluminum adjuvant to rGM-CSF is in the range of (about 0.1 mg to about 10 mg):(about 1 µg to about 300 µg), per dose; preferably in the range of (about 0.5 mg to about 5 mg):(about 2 µg to about 200 µg), per dose; more preferably the weight ratio is in the range of (about 1.5 mg to about 3 mg):(about 5 µg to about 100 µg), per dose; most preferably, the weight ratio is in the range of (about 1 mg to about 2 mg):(about 10 µg to about 75 µg), per dose.

Preferably, the above-mentioned interferon is interferon alpha (IFN-α).

More preferably, the above-mentioned interferon is rIFN-α-2a.

In another aspect, the invention provides an immunotherapy pharmaceutical composition, which includes at least an antigen and the above-mentioned immune enhancer.

In one embodiment, rIFN-α in the immunotherapy pharmaceutical composition is interferon alpha-2a.

In another embodiment, the antigen in the immunotherapy pharmaceutical composition includes the protein antigen.

Preferably, the protein antigen is at least one of the virus antigens, bacterial antigens, fungal antigens, parasitic antigens and tumor antigens.

More preferably, the above-mentioned viral antigens include at least one of HBV antigens, herpes virus antigens, HPV antigens, HIV antigens, Merkel cell virus, influenza virus antigens and RSV antigens.

In another embodiment, the above-mentioned protein antigens are inactivated vaccine antigens, attenuated vaccine antigens or subunit vaccine antigens.

In another embodiment, the protein antigen is a genetic engineering vaccine antigen. In one embodiment, the above-mentioned immunotherapeutic pharmaceutical composition further comprises at least one of pharmaceutically or immunologically acceptable carriers or excipients.

In the above-mentioned immunotherapeutic pharmaceutical compositions, the ratio of the content of rIFN-α to the content of rGM-CSF is in the range of (about $0.5×10^4$ IU to about $1.5×10^4$ IU):(about 5 μg to about 20 μg), per dose; preferably the ratio is about $1×10^4$ IU:about 10 μg, per dose.

In the above-mentioned immunotherapeutic pharmaceutical compositions, the content of rGM-CSF is in the range of about 1 μg to about 200 μg, per dose; preferably from about 5 μg to about 50 μg, per dose; more preferably from about 5 μg to about 20 μg, per dose; and most preferably from about 10 μg, per dose.

In the above-mentioned immunotherapeutic pharmaceutical compositions, the content of the rIFN-α is in the range of about $1×10^3$ IU to about $9×10^5$ IU, per dose; preferably about $5×10^3$ IU to about $1×10^5$ IU, per dose; more preferably about $8×10^3$ IU to about $5×10^4$ IU, per dose; most preferably about $1×10^4$ to about $2×10^4$ IU, such as about $1×10^4$ IU, per dose.

In the above-mentioned immunotherapeutic pharmaceutical composition, the content ratio of antigen to rGM-CSF is in the range of (about 0.1 μg-about 10 μg):(about 1 μg-about 100 μg), per dose; preferably (about 0.5 μg-about 5 μg):(about 5 μg-about 50 μg), per dose; more preferably (about 1 μg to about 5 μg):(about 5 μg to about 25 μg), per dose; most preferably about 1 μg:about 10 μg, per dose.

In another aspect, the invention provides a method of preparing an immunotherapeutic pharmaceutical composition comprising the steps of: mixing an antigen with a rIFN-α and a rGM-CSF to form a mixture, and then adding to the mixture at least one of pharmaceutically or Immunologically acceptable carriers or excipients, thereby producing the above-mentioned immunotherapeutic pharmaceutical compositions.

In one embodiment, the rGM-CSF, the rIFN-α and the antigen are mixed at 4-10° C., preferably at 4° C.

In another aspect, the invention provides the use of the above-mentioned immune enhancer, comprising administering a safe and effective amount of the above-mentioned immune enhancer, prior to the administration of the antigen or co-administration of the antigen and the immune enhancer to the subject to be immunized.

Preferably, the above administration includes at least mucosal administration or injection administration, more preferably local injection administration.

Preferably, the subject to be immunized as described above is a mammal, including a human or a non-human mammal. Non-human mammals include rodents such as rodent, rabbit, feline, canine, swine, and cattle.

In another aspect, the invention provides the use of the immunotherapeutic pharmaceutical compositions in the preparation of an immunotherapeutic drug, the use comprising the steps of:
(1) promoting monocytes production;
(2) promoting expression of monocytes CCR2;
(3) promoting differentiation of $Ly6C^{hi}CCR2^+$ monocytes into DCs with phenotype $CD11b^+$ $CD11c^+$ DCs;
(4) improving the cellular immunity and CTL cytolytic functions of a subject; and
(5) promoting the humoral immunity of the subject and production of one or several protective antibodies.

Preferably, the above-mentioned uses include prevention or treatment of one or more of viral infections, bacterial infections, fungal infections, parasitic infections and/or tumors.

More preferably, the above-mentioned virus infections include one or more of HBV infection, herpes virus infection, HPV infection, HIV infection, Merkel cell virus (e.g., Merkel cell polyomavirus (MCV or MCPyV)) related infection, influenza virus infection and RSV infection.

In one preferred embodiment, the virus infection is chronic hepatitis B.

In another preferred embodiment, when the antigen is hepatitis surface antigen, the immunotherapeutic pharmaceutical composition can break the immune tolerance, eliminate infected hepatocytes, clear both HBeAg and HBsAg, and produce anti-HBs Ab.

In another preferred embodiment, when the antigen is preS1 with the hepatitis surface antigen, the immunotherapeutic pharmaceutical composition can break the immune tolerance, eliminate infected hepatocytes, clear both HBeAg and HBsAg, and produce anti-HBs Ab.

In another preferred embodiment, when the antigen is a tumor antigen, the immunotherapeutic pharmaceutical composition induce effective anti-tumor immune responses.

In another preferred embodiment, the above-mentioned tumor antigens include prostate cancer epitope peptides or polypeptides, breast cancer epitope peptides or polypeptides, colorectal cancer epitope polypeptides, cervical cancer epitope peptides or polypeptides, liver cancer epitope peptides or polypeptides, multiple myeloma Epitope peptides and a renal cell carcinoma epitope peptides or polypeptides.

In another preferred embodiment, when the antigen is a streptococcal antigen, the immunotherapeutic pharmaceutical composition induces immune responses that produce antibacterial infections.

In another preferred embodiment, the streptococcal antigen is one of *Streptococcus* type A epitope peptides or polypeptides.

In another preferred embodiment, when the antigen is an HIV antigen, the immunotherapeutic pharmaceutical composition induces immune responses against HIV infection.

In another preferred embodiment, the HIV antigen is one of HIV epitope peptides or polypeptides.

Preferably, the above-mentioned uses include administration of a safe and therapeutically effective amount of the immunotherapeutic pharmaceutical composition as discussed herein to the subject to be immunized.

More preferably, the above-mentioned subject to be immunized is a mammal, including a human or a non-human mammal. Non-human mammals include rodents, rabbits, felines, canines, swine, and cattle.

Compared with currently existing technologies, the compositions of immune enhancers and related methods and uses in the invention have the following advantages:

(1) The invention uses a mixture comprising rGM-CSF and rIFN-α at optimal ratios as immune enhancers, which can remarkably improve the immune function, improve the efficiency of antigen presentation, effectively break immune tolerance and establish an effective immune activation and response, produce strong antibody and cellular immune responses;

(2) The immune enhancers comprising rGM-CSF and rIFN-α at optimal ratios as described can effectively activate humoral and cellular immunity and significantly enhance the immune efficacy;

(3) A mixture or a combination of the immune enhancer and the hepatitis B surface antigen can be used to successfully break the immune tolerance in a hepatitis B infectious animal model, and the HBsAg can be cleared accompanied by its anti-HBs antibodies;

(4) A mixture or a combination of the immune enhancer and the tumor antigen can be used to induce the anti-tumor immune response;

(5) A mixture or a combination of the immune enhancer and a streptococcal antigen can be used to induce an immune response that produces an antibacterial infection;

(6) A mixture or a combination of the immune enhancer and the HIV antigen can be used to induce an immune response that produces anti-HIV infection;

(7) The immune enhancer is easy to use, with low cost, low adverse reaction and side effects.

It should be understood that, within the scope of the present invention, each technical feature of the present invention described above and various technical features described in the following (as examples) may be combined with each other to form a new or preferred technical solution. Any equivalents or modifications without departing from the principle disclosed in the invention falls into the protection scope of the invention.

The invention will be further described with the figures to fully illustrate the objectives, technical features and technical effects of the invention. The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1A: Peripheral blood CD11b$^+$CD11c$^+$DC ratio on day 3 after immunization. At 21 days after immunization, 10 μg of HBsAg was injected into the left foot pad of mice and PBS was injected into the right foot pad as a control. The swelling of the foot pad was measured at 24 h, 48 h and 72 h after injection, respectively. FIG. 1B: Statistical results of 24 h DTH. FIG. 1C: Peripheral blood was collected 21 days after immunization, serum was separated and anti-HBsAg levels were measured by ELISA. Results are expressed as mean±SEM, * indicates P<0.05;  indicates P<0.01; * indicates P<0.001.

FIG. 2A: Peripheral blood CD11 b+CD11c+DC ratio on day 3 after immunization. At 21 days after immunization, 10 μg of HBsAg was injected into the left foot pad of mice and PBS was injected into the right foot pad as a control. The swelling of the foot pad was measured at 24 h, 48 h and 72 h after injection, respectively. FIG. 2B: Statistical results of 24 h DTH. FIG. 2C: Peripheral blood was collected 21 days after immunization, serum was separated and anti-HBsAg levels were measured by ELISA. Results are expressed as mean±SEM, * indicates P<0.05; ** indicates P<0.01.

FIG. 3A: The ratio of CD11b$^+$CD11c$^+$ DCs in peripheral blood on day 3 after immunization. FIG. 3B: The ratio of CD11b$^+$CD11c$^+$ DCs in mouse lymph nodes on the 3rd day after immunization. FIG. 3C: The anti-HBsAg level in serum for 21 days. Results are expressed as mean±SEM, ns for P>0.05; * for P<0.05; **for P<0.01.

FIG. 4A: Immunization strategy for different experimental groups in this experiment. FIG. 4B: At day 7 after the second immunization, 10 μg of HBsAg antigen was injected into the left foot pad of mice, and PBS was injected into the right foot pad as a negative control. Twenty-four hours later, the swelling of the foot pad was observed. FIG. 4C: The degree of swelling at 24 hrs, 48 hrs, 72 hrs after injection of HBsAg antigen in mouse foot pads. ns (P>0.05) showed no statistical difference, *(P<0.05) showed statistical difference, **(P<0.01) showed significant statistical difference.

FIG. 5A: Results of HBsAb concentrations measured by ELISA after immunizations with different immunotherapeutic pharmaceutical compositions. FIG. 5B: On the 7th day after the second immunization, the HBsAg-specific IgG1 and IgG2a concentrations in different immunized groups were detected by ELISA. FIG. 5C: On the 7th day after the second immunization, the ratio of HBsAg-specific IgG2a to IgG1 was detected by ELISA. ns (P>0.05) indicated no statistical difference, **(P<0.01) indicated significant statistical difference.

FIG. 8A: The strategy of flow cytometry data analysis. FIG. 8B: CTL flow cytometry results for different immunization groups. FIG. 8C: CTL killing rate statistical results of different HBV-specific immune group. ns ($P>0.05$) indicated no statistical difference, **($P<0.01$) indicated significant statistical difference.

FIG. 9A: The level of IL-12 in DC2.4 cells. FIG. 9B: The statistical results respectively. Serum IL-12 concentrations were measured by ELISA on days 3, 7, 14 and 21 after immunization. FIG. 9C: Serum IL-12 concentrations results at 21 days. ns ($P>0.05$) showed no statistical difference, *($P<0.05$) showed statistical difference, **($P<0.01$) showed significant statistical difference.

FIG. 10A: Flow cytometry results for blood $CD11b^+CD11c^+$ DC Cells in different drug combinations-treated mice. FIG. 10B and FIG. 10C: the percentage and amount of $CD11b^+CD11c^+$ DC in mouse blood, respectively. FIG. 10D: CD80 expression level for $CD11b^+CD11c^+$ DC cells. FIG. 10E: The MHC-II expression level of $CD11b^+CD11c^+$ DC cells. ns ($P>0.05$) showed no statistical difference, *($P<0.05$) showed statistical difference, **($P<0.01$) showed significant statistical difference.

FIG. 11A and FIG. 11B: flow cytometry analysis strategy and results of the $CD11b^+Ly6C^+$ monocytes in different drug combinations-treated mice. FIG. 11C and FIG. 11D: the percentage and amount of $CD11b^+Ly6C^+$ monocytes in mouse blood, respectively. FIG. 11E: The expression level of MHC-II of $CD11b^+Ly6C^+$ monocytes. FIG. 11F: The level of MCP-1 in serum of mice detected by ELISA after 21 days of immunization. ns ($P>0.05$) showed no statistical difference, *($P<0.05$) showed statistical difference, **($P<0.01$) showed significant statistical difference.

FIG. 12A: Male C57B/L6 mice, 6-8 weeks old, were selected and injected with rAAV-1.3HBV virus via the tail vein at a dose of $1 \times 10^{10}$ μg/100 μL per mouse. FIG. 12D, FIG. 12E, FIG. 12C and FIG. 12G: 14 days after injection, the serum levels of HBeAg, HBsAg, HBV-DNA and ALT in mice detected respectively. FIG. 12B: Immunohistochemical results of HBcAg in liver, heart and kidney respectively. The cells indicated by the arrow are HBcAg positive cells. FIG. 12F: Hematoxylin-eosin staining results of HBcAg in liver, heart and kidney, respectively. ns ($P>0.05$) showed no significant difference, $P<0.0001$ showed significant statistical difference, Bar=200 μm.

FIG. 13A, FIG. 13B and FIG. 13C: the levels of HBsAg, HBV-DNA and ALT in the sera from 0 week to 12 weeks after infection were monitored.

FIG. 14A: Serum HBsAg concentrations at different time points in 9 experimental groups. FIG. 14B: Serum HBeAg at different time points in 9 experimental groups, dotted line S/CO=1. ns ($P>0.05$) showed no statistical difference, *($P<0.05$) showed statistical difference, **($P<0.01$) showed significant statistical difference.

FIG. 15A: Flow cytometry analysis strategy for $CD11b^+CD11c^+$ DC in blood. FIG. 15B: The proportion of $CD11b^+CD11c^+$ DC in the blood of different immunized groups. FIG. 15C: The statistical result of $CD11b^+CD11c^+$ DC in blood of different immunized groups. FIG. 15D and FIG. 15E show the expression of CD80, CD86, MHC-I and MHC-II on $CD11b^+CD11c^+$ DC in blood of different immunized groups and statistical results. ns ($P>0.05$) showed no statistical difference, *($P<0.05$) showed statistical difference, **($P<0.01$) showed significant statistical difference.

FIG. 16A: Flow cytometry analysis strategy for monocytes in the blood. FIG. 16B: The proportion of $CD11b^+Ly6G^+Ly6C^+$ granulocytes, $CD11b^+Ly6G^-Ly6C^{hi}$ monocytes and $CD11b^+Ly6G^-Ly6C^+$ monocytes in the blood of different immunized groups. FIG. 16C: The statistical results of $CD11b^+Ly6G^+Ly6C^+$ granulocytes, $CD11b^+Ly6G^-Ly6C^{hi}$ monocytes and $CD11b^+Ly6G^-Ly6C^+$ monocytes in the blood of different immunized groups. FIG. 16D: The statistical results of CCR2 expression in $CD11b^+Ly6G^+Ly6C^+$ granulocytes, $CD11b^+Ly6G^-Ly6C^{hi}$ monocytes and $CD11b^+Ly6G^-Ly6C^+$ monocytes in blood of different immunized groups. ns ($P>0.05$) showed no statistical difference, *($P<0.05$) showed statistical difference, **($P<0.01$) showed significant statistical difference.

FIG. 17A: Seven days after the fourth immunization, the HBsAg (10 μg/10 μL) antigen was injected into the left footpad of the mouse and the right footpad was injected with PBS as a control. After 24 h, the caliper thickness was measured with a vernier caliper, Pad swelling thickness=left pad thickness−right pad thickness. FIG. 17B: The statistical results of proliferation of $CD8^+$ T cells in different immunized groups, CD3 (1 μg/mL) and CD28 (100 ng/mL) as a positive control. FIG. 17C and FIG. 17D, respectively, splenic IFN-$\gamma^+CD4^+$ T cells and IL-$4^+CD4^+$ T cells statistical results in different immunized groups. FIG. 17E: Flow cytometric analysis of splenic IFN-$\gamma^+CD8^+$ T cells in different immunized groups, ionomycin (1 μg/mL) and PMA (100 ng/mL) as positive controls. FIG. 17F: Statistical results of splenic IFN-$\gamma^+CD8^+$ T cells in different immunized groups. FIG. 17G: CD8$^+$ T cells in liver in different immunized groups measured by Immunohistochemical method, Bar=100 μm. Flow cytometric result (left) and statistical results (right) of CTL assays in vivo (H) and (I). ns (P>0.05) showed no statistical difference, *(P<0.05) showed statistical difference, **(P<0.01) showed significant statistical difference.

FIG. 18A: Serum HBeAg results. FIG. 18B: Serum HBsAg results. FIG. 18C: Serum HBV-DNA results, the dotted line for the kit detection limit of 30 IU/mL. FIG. 18D: Serum ALT results. FIG. 18E: Immunohistochemical results of HBcAg in liver, bar=50 μm. FIG. 18F: Serum anti-HBsAg results. FIG. 18G: Serum IgG2a/IgG1 results. ns (P>0.05) showed no statistical difference, *(P<0.05) showed statistical difference, **(P<0.01) showed significant statistical difference.

FIG. 19C: The statistical result of the ratio of CD11b$^+$ CD11c$^+$ DC in peripheral blood. FIG. 19D: The statistical result of the proportion of IFN-γ$^+$ CD8$^+$ T cells in the spleen. FIG. 19E, FIG. 19F and FIG. 19G: The results of serum ALT, HBsAg and HBV-DNA respectively. FIG. 19H: Immunohistochemical results of liver HBcAg, Bar=50 μm. ns (P>0.05) showed no statistical difference, *(P<0.05) showed statistical difference, **(P<0.01) showed significant statistical difference.

FIG. 20 is a set of graphs showing immune effects of the immunotherapeutic pharmaceutical composition treatments on the enhancement of the prostate cancer peptide vaccine according to certain embodiments of the invention. Animals were immunized with the compositions and induced in antibody productions (FIG. 20A), and size changes in footpad swelling after such immunizations and then an antigen challenged, indicating cellular immune responses (FIG. 20B).

FIG. 21 is a set of graphs showing immune effects of the immunotherapeutic pharmaceutical composition treatments on the enhancement of the breast cancer peptide vaccine according to certain embodiments of the invention. Animals were immunized with the compositions and induced in antibody productions (FIG. 21A), and size changes in footpad swelling after such immunizations and then an antigen challenged, indicating cellular immune responses (FIG. 21B).

FIG. 22 is a set of graphs showing immune effects of the immunotherapeutic pharmaceutical composition treatments on the enhancement of the colorectal cancer peptide vaccine according to certain embodiments of the invention. Animals were immunized with the compositions and induced in antibody productions (FIG. 22A), and size changes in footpad swelling after such immunizations and then an antigen challenged, indicating cellular immune responses (FIG. 22B).

FIG. 23 is a set of graphs showing immune effects of the immunotherapeutic pharmaceutical composition treatments on the enhancement of cervical cancer peptide vaccine according to certain embodiments of the invention. Animals were immunized with the compositions and induced in antibody productions (FIG. 23A), and size changes in footpad swelling after such immunizations and then an antigen challenged, indicating cellular immune responses (FIG. 23B).

FIG. 24 is a set of graphs showing immune effects of the immunotherapeutic pharmaceutical composition treatments on the enhancement of the hepatocellular carcinoma peptide vaccine according to certain embodiments of the invention. Animals were immunized with the compositions and induced in antibody productions (FIG. 24A), and size changes in footpad swelling after such immunizations and then an antigen challenged, indicating cellular immune responses (FIG. 24B).

FIG. 25 is a set of graphs showing immune effects of the immunotherapeutic pharmaceutical composition treatments on the enhancement of the multiple myeloma peptide vaccine immunization according to certain embodiments of the invention. Animals were immunized with the compositions and induced in antibody productions (FIG. 25A), and size changes in footpad swelling after such immunizations and then an antigen challenged, indicating cellular immune responses (FIG. 25B).

FIG. 26 is a set of graphs showing immune effects of the immunotherapeutic pharmaceutical composition treatments on the enhancement of the peptide vaccine of renal cell carcinoma according to certain embodiments of the invention. Animals were immunized with the compositions and induced in antibody productions (FIG. 26A), and size changes in footpad swelling after such immunizations and then an antigen challenged, indicating cellular immune responses (FIG. 26B).

FIG. 27 is a set of graphs showing Immune effects of the immunotherapeutic pharmaceutical composition treatments on the enhancement of the type A streptococcal vaccine in a better example of the invention. Animals were immunized with the compositions and induced in antibody productions (FIG. 27A), and size changes in footpad swelling after such immunizations and then an antigen challenged, indicating cellular immune responses (FIG. 27B).

FIG. 28 is a set of graphs showing immune effects of the immunotherapeutic pharmaceutical composition treatments on the enhancement of the HIV-1 peptide vaccine in a better example of the invention. Animals were immunized with the compositions and induced in antibody productions (FIG. 28A), and size changes in footpad swelling after such immunizations and then an antigen challenged, indicating cellular immune responses (FIG. 28B).

FIG. 29 is a set of graphs showing immune effects of the immunotherapeutic pharmaceutical composition treatments on the enhancement of the HBV PreS and HBV PreS1 in a better example of the invention. The doses for the optimal composition of GM-CSF is at 10 μg, IFN-α at 10,000 IU, PreS at 1 μg, or PreS1 at 1 μg. Six-week-old female Balb/c mice were injected subcutaneously 3 times with biweekly intervals with optimal dose ratio of GM-CSF/IFN-α/PreS or GM-CSF/IFN-α/PreS1, respectively. The control groups were immunized individually with PreS or PreS1. Blood samples were collected before and after each immunization to detect humoral immunity.

DETAILED DESCRIPTION OF THE PREFERRED EMBODIMENT

In General

Figure 1:
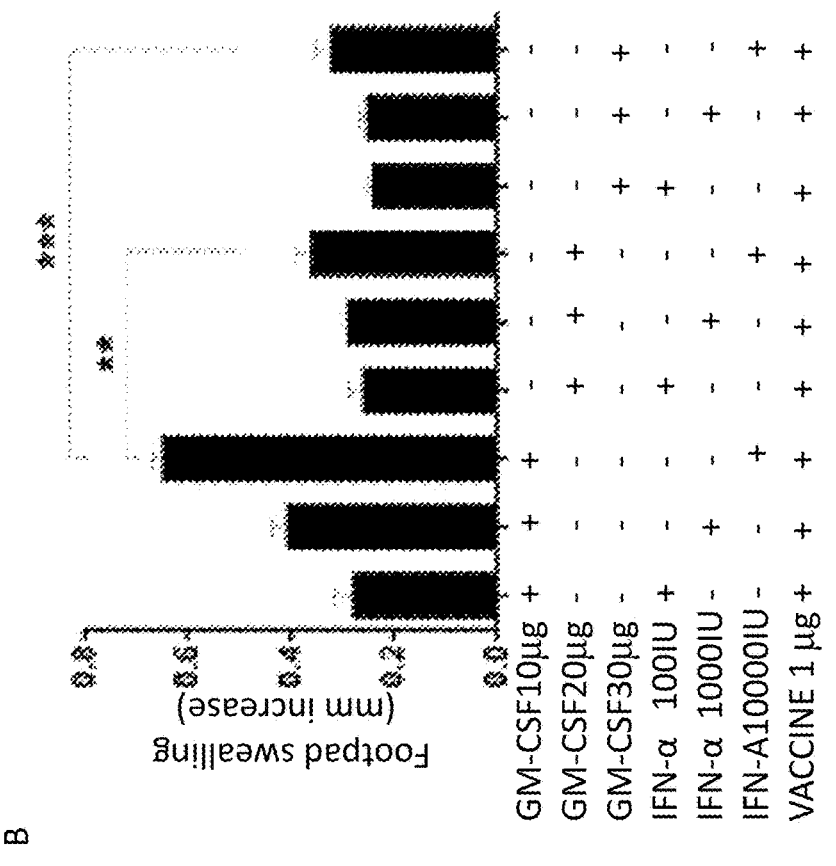
FIG. 1 is a set of graphs and images showing effects of different ratios and combinations by the use of the immunotherapeutic pharmaceutical composition treatments. C57BL/6 mice were immunized with 10 μg, 20 μg, 30 μg GM-CSF combination with 100 IU, 1,000 IU, 10,000 IU IFN-α respectively and 1 ug HBV vaccine.
Figure 1:
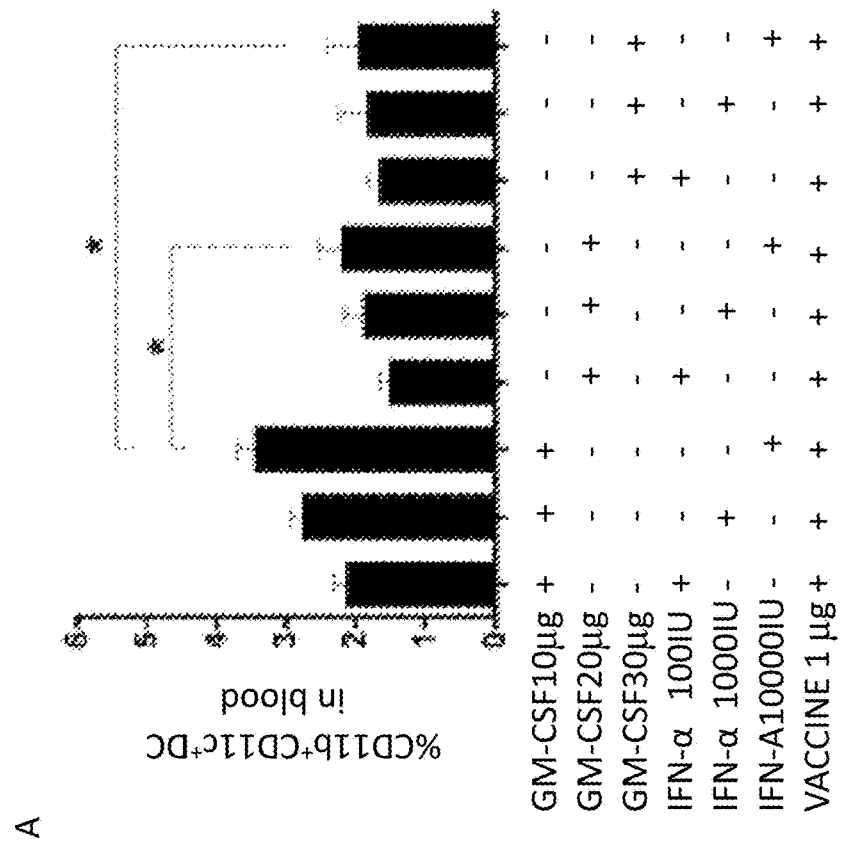
Figure 1:
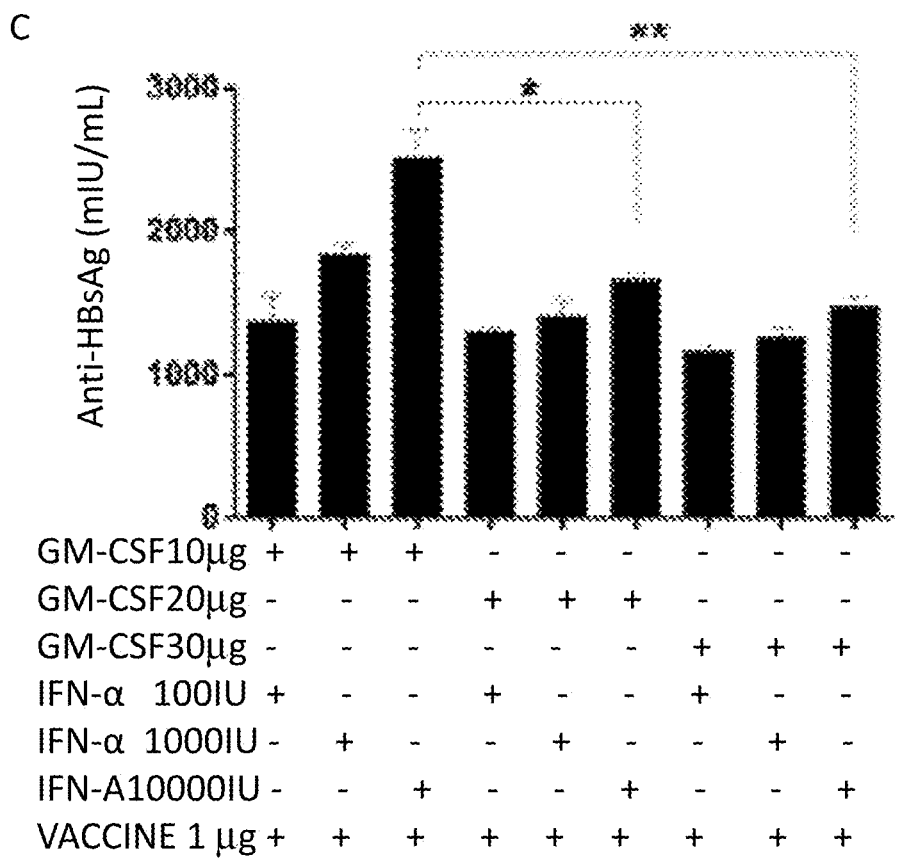

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is further understood that this invention is not limited to the particular methodology, protocols, materials, and reagents described, as these may vary. It is also to be understood that the terminology used herein is for the purpose of describing particular embodiments only and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art.

Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

I. Definitions

Unless defined otherwise, all technical and scientific terms used herein have the same meaning as commonly understood by one of ordinary skill in the art to which this invention belongs. As used herein the following terms have the following meanings.

The term "comprising" or "comprises," as used herein, is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about," when used before a numerical designation, e.g., temperature, time, amount, and concentration, including range, indicates approximations which may vary by (+) or (−) 10%, 5% or 1%.

The term "immune enhancer," as used herein, refers to any agent or substance capable of boosting, enhancing, or otherwise augmenting the natural immune response. In one embodiment, the present disclosure reveals an immune enhancer comprising at least an interferon such as a recombinant interferon, a granulocyte-macrophage colony-stimulating factor such as a recombinant granulocyte-macrophage colony-stimulating factor. In one preferred embodiment, an immune enhancer comprises a rIFN-α and a rGM-CSF.

The term "pharmaceutical composition," as used herein, refers to any chemical or biological compound or substance, or a mixture or combination of two or more such compounds or substances, intended for use in the medical diagnosis, cure, treatment, or prevention of disease or pathology.

The term "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In one embodiment, the inventive compositions or methods can provide any amount of any level of treatment or prevention of a disease in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof. With respect to the inventive methods, the cancer can be any cancer, including any of the cancers associated with any of the tumor antigens described herein.

The present invention is applicable to any mammal. As used herein, the term "mammal" refers to a warm-blooded vertebrate animal such as a human, dog or cat or the like. In one embodiment, mammal includes rodents such as rodent, rabbit, feline, canine, swine, and cattle.

The terms "administer" or "administration," as used herein, refers to their usual and ordinary meaning in the art of treating a patient with a substance such as a vaccine or a composition. The terms "co-administration" and "concomitant administration" as used herein are synonymous and refer to administering two substances or two compositions to a patient in such a manner and with such timing that both substances or both compositions reside in the patient's body at the same time. The co-administration may be simultaneous or sequential in time, and the co-administered substances or compositions may be administered to a patient at the same time, or separately but near in time, or on the same day, or otherwise in a way that results in substantial overlap of the residence periods for the respective substances or compositions in the body. The administration, e.g., parenteral administration, may include subcutaneous administration, intramuscular administration, transcutaneous administration, intradermal administration, intraperitoneal administration, intraocular administration, intranasal administration and intravenous administration.

The vaccine or the composition according to the invention may be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, the vaccine may be applied by topical application as a drop, spray, gel or ointment to the mucosal epithelium of the eye, nose, mouth, anus, or vagina, or onto the epidermis of the outer skin at any part of the body. Other possible routes of application are by spray, aerosol, or powder application through inhalation via the respiratory tract. In this last case the particle size that is used will determine how deep the particles will penetrate into the respiratory tract. Alternatively, application may be via the alimentary route, by combining with the food, feed or drinking water e.g. as a powder, a liquid, or tablet, or by administration directly into the mouth as a: liquid, a gel, a tablet, or a capsule, or to the anus as a suppository.

II. Description of Preferred Embodiments of the Invention

Before describing the invention, it is to be understood that this invention is not limited to particular methods and experimental conditions described, as such methods and conditions may vary. It is also to be understood that the terminology used herein is for the purpose of describing particular embodiments only, and is not intended to be limiting, the scope of the invention being limited only by the appended claims.

After extensive studies, applicants discovered for the first time that the optimal ratio of mixture of rGM-CSF and rIFN-α, as immune enhancers, can significantly improve the immunity of the body (e.g., when mixed with a protein antigen), improve the efficiency of antigen presentation and establish an effective immune activation and response; elicit strong antibody and cellular immune responses, to prevent and treat diseases. Mixing the immune enhancers with the hepatitis B vaccine successfully breaks the immune tolerance in hepatitis B animal model, and lead to elimination of HBsAg and induction of anti-HBs Abs.

The objective of the invention is to provide novel immunotherapeutic pharmaceutical compositions, and particularly to immunotherapeutic pharmaceutical compositions against persistent viral infections and tumors. The pharmaceutical compositions of the invention can be used as new immunotherapy drugs for the treatment of many diseases or viruses such as HBV, herpes virus, HPV, HIV, Merkel cell virus, influenza virus and RSV.

In one embodiment, the immunotherapeutic pharmaceutical composition comprises at least an interferon such as a recombinant interferon, a granulocyte-macrophage colony-stimulating factor such as a recombinant granulocyte-macrophage colony-stimulating factor. In one embodiment, the recombinant interferon is a recombinant interferon-alfa (rIFN-α). In one embodiment, the granulocyte-macrophage colony-stimulating factor is a recombinant granulocyte-macrophage colony stimulating factor (rGM-CSF).

In one embodiment, the immunotherapeutic pharmaceutical composition comprises an immune enhancer comprising at least an interferon such as a recombinant interferon, a granulocyte-macrophage colony-stimulating factor such as a recombinant granulocyte-macrophage colony-stimulating factor.

In one embodiment of the immune enhancer, the ratio of the content of the recombinant interferon to the content of the recombinant granulocyte-macrophage colony-stimulating factor is (about $0.1 \times 10^4$ IU-about $5 \times 10^6$ IU) to (about 1 μg-about 200 μg), per dose. In another embodiment, the ratio of the content of the recombinant interferon to the content of the recombinant granulocyte-macrophage colony-stimulating factor is (about $0.5 \times 10^4$ IU-about $1 \times 10^5$ IU) to (about 5 μg-about 50 μg), per dose.

In one embodiment, the recombinant interferon of the immune enhancer is interferon alpha, such as interferon alpha-2a.

Preferably, the ratio of the content by weight of rIFN-α to the content of rGM-CSF is in the range of ($0.1 \times 10^4$ IU-$5 \times 10^6$ IU):(1 μg-200 μg), per dose.

More preferably, the ratio of the content of rIFN-α to the content of rGM-CSF is in the range of ($0.5 \times 10^4$ IU-$1 \times 10^5$ IU):(5 μg-150 μg), per dose.

More preferably, the ratio of the content of rIFN-α to the content of rGM-CSF is in the range of ($0.5 \times 10^4$ IU-$5 \times 10^4$ IU):(5 μg-50 μg), per dose.

Most preferably, the ratio of the content of rIFN-α to the content of rGM-CSF is in the range of $1 \times 10^4$ IU:10 μg, per dose.

In one preferred embodiment, the content of rGM-CSF is in the range of about 1 μg to about 100 μg, per dose; preferably in the range of about 5 μg to about 50 μg, per dose; more preferably in the range of about 5 μg to about 20 μg, per dose; and most preferably about 10 μg, per dose.

In another preferred embodiment, the content of rIFN-α is in the range of $1 \times 10^3$ IU-$9 \times 10^6$ IU, per dose, preferably in range of $5 \times 10^3$ IU-$5 \times 10^5$ IU, per dose, more preferably in the range of $8 \times 10^3$ IU-$2 \times 10^5$ IU, per dose, and most preferably in the range of about $0.5 \times 10^4$ IU-$1 \times 10^5$ IU, such as $1 \times 10^4$ IU, per dose. In another preferred embodiment, the above-mentioned immune enhancer may further include an aluminum adjuvant, such as aluminum hydroxide and/or aluminum phosphate.

In one example, the amount of aluminum adjuvant is in the range of about 0.5 mg-about 10 mg, per dose; preferably in range of about 1 mg-about 3 mg, per dose; more preferably in the range of about 1.25 mg-about 2.5 mg, per dose. In another example, the amount of aluminum adjuvant is in the range of about 0.1 mg-about 3 mg, per dose; preferably in the range of about 0.8 mg-about 2 mg, per dose; most preferably about 1.25 mg, per dose. In yet another example, the amount of aluminum adjuvant is in the range of about 0.01 mg-about 3 mg, per dose; preferably in the range of about 0.05 mg-about 2 mg, per dose; most preferably in the range of about 0.1 mg-about 0.5 mg, per dose, such as about 0.125 mg, per dose.

In one example, the weight ratio of aluminum adjuvant to rGM-CSF is in the range of (about 0.01 mg to about 1 mg):(about 1 μg to about 200 μg), per dose; preferably in the range of (about 0.05 mg to about 0.5 mg):(about 5 μg to about 150 μg), per dose; more preferably the ratio is in the range of (about 0.1 mg-about 0.25 mg):(about 5 μg-about 50 μg), per dose; most preferably, the weight ratio is about 0.125 mg:about 10 μg, per dose. In another example, the weight ratio of aluminum adjuvant to rGM-CSF is in the range of (about 0.1 mg to about 10 mg):(about 1 μg to about 300 μg), per dose; preferably in the range of (about 0.5 mg to about 5 mg):(about 2 μg to about 200 μg), per dose; more preferably the weight ratio is in the range of (about 1.5 mg to about 3 mg):(about 5 μg to about 100 μg), per dose; most preferably, the weight ratio is in the range of (about 1 mg to about 2 mg):(about 10 μg to about 75 μg), per dose.

In one embodiment, the immunotherapeutic pharmaceutical composition comprises at least an antigen such as a protein antigen (more preferably a recombinant protein antigen) and an immune enhancer as discussed above. In one embodiment, the recombinant interferon is interferon alpha-2a. In one embodiment, the antigen comprises or is a recombinant protein antigen. In one embodiment of the immunotherapeutic pharmaceutical composition, the ratio of the content of the recombinant interferon to the content of the recombinant granulocyte-macrophage colony-stimulating factor is (about $0.5×10^4$ IU-about $1×10^5$ IU) to (about 5 μg-about 20 μg), per dose. In another embodiment, the ratio of the content of the recombinant interferon to the content of the recombinant granulocyte-macrophage colony-stimulating factor is about $1×10^4$ IU to about 10 μg, per dose.

In one embodiment, the recombinant protein antigen is at least one of a viral antigen, a bacterial antigen, a fungal antigen, a parasite antigen, and a tumor antigen. In one embodiment, the viral antigen is at least one of HBV antigens, herpesvirus antigens, HPV antigens, HIV antigens, Merkel cell virus antigens, influenza antigens and RSV antigens. In one embodiment, the recombinant protein antigen is an inactivated vaccine antigen, an attenuated vaccine antigen or a subunit vaccine antigen.

In one embodiment, the recombinant protein antigen is a genetically engineered recombinant antigen.

In one embodiment, the immunotherapeutic pharmaceutical composition further comprises at least an adjuvant. In one embodiment, the adjuvant is an alum adjuvant such as an alum hydroxide.

In one embodiment, the immunotherapeutic pharmaceutical composition further comprises pharmaceutically or immunologically acceptable carriers or excipients.

In one embodiment, the immunotherapeutic pharmaceutical composition further comprises a hepatitis B antigen. In one embodiment, a safe and therapeutically effective amount of the Immune enhancer may be administered to a subject either before the administration of the antigen or during the administration (e.g., co-administration) of the antigen(s) to the subject. In one embodiment, a safe and therapeutically effective amount of the Immune enhancer is administered to a subject before the administration of the antigen to the subject. In another embodiment, a safe and therapeutically effective amount of the Immune enhancer is administered to a subject during the administration (e.g., co-administration) of the antigen(s) to the subject.

In one embodiment, the hepatitis B antigen is a recombinant hepatitis B antigen such as a recombinant hepatitis B surface antigen.

In one embodiment, the recombinant protein antigen is at least one of a viral antigen, a bacterial antigen, a fungal antigen, a parasite antigen, and a tumor antigen.

In one embodiment, the viral antigen is at least one of HBV antigens, herpesvirus antigens, HPV antigens, HIV antigens, Merkel cell virus antigens, influenza antigens and RSV antigens.

In another embodiment, the recombinant protein antigen is an inactivated vaccine antigen, an attenuated vaccine antigen or a subunit vaccine antigen. In one preferred embodiment, the recombinant protein antigen is a genetically engineered recombinant antigen.

In one embodiment, the immunotherapeutic pharmaceutical composition of the invention comprises at least an interferon such as a recombinant interferon, a granulocyte-macrophage colony-stimulating factor such as a recombinant granulocyte-macrophage colony-stimulating factor, an adjuvant such as an alum adjuvant and a an antigen such as a protein antigen (more preferably a recombinant protein antigen). In one embodiment, the adjuvant is an alum adjuvant such as an alum hydroxide. In one embodiment, the recombinant interferon is interferon alpha, such as interferon alpha-2a.

In one embodiment, the recombinant protein antigen is at least one of a viral antigen, a bacterial antigen, a fungal antigen, a parasite antigen, and a tumor antigen. In one embodiment, the viral antigen is at least one of HBV antigens, herpesvirus antigens, HPV antigens, HIV antigens, Merkel cell virus antigens, influenza antigens and RSV antigens. In one embodiment, the recombinant protein antigen is an inactivated vaccine antigen, an attenuated vaccine antigen or a subunit vaccine antigen. In one preferred embodiment, the recombinant protein antigen is a hepatitis B antigen such as a recombinant hepatitis B antigen, preferably a recombinant hepatitis B surface antigen.

In one preferred embodiment, the immunotherapeutic pharmaceutical composition of the invention comprises a rIFN-α, a rGM-CSF, an alum adjuvant, and a recombinant hepatitis B surface antigen after being mixed according to a certain proportion and in a certain sequence.

In one embodiment, the immunotherapeutic pharmaceutical composition of the invention is useful for the treatment of hepatitis B and is particularly suitable for the treatment of chronic hepatitis B in which the immune enhancer comprises a rIFN-α and a rGM-CSF, the adjuvant is an alum hydroxide. In one embodiment, a protein antigen or vaccine combination with rIFN-α and rGM-CSF at an optimal ratio is prepared into a pharmaceutical formulation. In one embodiment, the ratio of the content of rIFN-α to the content of rGM-CSF is (about $0.1×10^4$ IU-about $5×10^6$ IU) to (about 1 μg-about 200 μg), per dose, preferably (about $0.5×10^4$ IU-about $1×10^5$ IU) to (about 5 μg-about 50 μg), more preferably about $1×10^4$ IU to about 10 μg, per dose.

In one embodiment, the ratio of the content of rIFN-α to the content of rGM-CSF is in the range of (about $0.5×10^4$ IU to about $1.5×10^4$ IU):(about 5 μg to about 20 μg), per dose; preferably the ratio is about $1×10^4$ IU:about 10 μg, per dose. In the above-mentioned immunotherapeutic pharmaceutical compositions, the content of rGM-CSF is in the range of about 1 μg to about 200 μg, per dose; preferably from about 5 μg to about 50 μg, per dose; more preferably from about 5 μg to about 20 μg, per dose; and most preferably from about 10 μg, per dose.

In the above-mentioned immunotherapeutic pharmaceutical compositions, the content of the rIFN-α is in the range of about $1×10^3$ IU to about $9×10^5$ IU, per dose; preferably about $5×10^3$ IU to about $1×10^5$ IU, per dose; more preferably about $8×10^3$ IU to about $5×10^4$ IU, per dose; most preferably about $1×10^4$ to about $2×10^4$ IU, such as about $1×10^4$ IU, per dose.

In the above-mentioned immunotherapeutic pharmaceutical composition, the content ratio of antigen to rGM-CSF is in the range of (about 0.1 μg-about 10 μg):(about 1 μg-about 100 μg), per dose; preferably (about 0.5 μg-about 5 μg):(about 5 μg-about 50 μg), per dose; more preferably (about 1 μg to about 5 μg):(about 5 μg to about 25 μg), per dose; most preferably about 1 μg:about 10 μg, per dose.

In one embodiment, the composition in the pharmaceutical preparation or the formulation is injected into the body through the traditional injection methods such as subcutaneous, muscle, mucosal and other parts of the body, and also can be administered by nasal drops, eye drops and dermal deliveries. After administration, the monocytes are effectively differentiated into immature DC and then converted to mature DC cells, thereby enhancing the efficiency of antigen presentation to effectively elicit host immunity to break the virus-induced immune tolerance, and clear of the viruses hidden in body; have a strong antibody and cellular immune responses to prevent the recurrence of the virus infection, and even remove the virus from the body, and prevent HBV re-infection.

In the invention, the antigen may be derived from microorganisms, such as viruses, bacteria, fungi, parasites and the like.

In one embodiment, the antigen in the immunotherapy pharmaceutical composition includes the protein antigen.

Preferably, the protein antigen is at least one of the virus antigens, bacterial antigens, fungal antigens, parasitic antigens and tumor antigens.

More preferably, the above-mentioned viral antigens include at least one of HBV antigens, herpes virus antigens, HPV antigens, HIV antigens, Merkel cell virus, influenza virus antigens and RSV antigens.

In another embodiment, the above-mentioned protein antigens are inactivated vaccine antigens, attenuated vaccine antigens or subunit vaccine antigens.

In another embodiment, the protein antigen is a genetic engineering vaccine antigen.

In one preferred embodiment, the protein antigen is a recombinant protein antigen, such as a hepatitis B antigen, preferably a recombinant hepatitis B antigen, more preferably a recombinant hepatitis B surface antigen.

In one embodiment, the viral antigen may be serum derived hepatitis B virus surface antigen or genetic engineered hepatitis B surface protein and expressed in yeast and CHO cells. In one embodiment, the hepatitis B subunit antigens are prepared by genetic engineering to express in yeast systems or in mammalian cells, extracted, purified and combined with adjuvants.

The viral antigens may be derived from the herpes virus, the HPV, the HIV, Merkel cell virus, the influenza virus, the RSV or each family of viruses including, but not limited to, Adenoviridae, Arenaviridae, Bradyviridae, Caliciviridae, Coronaviridae, Filoviridae, Hepadnaviridae, Herpesviridae, Orthomyxoviridae, Orthomyxoviridae, Papovaviridae, Paramyxoviridae, Parvoviridae, Picornaviridae, Poxviridae, Reoviridae Reoviridae, Retroviridae, Rhabdoviridae or Togaviridae. They also include microorganisms that cause animal diseases such as PRRSV, PCV, FMDV, Rabies virus, parovirus, distemper virus, adenovirus, coronavirus, parainfluenza virus, *Bordetella* and Leptospira bacteria.

The tumor antigens may be derived from the following tumors: oral cancer, esophageal cancer, stomach cancer, duodenal cancer, small intestine cancer, colon cancer, anal cancer, liver cancer, pancreatic cancer, gall bladder cancer, cholangiocarcinoma, Cancer, lung cancer, skin cancer (melanoma), bone cancer, myeloma, T and B cell lymphoma, leukemia, Hodgkin's tumor, non-Hodgkin's tumor, Kaposi's sarcoma, head and neck neoplasm, brain thyroid, glioma, thyroid, thymus, renal, ureteral, bladder, testicular, prostate, penile, uterine, cervical, ovarian, fallopian, Vaginal.

In one embodiment, the animal virus antigens are mainly derived from animal vaccines such as inactivated vaccines, attenuated vaccines and subunit vaccines.

In one embodiment, the antigen may be tumor-derived specific and related antigen.

In another aspect, the disclosure reveals a method for preparing the immunotherapeutic pharmaceutical composition as discussed herein, wherein the method comprises the steps of: mixing the antigen, the recombinant interferon, the granulocyte-macrophage colony-stimulating factor, and the pharmaceutically or immunologically acceptable carriers or excipients under aseptic conditions to produce the immunotherapeutic pharmaceutical composition.

In another aspect, the invention provides the use and preparation method of immunotherapeutic pharmaceutical compositions as discussed herein as a therapeutic vaccine adjuvant and a vaccine composition. Applicants use a recombinant hepatitis B surface antigen as an example for demonstration purpose. The technicians of this field in concrete implement process can substitute it with any vaccines in the existing technology, such as hepatitis B subunit vaccines prepared from recombinant rHBsAg antigens in the present invention.

In one embodiment, the use of the immunotherapeutic pharmaceutical compositions of claim 5 in the preparation of immunotherapeutic drugs, the use comprising: 1) promoting monocytes production; 2) promoting expression of monocyte CCR2; 3) promoting differentiation of Ly6C$^{hi}$CCR2$^+$ monocytes into DCs with phenotype CD11 b$^+$ CD11c$^+$; 4) improving the cellular immunity and CTL cytolytic functions of a subject; 5) promoting the humoral immunity of the subject and production of one or several protective antibodies.

In one embodiment, the use comprises preventing or treating one or more of viral infections, bacterial infections, fungal infections, parasitic infections, and tumors. In one embodiment, the viral infections comprise one or more of human hepatitis virus infection, herpes virus infection, human papilloma virus infection, human immunodeficiency virus infection, Merkel cell virus infection, influenza virus infection and respiratory syncytium virus infection.

In one embodiment, the antigen is a hepatitis B vaccine and the immunotherapeutic pharmaceutical composition can break down the immune tolerance and eliminate infected hepatocytes, HBeAg and HBsAg, while generating anti-HBs Ab. In one embodiment, the antigen is a tumor antigen and the immunotherapeutic pharmaceutical composition induces an anti-tumor immune response. In another embodiment, the tumor antigen comprises at least one of a prostate cancer antigen polypeptide or epitopic peptide, a breast cancer antigen polypeptide or epitopic peptide, a colorectal cancer antigen polypeptide or epitopic peptide, a cervical cancer polypeptide or epitopic peptide, a liver cancer polypeptide or epitopic peptide, multiple myeloma polypeptide or epitopic peptide, and renal cell carcinoma polypeptide or epitopic peptide.

In one embodiment, the antigen is one of the streptococcal antigens and the immunotherapeutic pharmaceutical composition induces an immune response that produces an antibacterial infection. In one embodiment, the streptococcal antigen is a modified *Streptococcus* Type A epitope peptide.

In one embodiment, the antigen is one of HIV antigens and the immunotherapeutic pharmaceutical composition induces an immune response that produces an anti-HIV infection. In one embodiment, the HIV antigen is an HIV epitope peptide.

In one embodiment, the antigen is one of Merkel cell viral antigens and the immunotherapeutic pharmaceutical composition induces an immune response that produces an anti-Merkel cell viral infection. In one embodiment, the Merkel cell viral antigen is one of the Merkel cell polypeptides.

In one embodiment, the use comprises administration of a safe and therapeutically effective amount of the immunotherapeutic pharmaceutical composition to a subject to be immunized. In one embodiment, the subject is a mammal.

In one embodiment, Applicants have experimentally confirmed that the amount of the GM-CSF in the range of about 1 μg-about 200 μg per dose is effective, preferably in the range of about 20 μg-about 150 μg per dose, and more preferably in the range of about 50 μg-about 100 μg per dose.

In one embodiment, Applicants have experimentally confirmed that the activity of IFN-α in the range of about 1000 IU to about 50,000 (IU) units is effective, preferably in the range of about 2000 IU to about 30,000 (IU) per dose, more preferably in the range of about 5000 IU to about 20000 (IU).

The invention adopted the following technical embodiments. The recombinant human interferon-a is expressed in *Escherichia coli* or yeast system through genetic engineering technologies, extracted, purified and combined with excipients to make ready to use rhIFN-α (type I interferon). The recombinant human GM-CSF is expressed in *Escherichia coli* or yeast system through genetic engineering technologies, extracted, purified and combined with excipients to make the read to use rhGM-CSF (recombinant human granulocyte macrophage colony stimulating factor). Human hepatitis B surface antigen is expressed in yeast system or CHO cell by genetic engineering technologies, extracted and purified and make the read to use rHBsAg (recombinant hepatitis B surface antigen).

rhIFN-α, rhGM-CSF, and antigens in the compositions of the present invention can be prepared by conventional methods in this field or are commercially available.

In one embodiment of the composition of the present invention, the mass ratio of the rHBsAg to the rhGM-CSF is about 1:(1-100), preferably 1:(1-80); more preferably 1:(1-30) (e.g., 1:7.5). The ratio of rhGM-CSF to rhIFN-α and/or aluminum adjuvant is as described above.

Immune Enhancers

Immune enhancers, also known as adjuvants and non-specific immune enhancers, are not antigenicity and are pre- or concurrently acting with antigens. They nonspecifically alter or enhance the specific immune response to antigens, which either together with the antigen (e.g., co-administration) or previously injected prior to the administration of the antigen to enhance the immunogenicity or change the type of immune responses. In addition to traditional aluminum adjuvants, substances such as cytokines can also be important adjuvants. For example, the GM-CSF is a multi-potential hematopoietic cell growth factor that not only promotes the proliferation, differentiation, and maturation of hematopoietic progenitor cells but also stimulates other cells such as APCs, fibroblasts, keratinocytes and skin mucous cells.

Applicants found in the preliminary experiments that the combination of hepatitis B vaccine with GM-CSF can enhance the immune response in mammals, but the enhancement is limited. Further, Applicants found that pre-injection of GM-CSF once a day for three times and then injection with vaccine antigen at the same site, the level of immune response, especially T-cell response, would be greatly improved. The mechanism was also studied in depth. It was found that pre-injection of GM-CSF mainly improves the enrichment and transformation of monocytes to increase the number of antigen-presenting cells (DCs), ability and viability of DCs antigen presentation. DCs could effectively present antigen to T cells when exposed to the antigen, thus enhancing the response of cellular immunity. This study indicated that different administration strategies of GM-CSF and vaccine antigen can produce different immune effects. However, this method is very inconvenient to use clinically. In fact, the protocol of 3-day pre-injections of GM-CSF before injection of a vaccine has not been easy to implement for patients and nurses who handled injections. It was found that there are 3 main disadvantages: 1) this method brings a great inconvenience to vaccinate into patients and achieve a consistent result, which was due to the multiple number of injections employed and not the same location been injected each time in clinical trials, 2) due to the above fact, poor patient compliances and drop out of trials has associated the inconvenient protocol, 3) patients need to stay in the hospital for multiple days before they can complete one round of injections. Considering these disadvantages, the 3-day pre-treatments should be urgently improved.

IFN-α at higher dose administrations not only can inhibit the replication of viruses through alarm adjacent cells to produce antiviral proteins, thereby clearing viral infections, but also can enhance natural killer cells (NK cells), monocytes, macrophages and T lymphocytes activity, which play an immunomodulatory role and enhance anti-viral responses.

IFN-α has been shown to drive dendritic cells to differentiation and enhance dendritic cell cross-presentation (J. Immunol. Apr. 1, 2012 188:3116-3126; Blood Feb. 9, 2012 119:1407-1417). IFN-α and GM-CSF administered together could differentiate peripheral blood monocytes into potent antigen presenting cells in vitro system at certain concentrations (Journal of Leukocyte Biology 1998, 64:358-367). However, it has not been previously examined whether the IFN-α and GM-CSF with a protein antigen together at an invented optimal dose ratio can provide enhanced immune responses in vivo. It particularly remains unknown whether the enhanced immune responses can be mediated via activation of the differentiating $Ly6C^{hi}CCR2^+$ monocytes and potentiation them into $CD11b^+CD11c^+$ dendritic cells. The differentiation of $Ly6C^{hi}CCR2^+$ monocytes into $CD11b^+CD11c^+$ dendritic cells is very important to potential cell mediated immunity since other types of monocytes, such as the $Ly6C^-$ monocytes.

These two major types of monocytes have been reported in mice and humans (Immunity 2003, 19, 71-82). The most notable distinction is between inflammatory monocytes expressing high level of Ly6C, and monocytes that lack Ly6C. The immunotherapeutic pharmaceutic compositions at optimal formulation described in this invention could induce high level of $Ly6C^{hi}CCR2^+$ monocytes and lead to therapeutic effects subsequently.

Combination

The invention provides immunotherapeutic pharmaceutical compositions.

The immunotherapeutic pharmaceutical compositions of the invention include a pharmaceutically acceptable carrier and an effective amount of the active ingredient.

As used herein, the term "therapeutically effective amount" or "therapeutically effective dose" refers to an amount that is functional or active in humans and/or animals and acceptable to humans and/or animals.

As used herein, the term a "pharmaceutically acceptable carrier," refers to a substance which has a reasonable benefit/risk ratio applicable to humans and/or mammals without undue adverse effects such as toxicity, irritation, and allergy. The term "pharmaceutically acceptable carrier" refers to a carrier to assist administration of a therapeutic agent and it includes various excipients and diluents.

The immunotherapeutic pharmaceutical compositions of the invention comprises a safe and therapeutically effective amount of active ingredients and pharmaceutically acceptable carriers. Such carriers may include, but are not limited to, saline, buffer, dextrose, glycerol, mannitol, trehalose, cyclodextrin, aluminum adjuvant, urea and combinations thereof. Generally, the pharmaceutical preparation should be matched with the mode of administration. The immunotherapeutic pharmaceutical compositions of the present invention can be in the form of injections, oral preparations (tablets, capsules, oral liquid), transdermal agents and sustained-release agents. For example, by a conventional method the compositions may include physiological saline or an aqueous solution containing glucose and other adjuvants. The immunotherapeutic pharmaceutical composition is preferably manufactured under aseptic conditions.

The therapeutically effective amount of active ingredient of the invention may vary depending on the mode of administration and the severity of the disease to be treated. The preferred therapeutically effective amount can be selected by general technical persons in this field based on a variety of factors (e.g., through clinical trials). Such factors may include, but are not limited to, the pharmacokinetic parameters of the active ingredient such as bioavailability, metabolism, half-life; the severity of the disease, the patient's body weight, the patient's immune status, the administration and so on. In general, a satisfactory effect is obtained when the active ingredient is administered daily at a dose of about 0.00001 mg/kg to about 50 mg/kg, preferably about 0.0001 mg to about 10 mg/kg. For example, depending on the urgency of the treatment condition, several divided doses may be administered weekly, or the dose may be proportionally reduced.

Pharmaceutically acceptable carriers of the invention may include, but are not limited to saline, dextrose, glycerol, mannitol, trehalose, cyclodextrin, aluminum adjuvant, urea, liposomes, lipids, oil, proteins, protein-antibody conjugates, peptides, cellulose, nanoparticled, nanogels, and other combinations. The carriers should be matched to the mode of administration, all as is well-known to the general technicians in this field.

The invention also provides the use of the pharmaceutical composition for the prevention and/or treatment of diseases including microbial infections and persistent infections (such as viral infections) or tumors.

Vaccine Composition

The vaccine compositions of the invention may be prophylactic (prevent infection) and may also be therapeutic. The vaccine composition comprises immunogenic antigen(s) (such as protein antigen) and is combined with "pharmaceutically acceptable carrier(s)" which does not induce carrier-specific antibodies. Suitable carriers are typically large, slowly metabolized macromolecules such as aluminum hydroxide, dextrose, mannitol, trehalose, cyclodextrin, carrier proteins, polysaccharides, polylactic acid, polyglycolic acid, amino acid polymers, amino acid copolymers, lipid aggregates such as oil droplets or liposomes and/or any combinations of them. These vectors are well known to the general technical persons in this field. In addition, these vectors function as immunostimulants ("adjuvants"). Antigens can also be conjugated to bacterial toxins (toxoids such as diphtheria, tetanus, cholera, diphtheria $CRM_{197}$) or carrier proteins (L1 from HPV16 or HPV18, VP1 from Merkel's cell virus, Ovalbumin, keyhole limpet hemocyanin). In addition to the above-mentioned immunostimulants of the invention, other adjuvants that enhance the effect of the immunogenic composition may also be added to the vaccine composition may include, but not limited to: (1) alum, such as aluminum hydroxide, aluminum phosphate, Aluminum sulfate and the like; (2) oil-in-water emulsion formulations such as (a) MF59 (see WO90/14837), (b) SAF, and (c) Ribi™ Adjuvant System (RAS); (3) Freund complete adjuvant (CFA) and Freund's incomplete adjuvant (IFA); (4) TLR agonists, eg. CpG, MPL, poly I:C, Pam3Cys, flagellin, resiquimod; (5) cytokines such as interleukins (such as IL-1, IL-2 and IL-4, IL-5, IL-6, IL-7, IL-12 and the like), tumor necrosis factor (TNF) and the like; (5) bacterial ADP-ribosylating toxins detoxification variants such as cholera toxin CT, pertussis toxin PT or E. coli Heat-labile toxin LT, for example WO 93/13302 and WO 92/19265; and (6) other substances that enhance the effectiveness of the composition.

In one embodiment, Vaccine compositions include immunogenic compositions such as antigens, pharmaceutically acceptable carriers, and adjuvants, typically contain diluents such as water, saline, glycerol, buffer, and the like. In addition, auxiliary substances such as wetting, emulsifying agents, pH buffering substances and the like may also be included.

More specifically, vaccines, including immunogenic compositions, contain an immunologically effective amount of an immunogenic polypeptide, as well as the other desired components described above. An "immunologically effective amount" means that the amount administered to a subject as a single dose or as part of a continuous dosages is effective for treatment or prophylaxis. The amount can vary depending on the health and physiology of the individual, the type of individual (e.g., human), the ability of the individual's immune system to produce antibodies, the degree of protection desired, the formulation of the vaccine, the medical physician's assessment of medical condition, and other related factors. It is expected that this amount will be within a relatively wide range and can be determined by routine experimentation.

Generally, the vaccine composition or the immunogenic composition can be formulated as an injection, for example as a liquid solution or suspension; it can also be produced as a solid form suitable for preparation as a solution or suspension before injection. The formulation can also be emulsified or encapsulated in liposomes to enhance the adjuvant effect.

In addition, the vaccine composition of the present invention may be monovalent or multivalent.

Routes of Administration and Dosage

The composition can be administered directly to a subject. The subject may be a human or non-human mammal, preferably a human. When used as a vaccine, the composition of the invention can be administered directly to the individual using any known methods. These vaccines are usually administered using the same routes as used by conventional vaccines and/or mimicking the pathogen's infection.

Routes of administration of the pharmaceutical composition or vaccine composition of the invention may include, but are not limited to, intramuscular, subcutaneous, intradermal, intrapulmonary, intravenous, intranasal, vaginal, oral or other parenteral routes of administration. If desired, the route of administration may be combined or adjusted according to the condition of the disease. Vaccine compositions can be administered in a single dose or in multiple doses and can include the administration of booster doses to elicit and/or maintain immunity.

The vaccine should be given in a "therapeutically effective amount," that is, the amount of vaccine is sufficient to elicit an immune response in the chosen route of administration and can effectively promote the protection of the host against viral infections.

The amount of antigen selected for each dose is based on the amount that would trigger a protective response without significant side effects. Generally, after infection of the host cell, each dose contains the protein antigen from about 0.1 μg to about 10000 μg, preferably about 1 μg to about 100 μg, and more preferably about 10 μg to about 50 μg. Antibody titers and other reactions in the subject can be used as standard methods to determine the optimal dosage for a particular vaccine. The level of immunity can be used to determine if a booster dose is needed. After assessing antibody titers in serum or T cell functions of PBMC, booster doses may be required. Administration of an adjuvant and/or an immunostimulant may increase the immune responses to antigens of the invention. The preferred method is to administer the immunogenic composition by injection from the subcutaneous or intramuscular route.

The invention is further described below with reference to specific examples. It should be understood that these examples are only used for illustrating the invention and are not intended to limit the scope of the invention. The following examples did not indicate the specific conditions of the experimental methods, usually in accordance with conventional conditions, such as those described in Sambrook et al., Molecular Cloning: A Laboratory Manual (New York: Cold Spring Harbor Laboratory Press, 1989), or manufacturer's recommended conditions. Unless otherwise indicated, percentages and parts are referred by weight.

Materials and Methods

1. Laboratory Animals and Cell Lines

Six- to eight-week-old C57BL/6 male mice were purchased from Huafukang Laboratory Animal Co. Ltd (Beijing, China). All mice were housed in environmentally-controlled conditions. Five mice were in one cage, with independent ventilation in each cage. All procedures were performed with the institutional animal use and care committee approval.

DC2.4 cells are C57BL/6 bone marrow-derived dendritic cells.

2. The Main Reagent

The main reagents used in the examples of the invention are shown in Table 1.

TABLE 1

| Name | Catalog | Size | Manufacturer |
| --- | --- | --- | --- |
| Human interferon alpha-2b | S20030030 | 500 million IU | Beijing Kawin Technology Share-Holding Co., Ltd. |
| Human granulocyte-macrophage colony-stimulating factor | S19980020 | 150 μg | North China Pharmaceutical Gin Tan Biotechnology Co., Ltd. |
| Recombinant Hepatitis B Vaccine (CHO) | S20113004 | 10 μg | North China Pharmaceutical Gin Tan Biotechnology Co., Ltd. |
| Hematological HBsAg | GK-001 | 1 mg/mL | Shanghai Gui Kang Biological Technology Co., Ltd. |
| HBsAb ELISA standards | GBW(E)090187 | 80 mIU/mL | Beijing Kinghawk Pharmaceutical Co., Ltd |
| HBsAg ELISA standards | GBW(E)090174 | 2 IU/mL | Beijing Kinghawk Pharmaceutical Co., Ltd |
| Mouse interferon alpha | 50525-M01H | 10 μg | Sino Biological Inc. |
| Mouse IL-4 | 111249 | 10 μg | Peprotech |
| Mouse GM-CSF | 021455 | 10 μg | Peprotech |
| HRP-labeled goat anti-mouse IgG1 | 1071-05 | 1 mL | Southern Biotech |
| HRP-labeled goat anti-mouse IgG2a | 1081-05 | 1 mL | Southern Biotech |

TABLE 1-continued

| Name | Catalog | Size | Manufacturer |
| --- | --- | --- | --- |
| Hepatitis B surface antigen CTL epitope peptide | $S_{208-215}$: ILSPFLPL | Purity 95% | Shanghai Science Peptide Biological Technology Co., Ltd. |
| Chicken Ovalbumin CTL epitope peptide | $O_{257-264}$: SIINFEKL | Purity 95% | Shanghai Science Peptide Biological Technology Co., Ltd. |
| DMEM medium | 12491-015 | 500 mL | Gibco |
| RPMI1640 medium | 11875-093 | 500 mL | Gibco |
| Fetal bovine serum | 10100-147 | 500 mL | Gibco |
| Penicillin + Streptomycin | BL505A | 100 mL | Nanjing Wo Hong Technology Co., Ltd. |
| Phorbol ester | P1585 | 1 mg | Sigma |
| Ionomycin | 10634 | 10634 | Sigma |
| Brefeldin A (1000×) | 420601 | 420601 | BioLegend |
| CD8 T cell sorting kit | 480008 | 100 test | BioLegend |
| Mouse monocyte enrichment kit | 19761 | $10^9$ cells | Stemcell |
| Phosphate buffer | SH30256.01 | 500 mL | Hyclone |
| Serum-free cell cryopreservation solution | C40100 | 100 mL | Suzhou Saimei Biotechnology Co., Ltd. |
| 4% paraformaldehyde | G1101 | 500 mL | Wuhan Guge Biotechnology Co., Ltd. |
| Murine MCP-1 ELISA Assay Kit | 88-7391-22 | 2 × 96 test | eBioscience |
| Murine IL12p70 ELISA Assay Kit | BMS6004 | 96 test | eBioscience |
| Anti-Mouse CD3 Functional Grade Purified | 16-0032-85 | 500 μg | eBioscience |
| Anti-Mouse CD28 Functional Grade Purified | 16-0281-85 | 500 μg | eBioscience |
| Permeabilization Buffer (10X) | 00-8333-56 | 100 mL | eBioscience |
| CFSE | 65-0850 | 500 μg | eBioscience |
| CCR2 inhibitors (INCB 3344) | HY50674 | 30 mg | Medchemexpress |

3. Antibodies

The antibodies used in the examples of the invention are shown in Table 2.

TABLE 2

| Name | Clone | Isotype | Manufacturer |
| --- | --- | --- | --- |
| APC/Cy7 Anti-mouse CD3 | 17A2 | Rat IgG2b, κ | BioLegend |
| PE/Cy7 Anti-mouse CD4 | RM4-5 | Rat IgG2a, κ | BioLegend |
| FITC Anti-mouse CD8 | 53-6.7 | Rat IgG2a, κ | eBioscience |
| APC Anti-mouse IFN-γ | XMG1.2 | Rat IgG1, κ | BioLegend |
| Brilliant Violet 421 ™ Anti-mouse IL-4 | 11B11 | Rat IgG1, κ | BioLegend |
| PE Anti-mouse IL-17A | TC11-18H10.1 | Rat IgG1, κ | BioLegend |
| Brilliant Violet 421 ™ Anti-mouse CD11b | M1/70 | Rat IgG2b, κ | BioLegend |
| FITC Anti-mouse CD11c | HL3 | Hamater IgG | BD |
| PE Anti-mouse Ly6G | RB6-8C5 | Rat IgG2b, κ | eBioscience |
| FITC Anti-mouse Ly6C | HK1.4 | | BioLegend |
| Alexa Fluor ® 647 Anti-mouse CCR2 | SA203G11 | Rat IgG2b, κ | BioLegend |
| FITC Anti-mouse F4/80 | BM8 | Rat IgG2a, κ | eBioscience |
| APC Anti-mouse CD80 | 16-10A1 | Hamater IgG | eBioscience |
| Brilliant Violet 510 ™ Anti-mouse CD86 | GL-1 | Rat IgG2b, κ | BioLegend |

TABLE 2-continued

| Name | Clone | Isotype | Manufacturer |
| --- | --- | --- | --- |
| PE Anti-mouse MHC-I | AF6.88.5.5.3 | Rat IgG2b, κ | eBioscience |
| eVolve ™ 655 Anti-mouse MHCII | M5/114.15.2 | Rat IgG2b, κ | eBioscience |
| PE Anti-mouse IL-12 | C17.8 | Rat IgG2a, κ | eBioscience |
| PE Anti-mouse PDCA-1 | eBio927 | Rat IgG2b, κ | eBioscience |
| PE Anti-mouse Ki67 | SolA15 | Rat IgG2a, κ | eBioscience |

4. Animal Groups and Immunization Strategies are Shown in Table 3.

TABLE 3

| Gourp (n = 5) | Dose proportion |
| --- | --- |
| ① PBS | — |
| ② GM-CSF | 10 μg |
| ③ IFN-α | 10000 IU |
| ④ VACCINE | 1 μg |
| ⑤ GM-CSF/IFN-α | 10 μg/10000 IU |
| ⑥ GM-CSF/VACCINE | 10 μg/1 μg |
| ⑦ IFN-α/VACCINE | 10000 IU/1 μg |
| ⑧ GM-CSF/IFN-α/VACCINE | 10 μg/10000 IU/1 μg |
| ⑨ 3 × GM-CSF + VACCINE | 10 μg(one day one time, a total of three times) + 1 μg |

Notes: VACCINE is the CHO-recombinant Hepatitis B Vaccine or Yeast-recombinant Hepatitis B Vaccine in the Table 1. The amount of antigen in one dose of VACCINE is 1 ug and the amount of aluminum adjuvant is 0.125 mg (dose proportion of VACCINE is based on the total mass). The components of group ⑤, ⑥, ⑦, ⑧ were weighed and mixed especially, placed 4° C. for at least 2 hours until use.

5. Mouse Blood Collection and Serum Preparation

About 200 μL of blood was collected from the orbital sinus. The collected blood was incubated in a 37° C. for 40 min, centrifuged 3000 rpm at 4° C. for 30 min. The serum was collected, stored at −80° C. for use.

6. Specific Antibody Titers Detection by ELISA

Antigen was diluted to 2 μg/mL to coat plate overnight at 4° C. The mouse serum to be tested was diluted by ten folds gradient dilution, and 100 μl of diluted serum was added to each well and incubated at 37° C. for 1 h. 200 μl/well of secondary antibody incubation incubate at 37° C. for 1 h. TMB reaction at 37° C. for 15 min. According to the OD value of the sample, the titer of the antigen-specific IgG was calculated.

7. Delayed-Type Hypersensitivity (DTH) Test

Mice were subcutaneously injected with 100 μL of the corresponding drug. On the 7th day after the last immunization, the mouse footpad was injected with HBsAg (10 μg/10 μL) using a micro syringe and PBS 10 μL was injected into the right footpad as a control. After injection, the footpad thickness was measured at 24 h, 48 h and 72 h respectively using a vernier caliper. The same site was measured three times and averaged. DTH formula: DTH swelling thickness (mm)=left foot pad thickness (mm)-right foot pad thickness (mm).

8. Detection of Intracellular Cytokines by Flow Cytometry

Mouse spleen was aseptically removed and prepared to single cell suspension. The cells was adjusted to $1\times10^7$ cells/ml. HBsAg (final concentration of 10 μg/ml) was added to stimulate splenic cells at 37° C. for 18 h, blocked by Brefeldin A (BFA) for the last 6 h, phorbol ester (PMA) 100 ng/ml and ionomycin 1 μg/ml as positive control. The appropriate fluorescent antibody was added to the 50 μL staining system, the cell surface antibody stained for 30 min at 4° C., and then incubated the intracellular cytokine antibody for 1.5 h at 4° C. Detection with BD flow cytometry, the results were analyzed using FlowJo7.6 software.

9. T Cell Proliferation Assay by Carboxyfluorescein Diacetate Succinimidyl Ester (CFSE)

Mouse spleen was aseptically removed and prepared to single cell suspension. The cells was adjusted to $1\times10^7$ cells/ml. HBsAg (final concentration of 10 μg/ml) was added to stimulate splenic cells at 37° C. for 72 h, anti-CD3 and anti-CD28 (final concentration of 1 μg/mL, final concentration of 100 ng/mL) as positive control. Cells were stained with anti-CD3, anti-CD4 and anti-CD8. The proliferation of T cells was detected by flow cytometry. The results were analyzed by FlowJo 7.6 software.

10. DC2.4 Cell Test $1\times10^5$ cell/well of the DC2.4 cells were plated on a 6-well plate. Cells were stimulated by LPS (1 μg/mL), GM-CSF 1 μg/mL), IFN-α (100 IU/mL), GM-CSF/IFN-α respectively in 5% CO2 at 37° C. for 72 h, and Brefeldin A (BFA) was added for the last 6 h. After DCs were cultured for 72 h, the surface molecules CD11b, CD80, CD86, MHC-I, MHC-II and intracellular cytokine IL12 were stained and cells were detected by flow cytometry.

11. In Vitro Cytotoxic Lysis Assay

Mouse spleen was aseptically removed and prepared to single cell suspension. The effector cells were enriched by the CTL peptide of HBsAg (10 μg/mL) at 37° C. for 72 h. The target cells were stimulated by the CTL peptide of HBsAg (10 μg/mL) for 1 h. The ratio of the effecter cells to the target cell was 50:1. After reaction, the cells were stained by propidium iodide (PI) and detected by flow cytometry.

12. In Vivo Cytotoxic Lysis Assay

Splenocytes from naïve C57BL/6 donor mice were labeled with 15 mM of CFSE and pulsed with 1 mg/mL of S208-215 (defined as CFSEhigh target cells). An equal fraction of splenocytes were labeled with 1 mM of CFSE and pulsed with 1 mg/mL of OVA257-264 (defined as $CFSE_{low}$ target cells) as a non-HBV target control. A mixture of $CFSE_{high}$ and $CFSE_{low}$ cells at a 1:1 ratio was adoptively transferred intravenously into immunized recipients at $2\times10^7$ cells per mouse on the $14^{th}$ day after the fourth vaccination. 8 hours later, the splenocytes were isolated from the recipients and CFSE fluorescence intensities were analyzed.

13. Immunohistochemistry (IHC) Analysis

On day 14 after the fourth immunization, dissected liver samples were collected and fixed in 4% paraformaldehyde for 3 d before being embedded in paraffin wax, and cut into 5 to 10 mm thick slices. The liver sections were stained with hematoxylin-eosin for histology analysis and incubated with polyclonal rabbit antibody for IHC analysis.

14. Statistical Analysis

Statistical analysis was performed using Student's t-test and P values less than 0.05 were deemed significant.

Example 1

IFN-α/GM-CSF/VACCINE Induces Humoral and Cellular Immunity in Wild-Type Mice 1.1 The Optimal Dose Ratio of GM-CSF, IFN-α and VACCINE In order to determine an optimal dose ratio of GM-CSF, IFN-α, and VACCINE to achieve the same immune therapeutic effects as the 3×GM-CSF+VACCINE regimen, a various dose ratios of GM-CSF, IFN-α, and VACCINE were examined. We found that the number of CD11b$^+$CD11c$^+$ cells was significant higher in the dose ratio at 10 μg of GM-CSF and 10,000 IU of IFN-α mixed with 1 μg of VACCINE regimen compared with other ratios (FIG. 1A). We found that DTH responses induced by 10 μg of GM-CSF and 10,000 IU of IFN-α mixed with 1 μg of VACCINE reached the same level as the 3×GMCSF+VACCINE in animals, but significantly higher than other dose ratios (FIG. 1B). We also found that the highest level of anti-HBsAg was achieved by the GM-CSF/IFN-α/VACCINE regimen with such dose ratio compared with the 3×GM-CSF+VACCINE (FIG. 1C). These results demonstrate that regimen with GM-CSF at 10 μg, IFN-α at 10,000 IU and VACCINE at 1 μg is an optimal dose ratio.

Specifically, aged 6-8 weeks, male C57B/L6 mice are selected in the embodiment. For the first experiment, three doses of GM-CSF (10 μg, 20 μg, and 30 μg), three doses of IFN-α(100 IU, 1,000 IU, 10,000 IU) and HBV vaccine 1 μg were selected respectively, the three components were mixed and were immunized twice on days 0 and 14. Peripheral blood samples were collected on days 1, 2 and 3 after immunizations, and the changes of DCs were detected and analyzed. The levels of DTH and HBsAb were detected on day 21. The experimental results showed that the ratio of CD11b$^+$CD11c$^+$DCs and levels of DTH and anti-HBsAg responses in peripheral blood were significantly increased by the combination of GM-CSF at 10 μg and IFN-α at 10,000 IU and HBV vaccine at 1 μg (FIG. 1). The CTL response and anti-HBsAg antibody levels had the same phenomenon (data not show).

Figure 2:
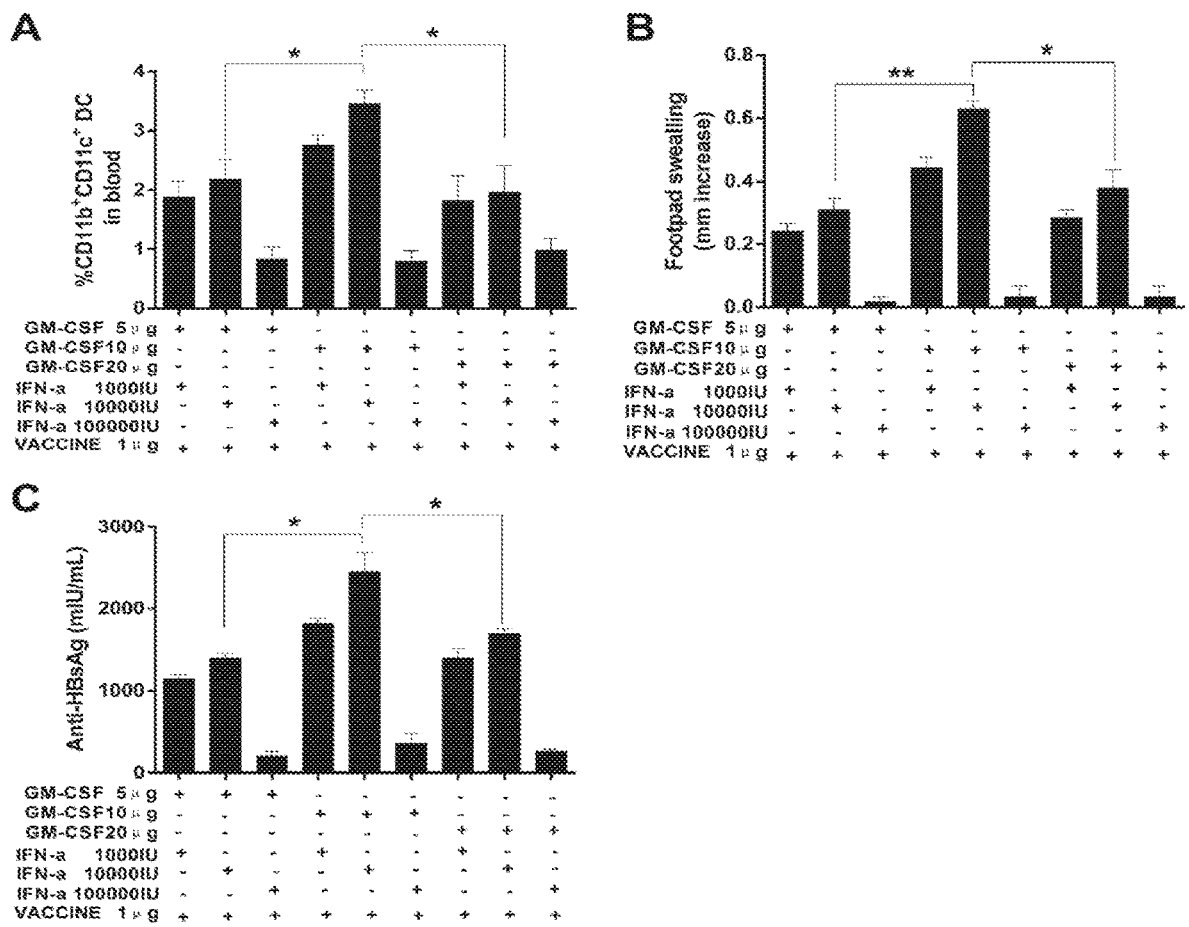
FIG. 2 is a set of graphs and images showing effects of different ratios and combinations by the use of immunotherapeutic pharmaceutical composition treatments. C57BL/6 mice were immunized with 5 μg, 10 μg, 20 μg GM-CSF combination with 1000 IU, 1 0000 IU, 10 0000 IU IFN-α respectively and 1 ug HBV vaccine.

The concentration of GM-CSF at 10 μg was the lowest selected for the previous experiment, GM-CSF at 5 μg was added to the second dose-finding experiment. Similarly, a higher dose of IFN-α at 100,0000 IU was added to the second dose-finding experiment. The results are shown in FIG. 2. The ratio of CD11b$^+$CD11c$^+$DCs and the levels of anti-HBsAg and the DTH responses by the combination of 5 μg GM-CSF with various doses of IFN-α were lower than those of GM-CSF at 10 μg combined with other doses of IFN-α. Surprisingly, the IFN-α at 100,000 IU combined with various doses of GM-CSF produced a significant inhibitory effects on the ratio of CD11b$^+$CD11c$^+$DCs and levels of DTH and anti-HBsAg than those at 10,000 IU or below of IFN-α. This result demonstrates that optimal dose ratio for GM-CSF is at 10 ug, and IFN-α is at 10,000 IU for mouse immunization.

1.2 Effects of Processing of Components on Immune Responses

Figure 3:
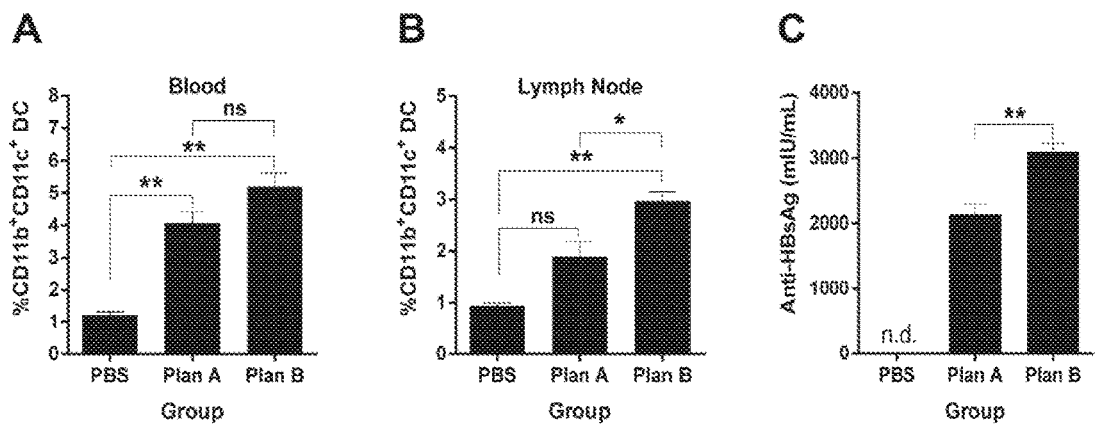
FIG. 3 is a set of graphs showing the changes of CD11b$^+$ CD11c$^+$ DCs in peripheral blood and lymph nodes and the level of anti-HBsAg in two kinds of pre-mixed plans were compared.

The experiment included Plan A group (mixing the GM-CSF, IFN-α, and HBV vaccine right just before the immunization), and Plan B group (mixing the GM-CSF, IFN-α, and HBV vaccine and stored for 12 hs at 4° C. before the immunization). Each group were immunized twice for days 0 and 14, DCs in peripheral blood and lymph nodes were tested on days 1, 2 and 3 after immunizations, and anti-HBsAg level was detected on day 21. The results showed that ratio of CD11b$^+$CD11c$^+$DCs from the peripheral blood was significantly higher in both Plan A and B groups compared with that of PBS control (P<0.01). However, the Plan B group was higher than that of Plan A group (FIG. 3A). Plan A did not significantly increase the proportion of CD11b$^+$CD11c$^+$DCs in local lymph nodes, but the Plan B significantly increased the proportion of CD11b$^+$CD11c$^+$ DCs in local lymph nodes (FIG. 3B). In addition, Induciton of anti-HBsAg antibodies by the Plan A group was less than that the Plan B group (2136±165.2 mIU/mL v.s 3094±126.6 mIU/mL, P<0.01, FIG. 3C). These results demonstrate that a mix processing of each components of GM-CSF, IFN-α, and vaccine is more favorably to store for at least 12 hs at 4° C. before immunization.

1.3 Mice DTH Response after Immunization

Figure 4:
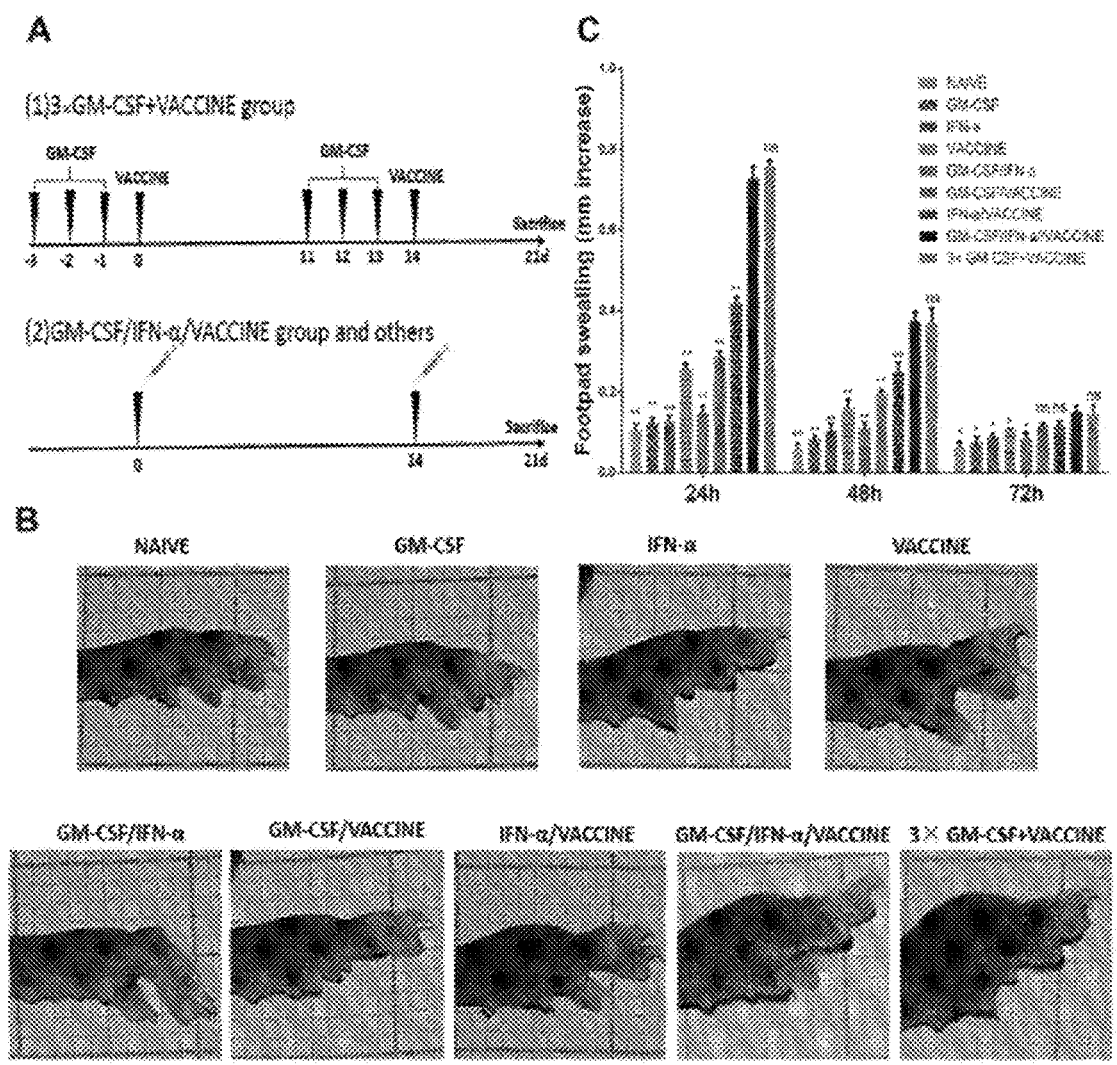
FIG. 4 is a set of graphs and images showing DTH results of wild-type mice immunized with different immunotherapeutic pharmaceutical compositions according to certain embodiments of the invention.

The cellular immunity plays an important role in the treatment of chronic hepatitis B since level of cellular immunity is positively correlated with the ability to clear the hepatitis B virus. DTH test is the most convenient and direct assessment of the cellular immunity. Based on the immunization strategy indicated as in FIG. 4A, HBsAg was injected into the mouse footpad to test the DTH response of the wild-type mice immunized with different regimens listed in the Table 3. The results showed that VACCINE alone, IFN-α/VACCINE, GM-CSF/VACCINE, 3×GM-CSF+VACCINE, IFN-α/GM-CSF/VACCINE could all induce DTH responses (FIG. 4B). As a statistical analysis comparing the different regimens, (FIG. 4C). The DTH response was achieved the strongest at 24 h in the animals with the 3×GM-CSF/VACCINE or the IFN-α/GM-CSF/VACCINE, which were significantly higher than other groups (P<0.01). However, there was no significant difference between the 3×GM-CSF/VACCINE and the IFN-α/GM-CSF/VACCINE immunizations (P>0.05), suggesting the two regimens can induce a similar level of cellular immunity. Considering a single formulation of IFN-α/GM-CSF/VACCINE with its easy to use, IFN-α/GM-CSF/VACCINE regimen has advantage to use over the 3-day pretreatment with GM-CSF before the vaccine (3×GM-CSF/VACCINE).

1.4 The Effect of IFN-α/GM-CSF/VACCINE on the Humoral Immunity

The production of protective antibodies is considered as a gold standard for assessing vaccine efficacy.

We tested the titer of anti-HBsAg antibodies (HBsAb) after each regimens immunizations. The result showed that the naïve mice, immunizations of GM-CSF, IFN-α, and IFN-α/GM-CSF did not induce HBsAb. VACCINE, GM-CSF/VACCINE, IFN-α/GM-CSF/VACCINE, and 3×GM-CSF/VACCINE induced various levels of HBsAb. The level of HBsAb in IFN-α/GM-CSF/VACCINE group (2749±238.9 IU/L) was slightly lower than that in 3×GM-CSF/VACCINE group (3016±196.2 IU/L), but not significant statistical difference (P>0.05). The level of HBsAb from these two groups was significantly increased compared with the VACCINE group (918.4±43.28 IU/L), GM-CSF/VACCINE group (1665±45.94 IU/L) and IFN-α/VACCINE group (1902±76.93 IU/L, FIG. 2A). In addition, the data also showed that GM-CS/VACCINE group and IFN-α/VACCINE group can produce higher HBsAb than VACCINE group (P<0.01). The result demonstrates that both groups of 3×GM-CSF+VACCINE and IFN-α/GM-CSF/VACCINE can induce higher level of protective HBsAbs.

Figure 5:
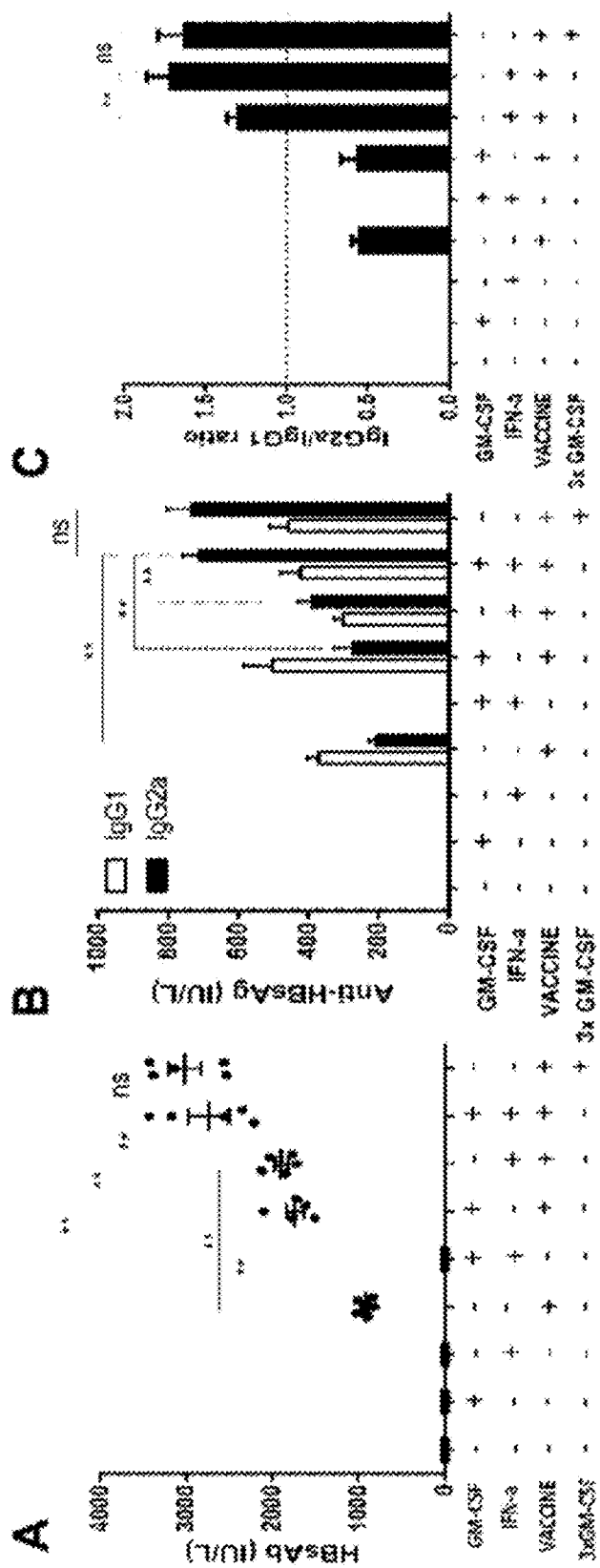
FIG. 5 is a set of graphs showing the concentration of HBsAg-specific HBsAb, IgG1, IgG2a produced by wild type mice according to certain embodiments of the invention.

The ratio of IgG2a/IgG1 can be used to evaluate host immune responses toward Th1 or Th2 polarization. As depicted in FIGS. 5B and 5C, significant higher ratio of IgG2a:IgG1 was associated with the IFN-α/GM-CSF/VACCINE group and 3×GM-CSF+VACCINE group compared with other immune groups (P<0.05), indicating that the IFN-α/GM-CSF/VACCINE and the 3×GM-CSF+VACCINE are the regimens to promote more Th1 type of response.

1.5 The Effect of IFN-α/GM-CSF/VACCINE on the Cellular Immunity

In the previous results of HBsAg-specific DTH and IgG1/IgG2a, we found that the IFN-α/GM-CSF/VACCINE group and the 3×GM-CSF/VACCINE group can all promote cellular immunity efficiently, while the important of cellular immunity is to clear of virus infection.

Figure 6:
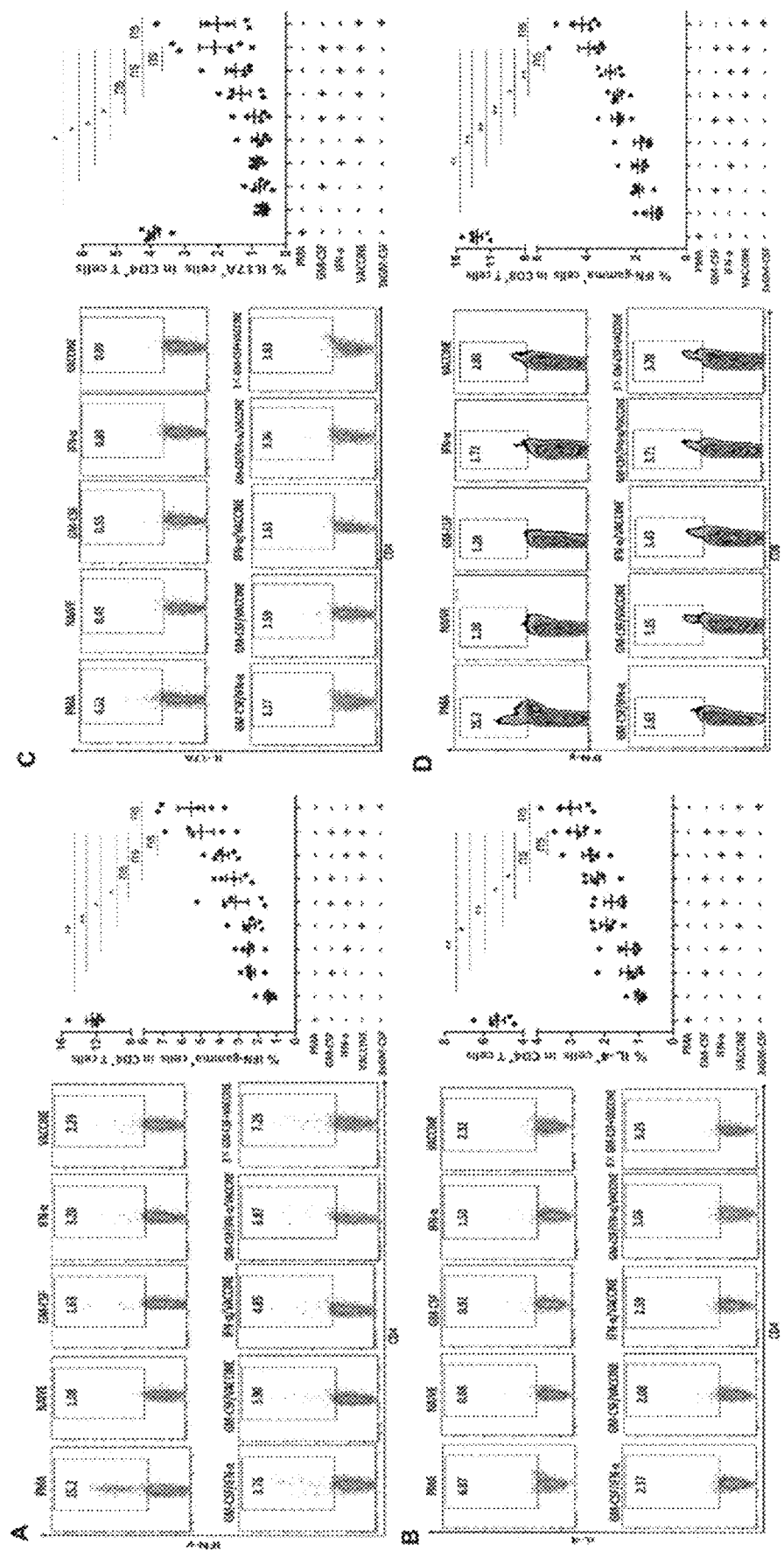
FIG. 6 is a set of graphs showing the results of the cytokine secretion of T lymphocytes from wild-type mice immunized with different immunotherapeutic pharmaceutical compositions according to certain embodiments of the invention: Seven days after the second immunization, the splenocytes were taken, stimulated with HBsAg (10 μg/L) for 18 h, and finally blocked by BFA for 6 hrs. Flow cytometry was used to detect CD4+T cells secreting IFN-γ (FIG. 3A), IL4 (FIG. 3B), IL17A (FIG. 3C) and CD8+T cells secreting IFN-γ(D). ns (P>0.05) showed no statistical difference, *(P<0.05) showed statistical difference, **(P<0.01) showed significant statistical difference.

The level of HBsAg-specific cellular immunity was further examined in different regimens. The results showed that the level of inductions of IFN-γ, IL-4, and IL-17 (FIG. 6C) of CD4+ T cells and IFN-γ of CD8+ T cells (FIG. 6D) was significant higher in the IFN-α/GM-CSF/VACCINE group and 3×GM-CSF+VACCINE over other groups (P>0.05). No significant differences were seen between the IFN-α/GM-CSF/VACCINE group and 3×GM-CSF+VACCINE group, indicating that both regimens can induce T cells to produce the similar level of cytokines.

1.6 T Cell Proliferation after Immunization

T lymphocyte proliferation is an important part of the cellular immune response. The specific level of T cell proliferation reflects the immunity against a particular antigen. In this study, CFSE-labeling method was used to test the T cell proliferation to HBsAg.

Figure 7:
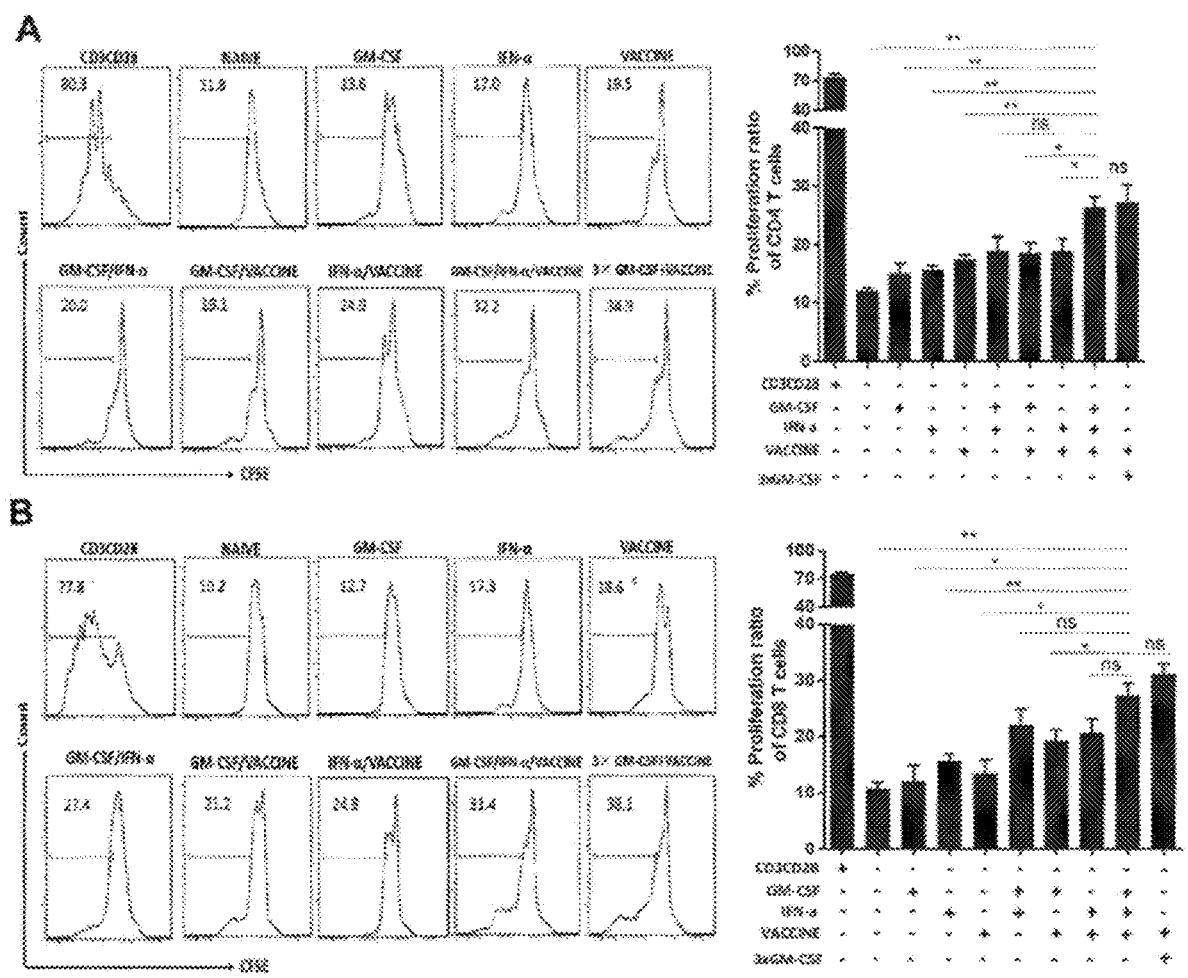
FIG. 7 is a set of graphs showing the proliferation of T lymphocytes from wild-type mice immunized with different immunotherapeutic pharmaceutical compositions according to certain embodiments of the invention: Seven days after the second immunization, the splenocytes were stained with 1 μM CFSE and stimulated with HBsAg (10 μg/mL) for 72 hrs. Flow cytometry was used to detect the proliferation of CD4+T cells (FIG. 4A) and CD8+T cells (FIG. 4B). ns (P>0.05) showed no statistical difference, *(P<0.05) showed statistical difference, **(P<0.01) showed significant statistical difference.

The data shows that the level of induction of CD4+ T cell proliferation in the IFN-α/GM-CSF/VACCINE group was no difference compared to the 3×GM-CSF+VACCINE (P>0.05; FIG. 7A), but was significant higher than other groups (P<0.01). For the CD8+ T lymphocyte proliferation level, the IFN-α/GM-CSF/VACCINE group was significant higher than that in GM-CSF/VACCINE group, GM-CSF group and VACCINE group (P<0.05), but not difference with 3×GM-CSF+VACCINE, IFN-α/GM-CSF, and IFN-α/VACCINE (P>0.05; FIG. 7B). From this, IFN-α/GM-CSF/VACCINE can also significantly promote the T lymphocyte proliferation at the similar level as 3×GM-CSF+VACCINE induced.

1.7 In Vitro CTL Assay

Figure 8:
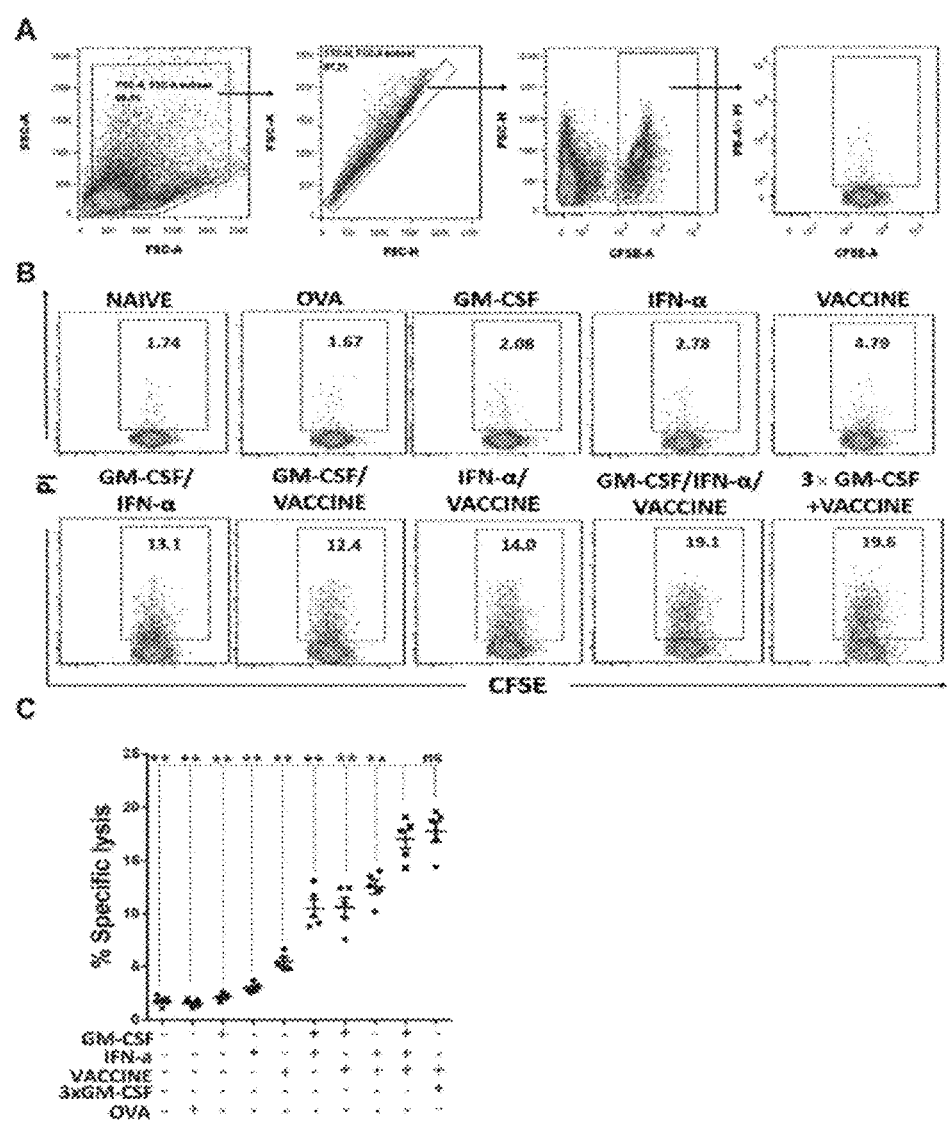
FIG. 8 is a set of graphs showing CTL in vitro results of immunized wild-type mice with different immunotherapeutic pharmaceutical compositions according to certain embodiment of the invention: After immunization, the splenocytes were isolated and cultured for 3 days with HBV CTL polypeptide S$_{208-215}$ (10 μg/mL) as non-related antigen cells. OVA CTL peptide OVA$_{257-264}$ (10 μg/mL) was used as no-related antigen cells. The wild type mouse spleen cells were incubated with HBV CTL peptide (10 μg/mL) for 1 hr at 37° C. and after collection stained with CFSE as target cells. Effector cells: target cells=20:1 were mixed and cultured for 6 hours, stained with PI 15 min, CTL cell killing of target cells detected by flow cytometry.

The CD8+ cytolitic cell (CTL) is the key factor for the evaluating function of any therapeutic vaccine. As for the HBV persistent infection, HBV antigen-specific CTL is considered as the major force to eliminate HBV from its infected cells. In this study, we examined the cytotoxicity of CD8+ T cells from different groups using an in vitro CTL assay. The results shown that induced levels of CTL by the IFN-α/GM-CSF/VACCINE and 3×GM-CSF+VACCINE were 20% higher than other methods (P<0.01, FIG. 8).

1.8 Effects on Antigen Presenting Cells (APC)

In the previous experiments, we found that IFN-α/GM-CSF/VACCINE regimen can better stimulate humoral and cellular immune responses, suggesting that it could activate antigen presenting cells (APC) efficiently. APCs, especially dendritic cells (DCs), play a definitive role linking between innate and adaptive immune responses. Thus, we hypothesized that IFN-α/GM-CSF/VACCINE regimen could greatly influence function of DCs.

Figure 9:
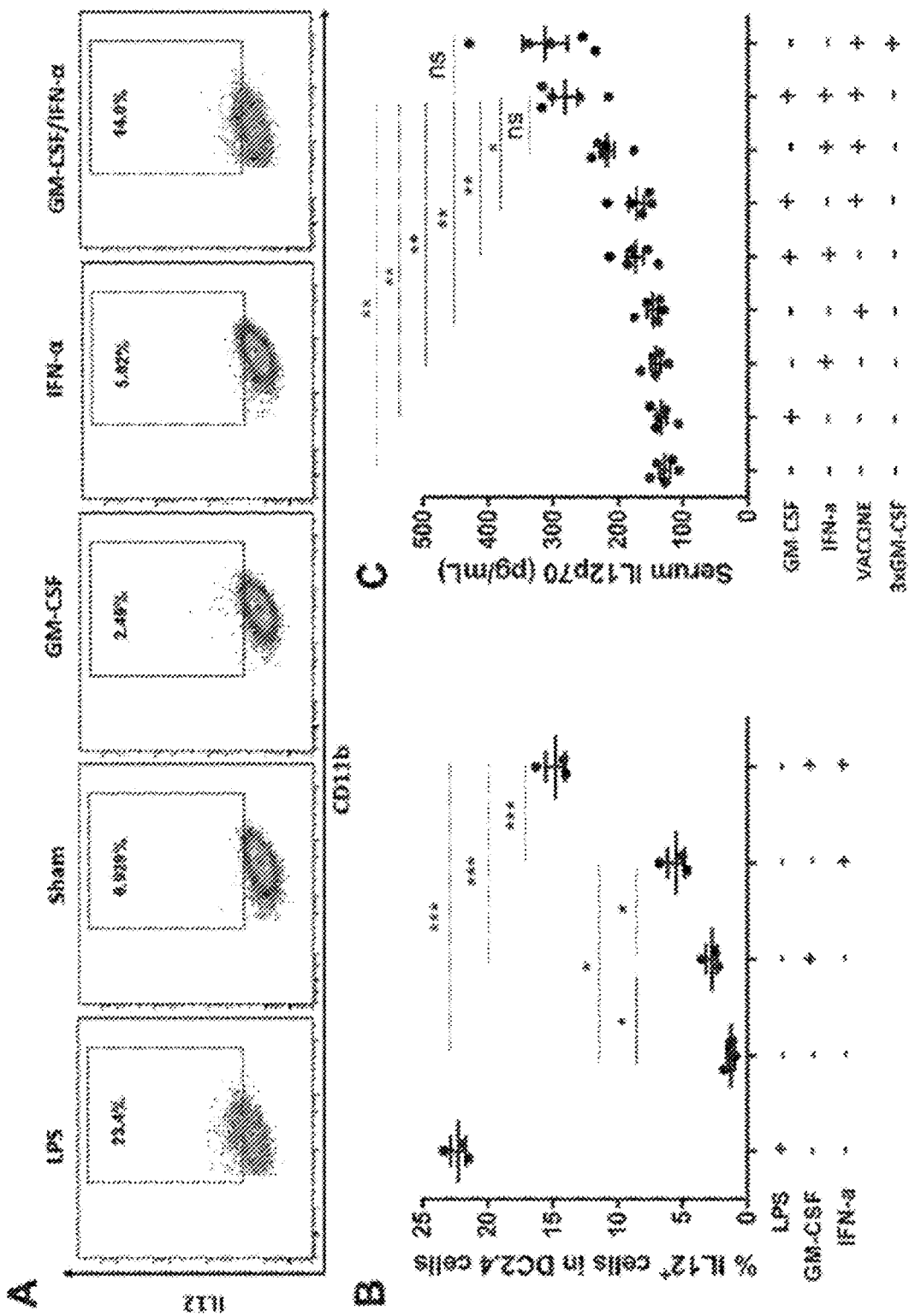
FIG. 9 is a set of graphs showing the effect of different immunotherapeutic pharmaceutical compositions on DC2.4 cells secreting IL-12 and the concentration of serum IL-12 in wild-type mice in a better example of the invention: DC2.4 cells were treated with GM-CSF (1 μg/mL), IFN-α (20 IU/mL) and LPS respectively for 72 hrs.

First, we tested murine bone marrow-derived DC2.4 cells in vitro and found that the treatment of IFN-α/GM-CSF could significantly improve the DCs to secrete IL-12 compared to that of IFN-α or GM-CSF alone (FIG. 9B). In vivo experiments, we also found that concentration of serum IL-12p70 was significantly increased on 21 days after IFN-α/GM-CSF/VACCINE or 3×GM-CSF+VACCINE immunizations in mice over other groups (FIG. 9C).

Figure 10:
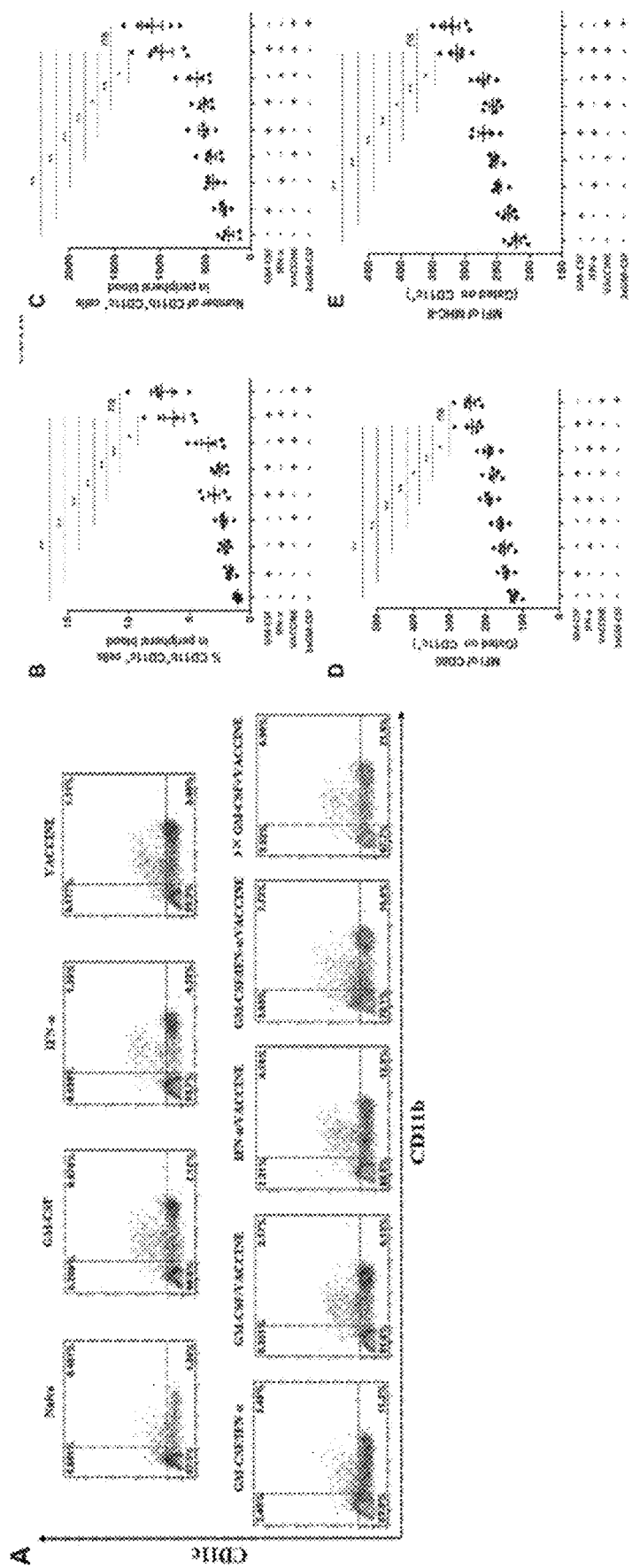
FIG. 10 is a set of graphs showing the effect of different immunotherapeutic pharmaceutical compositions on the number and function of blood DC cells in wild-type mice in a better example of the invention.

Furthermore, we observed that the frequency and absolute numbers of CD11b+CD11c+ DC, expressions of CD80 and MHC-II induced by the IFN-α/GM-CSF/VACCINE regimen were significantly higher than in the IFN-α/GM-CSF, IFN-α/VACCINE, GM-CSF/VACCINE, or VACCINE group (P<0.05). These induced changes were at highest in the IFN-α/GM-CSF/VACCINE and 3×GM-CSF+VACCINE groups, although no significant difference between these two regimens (FIG. 10).

1.9 In Vivo Mononuclear Cells Assay

Figure 11:
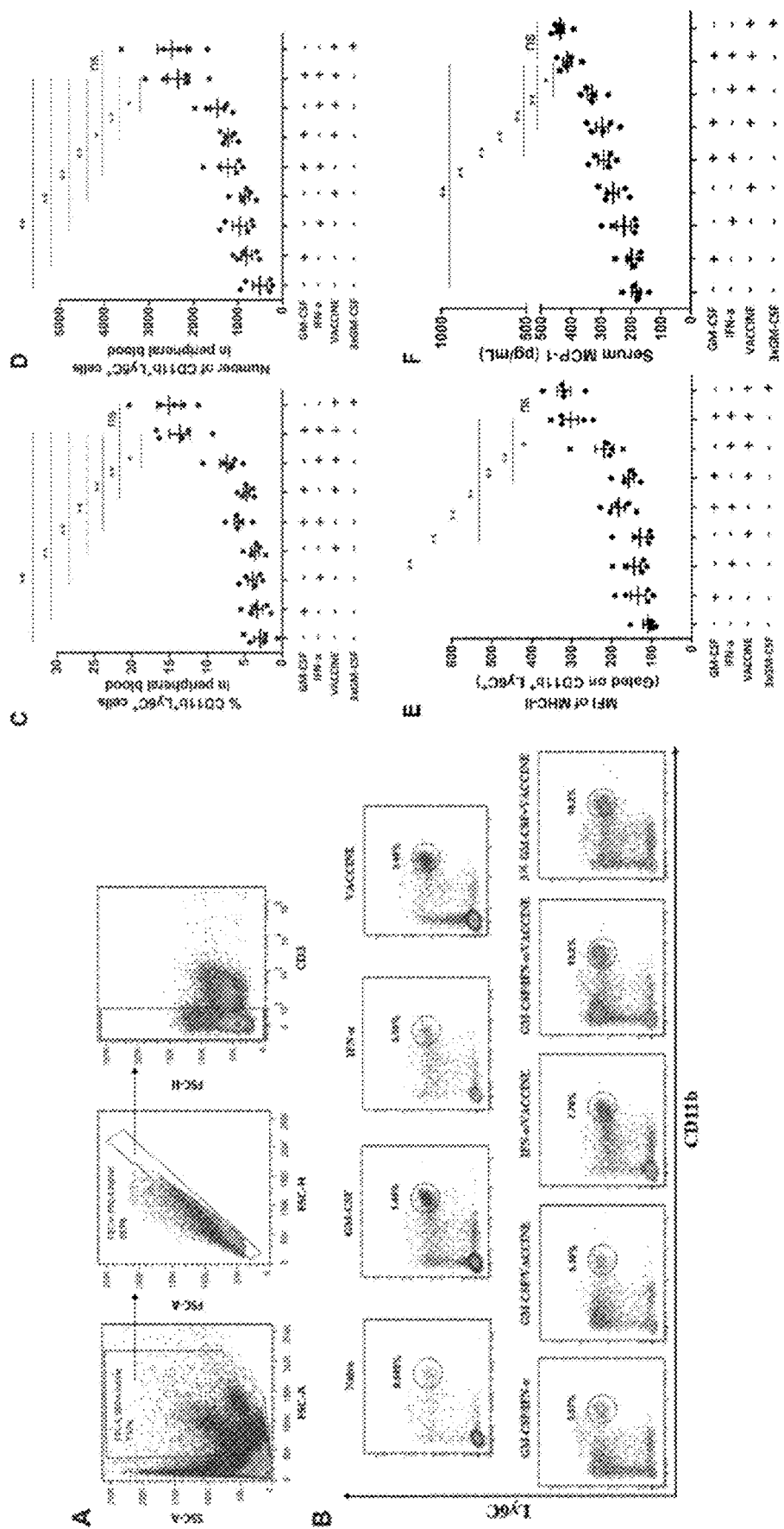
FIG. 11 is a set of graphs showing the effect of different immunotherapeutic pharmaceutical compositions on the number and function of blood monocytes in wild type mice in a better example of the invention.

As showed in previous results, we demonstrated that the IFN-α/GM-CSF/VACCINE and 3×GM-CSF+VACCINE regimens could significantly increase the number and function of DCs. At normally, DCs are in a constant number. The sources of increasing number of CD11b+CD11c+ DCs could be due to the conversion of monocytes since they can continue to differentiate into macrophages or dendritic cells under the different cytokines. To seek if monocytes were converted into DC by the IFN-α/GM-CSF/VACCINE regimen in vivo, animals were immunized with various regimens and their monocytes were analyzed before and after the immunization. The data show that the number of CD11b+Ly6C+ monocytes from peripheral blood treated by the IFN-α/GM-CSF/VACCINE or the 3×GM-CSF+VACCINE regimens was significantly higher than that of other regimens (P<0.05). Concurrently, the expressions of CD80 and MHC-II on these monocytes were also increased significantly (FIG. 11). In addition, the concentrations of MCP-1 in the serum from the IFN-α/GM-CSF/VACCINE and 3×GM-CSF+VACCINE regimens were significantly higher than those of other immunized groups on day 21 after their immunization detected by ELISA assay (P<0.05).

1.10 Summary

The above experimental data indicate that the IFN-α/GM-CSF/VACCINE could achieve same immune effects as from the 3×GM-CSF+VACCINE does. This IFN-α/GM-CSF/VACCINE at an optimal dose and formulation becomes easier to use regimen, therefore presents a great advantage over cumbersome protocol from the 3×GM-CSF+VACCINE. The optimized IFN-α/GM-CSF/VACCINE can completely replace 3×GM-CSF+VACCINE in clinical applications, to achieve a clinical benefit.

Example 2

IFN-α/GM-CSF/VACCINE Breaks Immune Tolerance in rAAV-1.3HBV Mice

In Example 1, both IFN-α/GM-CSF/VACCINE and 3×GM-CSF+VACCINE can stimulate humoral and cellular responses in wild-type mice to significantly increase HBV-specific CTL activity of CD8+ T cells. To test if they could break immune tolerance in chronic hepatitis B to clear the HBV. we adopted a new animal model. In this model, we infected with a recombinant adeno-associated virus (AAV) carrying 1.3 copies of the HBV genome (AAV8-1.3HBV) to established a HBV induce immuno tolerance and used this model to evaluate an efficacy of the optimized IFN-α/GM-CSF/VACCINE regimen.

2.1 Establishment and Verification of rAAV-1.3HBV Mouse Model

Figure 12:
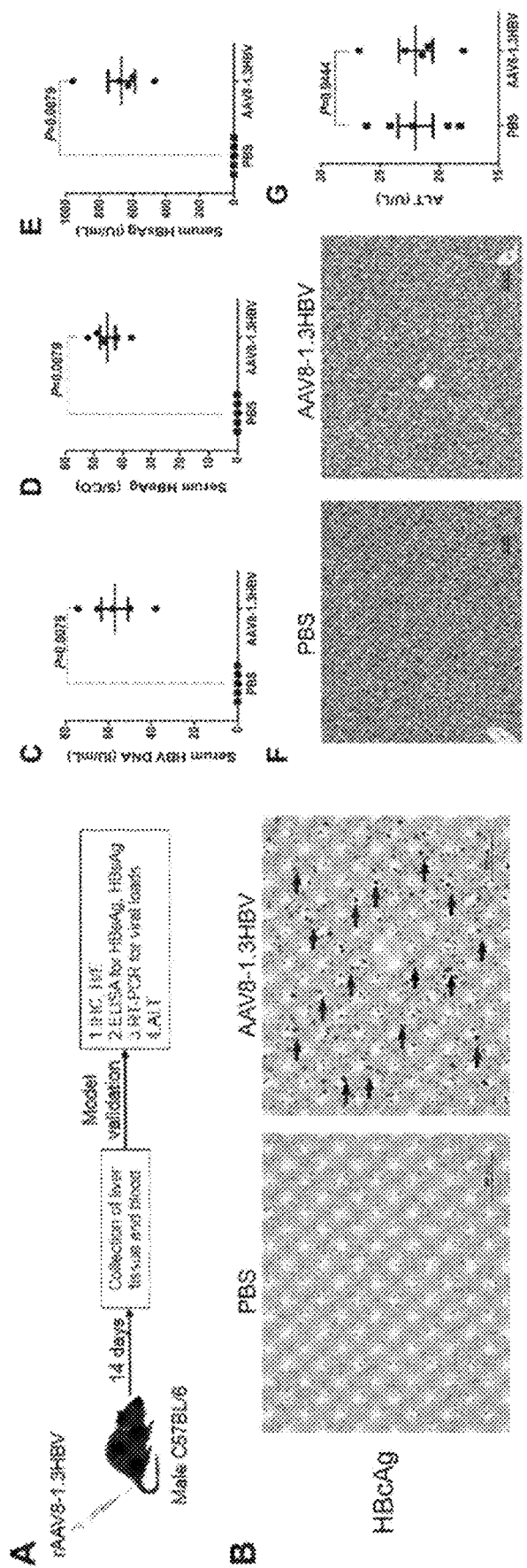
FIG. 12 is a set of graphs, diagrams and images showing validation of rAAV8-1.3HBV mouse model validation in a better example of the invention.

In order to verify whether the rAAV-1.3HBV recombinant virus can infect male C57BL/6 mice, a model was established by injecting with $1\times10^6$ pfu/ml of virus through the tail vein. The data showed that the serum samples contained HBeAg as a positive (S/CO>1), the HBsAg at 667.9±80.39 IU/mL and the HBV-DNA at 205.6±28.92 copies/mL after the infection, which were significant higher than the PBS control group (P<0.0001, FIG. 12). The levels of alanine aminotransferase (ALT) from infected mice were at 20.81±1.72 U/L, which was not statistically different from the PBS control group (22.01±1.47 U/L). Immunohistochemistry (IHC) results showed that HBcAg positivities were observed only in hepatocytes that were infected with the rAAV-1.3HBV virus, HBcAg-positive cells were not found in the heart and kidneys. The results of H&E showed that the sizes of liver cells infected with rAAV-1.3HBV became larger, but no obvious changes were found in the myocardial cells and renal cells.

2.2 rAAV-1.3HBV Mouse Model Monitoring

Figure 13:
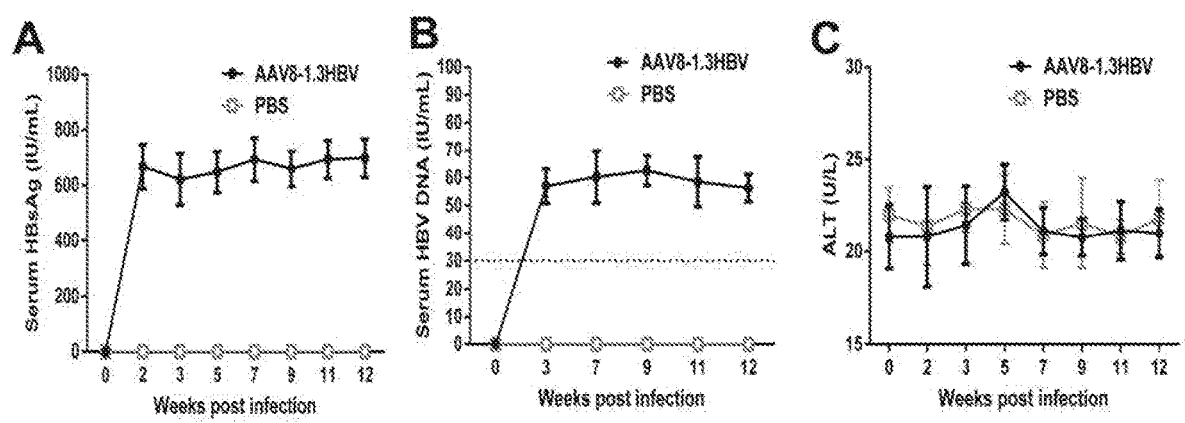
FIG. 13 is a set of graphs showing the monitoring of the rAAV8-1.3HBV mouse model in a better example of the invention: C57B/L6 mice were infected with rAAV-1.3 HBV virus.

To assess the viral persistency, we continuously monitored mice over 12 weeks after the virus infection (wpi). The expression of HBsAg and viral DNA was remained stable without significant reduction over 12 wpi (FIG. 13). In addition, serum levels of ALT over this period of time were no significant difference from the PBS group, indicating rAAV-1.3HBV can a persistent infection in male C57BL/6 mice.

2.3 GM-CSF/IFN-α/VACCINE Treatment of Hepatitis B Mice

Figure 14:
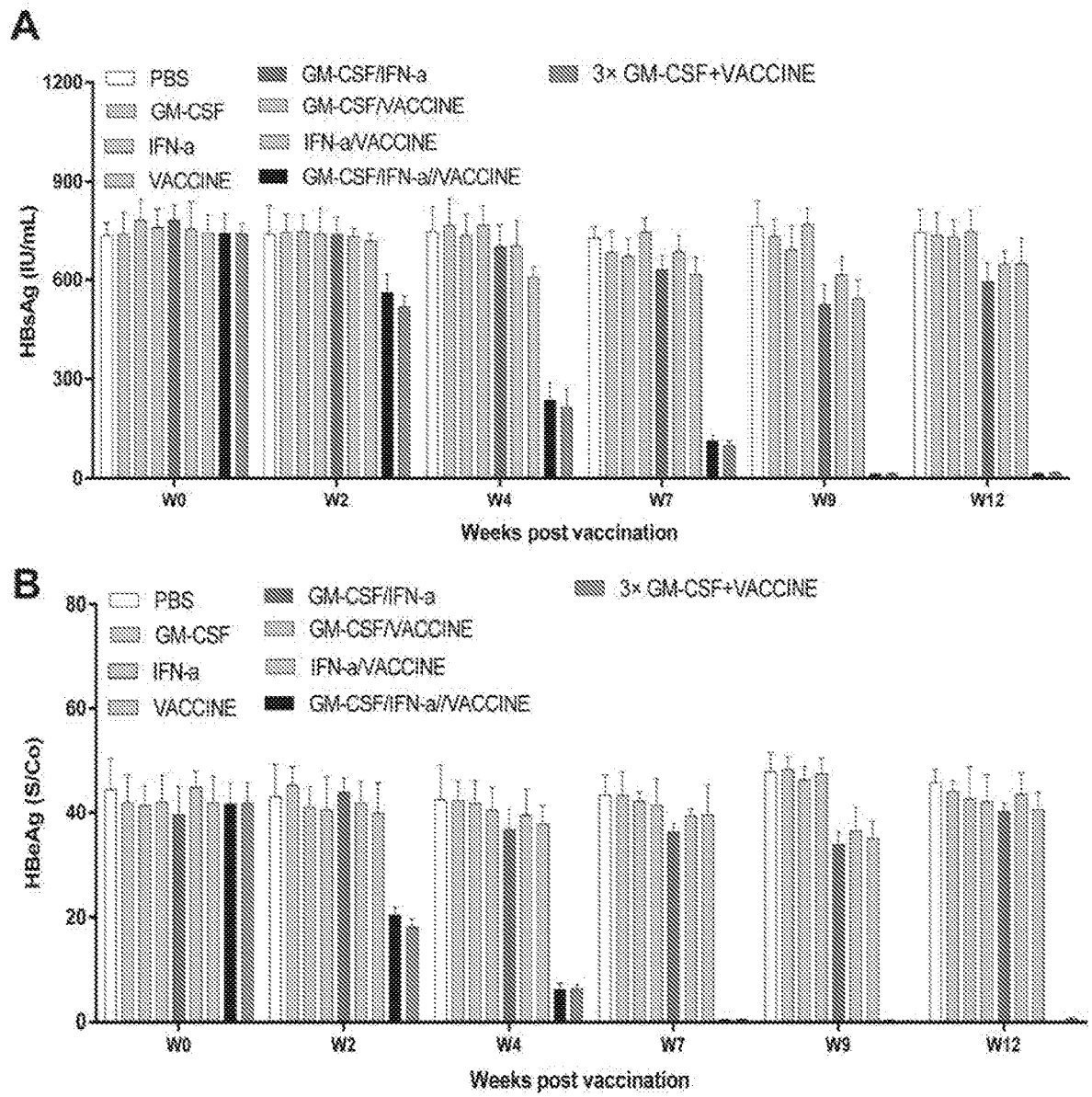
FIG. 14 is a set of graphs showing the change on serum levels of HBsAg and HBeAg in the animals immunized with immunotherapeutic pharmaceutical compositions in hepatitis B model mice in a better example of the invention: Immunization was started on the 21st day after infection with the virus and immunized every two weeks. Serum HBsAg and HBeAg concentrations were measured before each immunization.

To test if the optimized regimen could clear hepatitis B virus infections from these mice, we applied the optimized immunization strategy for the GM-CSF/IFN-α/VACCINE to treatment rAAV8-1.3HBV infected mice. Infected mice were immunized with various regimens for four times with biweekly intervals, and serum samples were collected to analyze at each indicated time points. We observed that serum level of HBsAg of GM-CSF/IFN-α/VACCINE or 3×GM-CSF+VACCINE group were reduced significant compared with other groups and diminished after the 4 immunizations at 9 wpi (P<0.01, FIG. 14). Serum level of HBeAg were significantly reduced and cleared at 7wpi in both GM-CSF/IFN-α/VACCINE and 3×GM-CSF+VACCINE treated groups compared with other groups (P<0.01). Both immunizations of GM-CSF/IFN-α/VACCINE and 3×GM-CSF+VACCINE achieve a similar and robust therapeutic benefits in those immune tolerance animals, suggesting that both regimens could induce robust anti-HBV immune responses that lead to clear the persistent HBV infection in the animal model.

2.4 Effect of GM-CSF/IFN-α/VACCINE on DCs from the HBV Infected Mice

Since DCs play a definitive role in promoting cell-specific cellular immunity, we found that GM-CSF/IFN-α/VACCINE can significantly promote the production of CD11b$^+$CD11c$^+$DCs in wild-type mice. Therefore, we also sought to examine the effect of GM-CSF/IFN-α/VACCINE on DC production in the rAAV8-1.3HBV infected mice.

Figure 15:
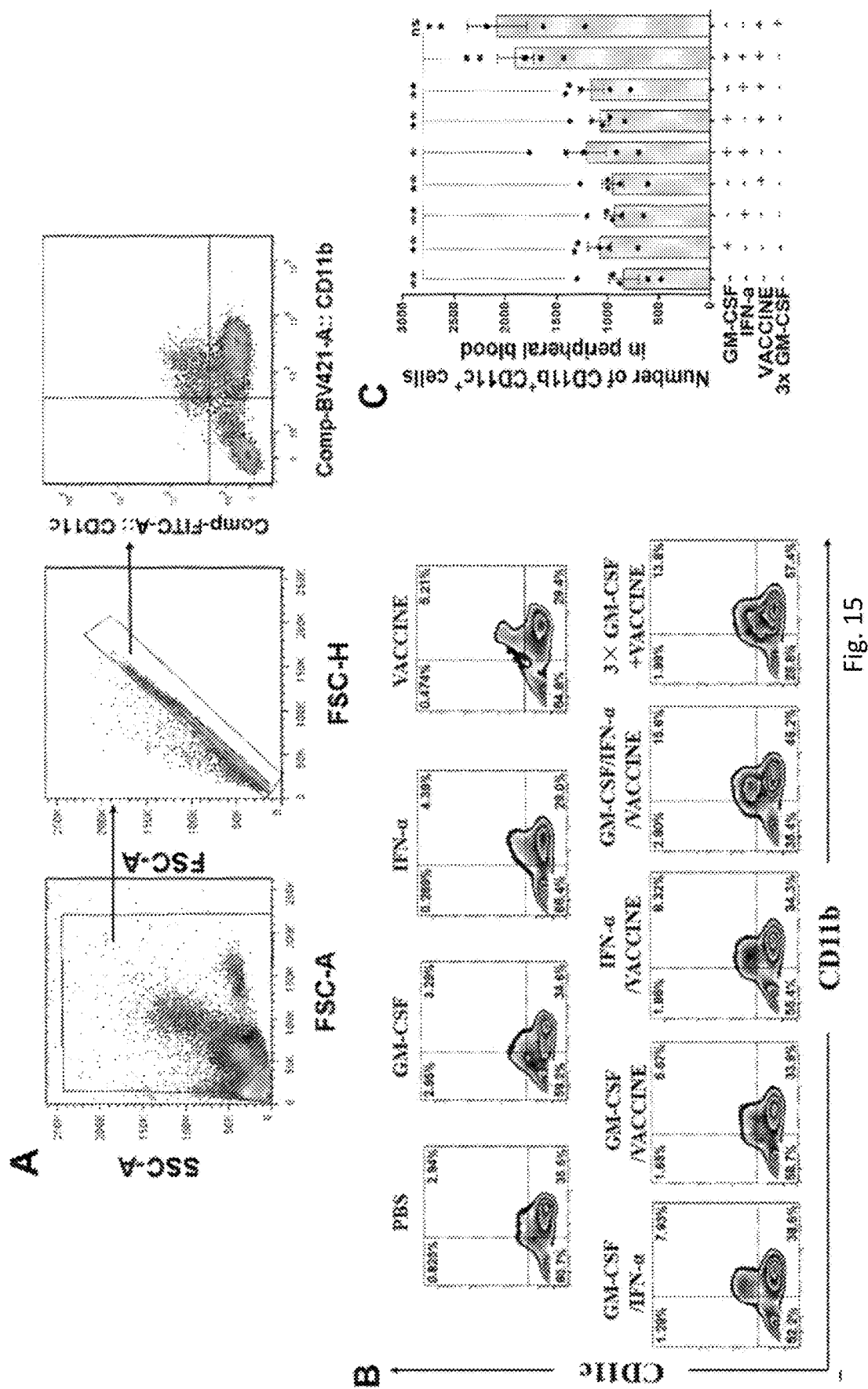
FIG. 15 is a set of graphs showing the effect of immunotherapeutic pharmaceutical compositions treatments on $CD11b^+CD11c^+$ dendritic cells in the blood of rAAV8-1.3 hepatitis B mice in a better example of the invention: On the third day after Hepatitis B mouse model immunized, the venous blood of mice was taken and the level of $CD11b^+CD11c^+$ DC in blood was measured.
Figure 15:
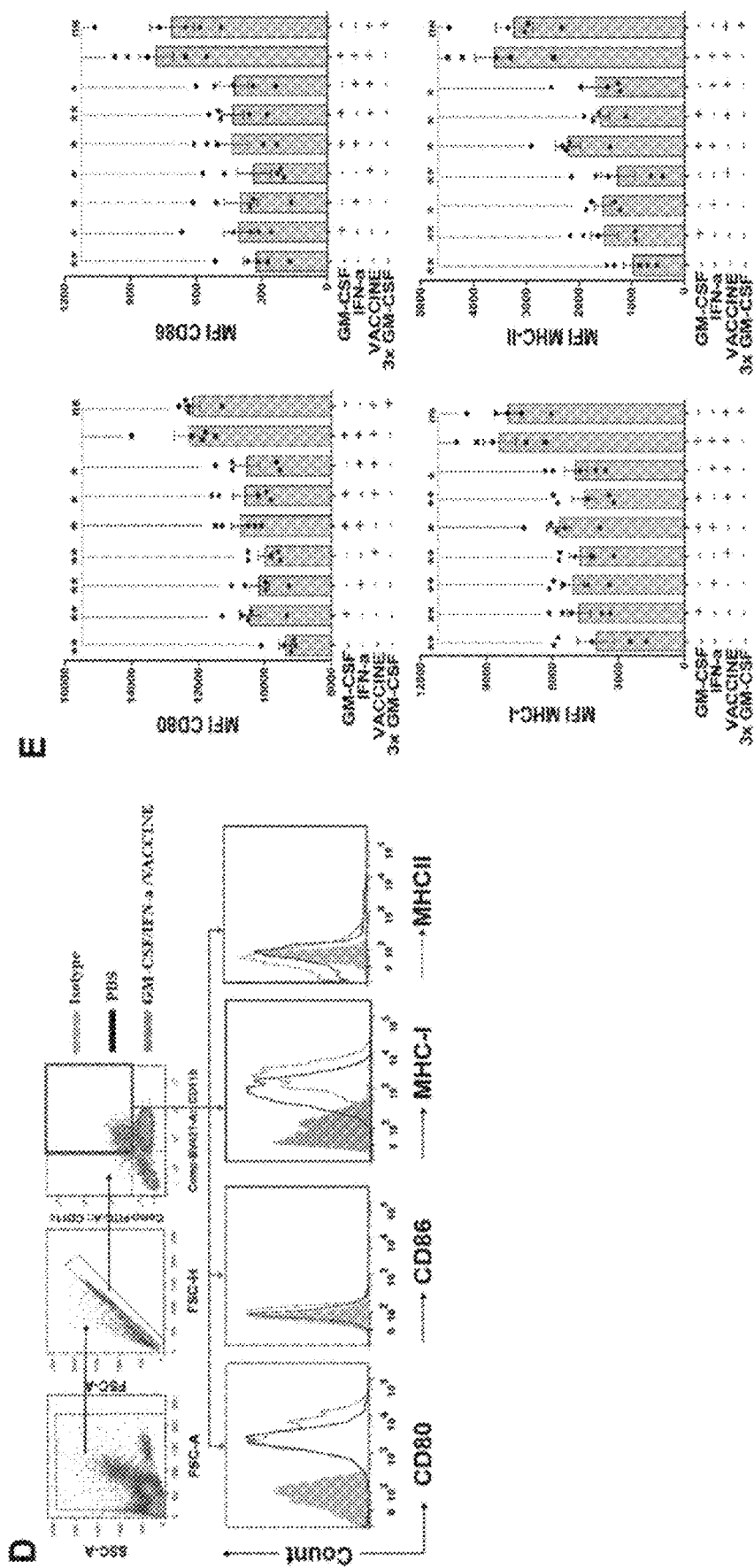

Both regimens of the GM-CSF/IFN-α/VACCINE and 3×GM-CSF+VACCINE could significantly promote the production of CD11b$^+$CD11c$^+$DCs which was significant higher than other immunized groups (P<0.01, FIG. 15A-C). In addition, the GM-CSF/IFN-α/VACCINE and 3×GM-CSF+VACCINE regimens induced expressions of CD86, MHC-I and MHC-II on CD11b$^+$CD11c$^+$DCs significantly higher than other immunized groups (P<0.05, FIG. 15D-E). The treatments of GM-CSF/IFN-α/VACCINE can not only induce CD11b$^+$CD11c$^+$DCs production, also enhance the ability of DCs to process antigens in these rAAV8-1.3HBV infected mice.

2.5 Effect of GM-CSF/IFN-α/VACCINE on Monocytes in the HBV Infected Mice

It was found that GM-CSF/IFN-α/VACCINE significantly promoted CD11b$^+$Ly6C$^+$ monocytes in wild-type mice. Therefore, we attempted to verify that the effect of the GM-CSF/IFN-α/VACCINE regimen on monocytes in the HBV infected mice.

Figure 16:
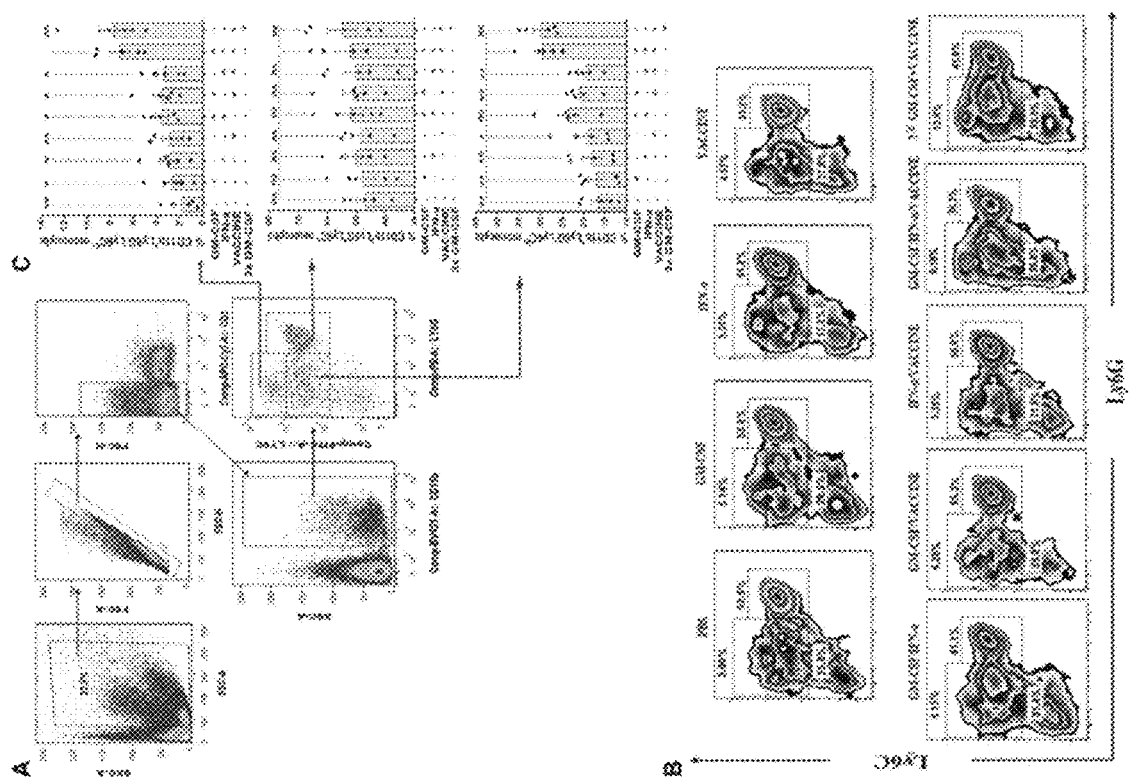
FIG. 16 is a set of graphs showing the effect of immunotherapeutic pharmaceutical composition treatments on monocytes in the blood of rAAV8-1.3 hepatitis B mice: On the third day after Hepatitis B mouse model immunized, the venous blood of mice was taken and the level of monocytes in the blood was measured.
Figure 16:
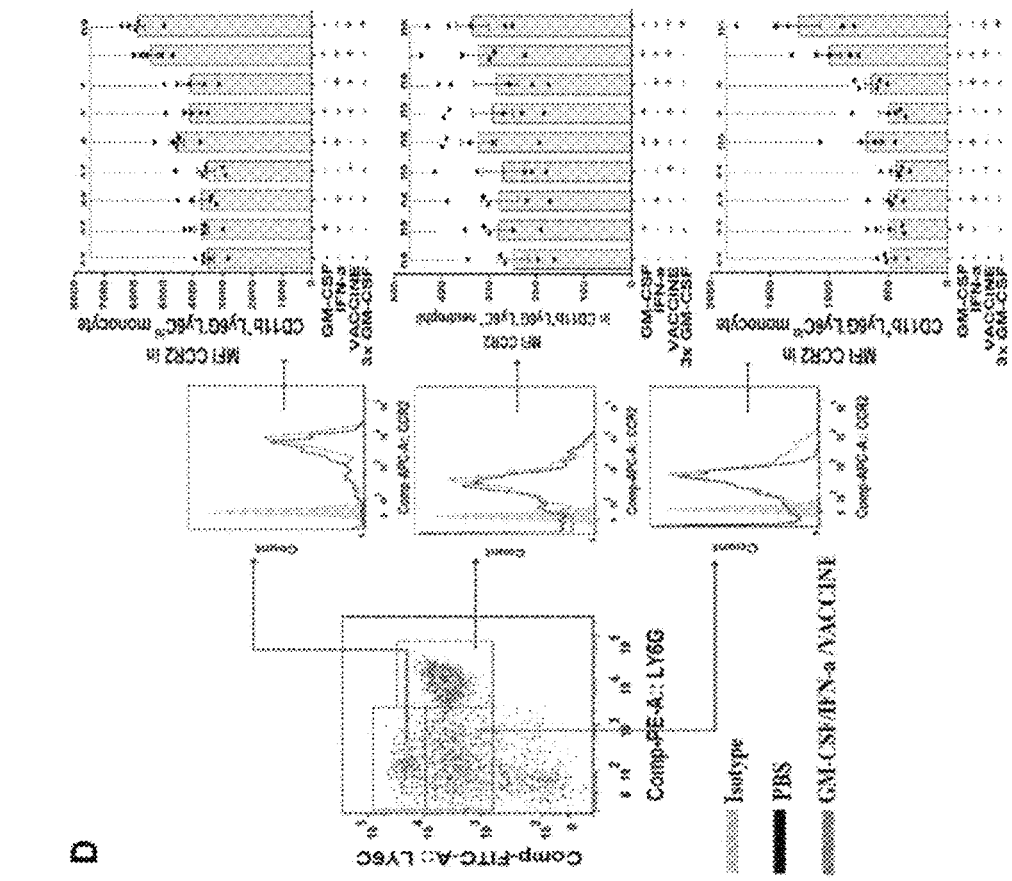

Both GM-CSF/IFN-α/VACCINE and 3×GM-CSF+VACCINE regimens induced a superior level of the monocytes of CD11b$^+$Ly6G$^-$Ly6C$^{hi}$ and CD11b$^+$Ly6G$^-$Ly6C$^{lo}$ (P>0.05) compared with the GM-CSF, IFN-α, GM-CSF/IFN-α, GM-CSF/VACCINE and IFN-α/VACCINE group (P<0.05), and that of PBS and VACCINE groups (P<0.01, FIG. 16). The numbers of granulocytes in GM-CSF/IFN-α/VACCINE group and 3×GM-CSF+VACCINE group were significantly higher than other groups (P<0.01). The CD11b$^+$Ly6G$^-$Ly6C$^{hi}$ monocytes have been demonstrated to induce a high level of CCR2$^{hi}$ on these monocytes, an indicator for inflammation; whereas CD11b$^+$Ly6G$^-$Ly6C$^{hi}$ monocytes were associated the CCR2$^{lo}$ circulating monocytes.

2.6 Effect of GM-CSF/IFN-α on Human Monocytes to DCs Differentiation

As we demonstrated that GM-CSF/IFN-α/VACCINE can promote the production of DCs and monocytes, we would test if there was a direct correlation between DCs and monocytes. For this, CD14$^+$ monocytes from human PBMCs were isolated by anti-CD14 conjugated magnetic beads and stimulated with GM-CSF, IFN-α, GM-CSF/IFN-α and LPS, respectively. The results showed that both GM-CSF and IFN-α could promote CD14$^+$ monocytes to CD11c$^+$DC conversion, effects of the combination was more rigorously than either one of them. Combination of GM-CSF and IFN-α could also facilitate expressions of CD80, CD86, HLA-A2 and HLA-DR on DCs than either one of them. Thus, combination of GM-CSF/IFN-α can not only promote the monocyte to DC conversion, but more importantly, facilitate the DC maturation and functionality.

2.7 Effect of GM-CSF/IFN-α/VACCINE on Cellular Immunity in HBV Infected Mice

DTH represents antigen specific cellular responses. Both GM-CSF/IFN-α/VACCINE and 3×GM-CSF+VACCINE regimens can significantly elicit DTH responses in HBV infected mice, and the most reaction at 24 h (P<0.01) over other groups (FIG. 17A).

Figure 17:
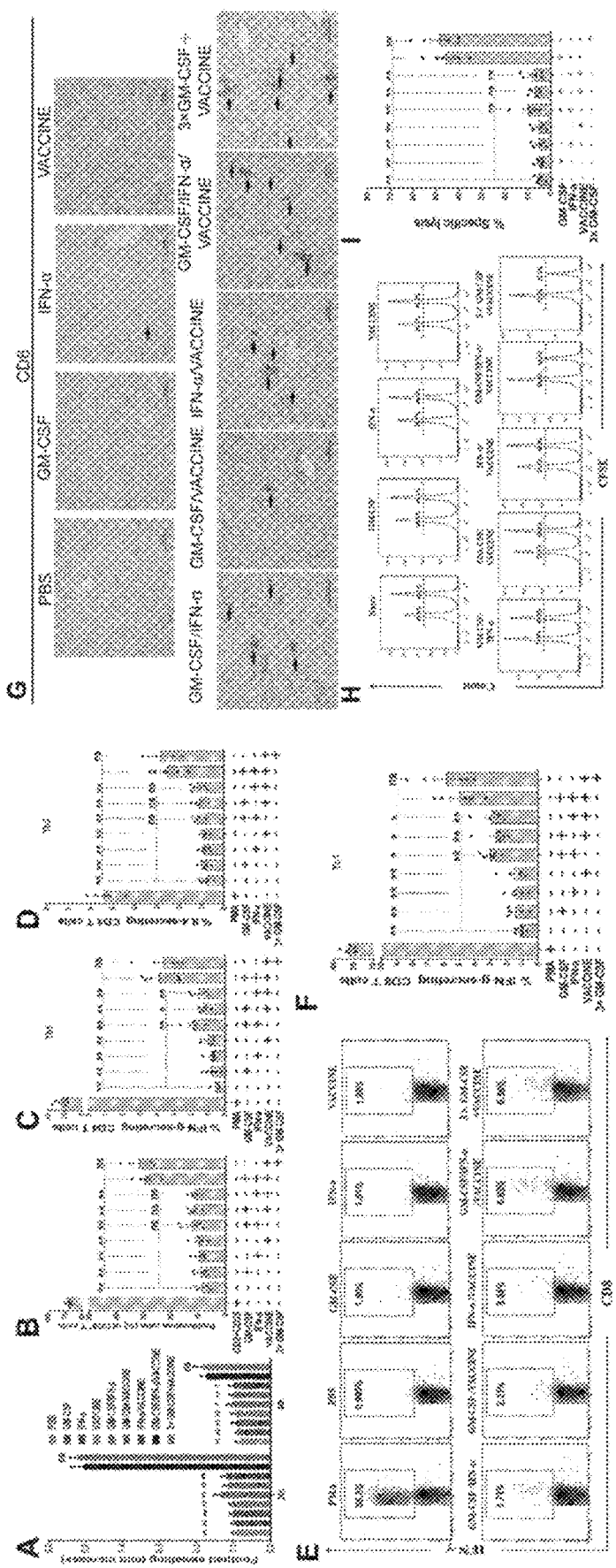
FIG. 17 is a set of graphs and images showing that immunotherapeutic pharmaceutical composition treatments improve cellular immunity of rAAV8-1.3HBV hepatitis B mice.

T cell proliferation were significantly enhanced by the GM-CSF/IFN-α/VACCINE group and 3×GM-CSF+VACCINE group compared with other groups in HBV infected mice (P<0.01, FIG. 17B).

Both GM-CSF/IFN-α/VACCINE and 3×GM-CSF+VACCINE groups were able to promote IFN-γ producing-CD4$^+$ T cells (Th1) and CD8$^+$ T cells (Tc1) at higher level (P<0.01), IL-4 producing CD4$^+$ T cells over other groups in HBV infected mice (P<0.01, FIG. 17C&F).

By immunohistochemistry analysis of CD8 cells in liver tissues, we could observed that both the GM-CSF/IFN-α/VACCINE and 3×GM-CSF+VACCINE groups induced more CD8+ T cell infiltrations into liver than other groups in HBV infected mice (FIG. 17G).

In the in vivo CTL assay, both the GM-CSF/IFN-α/VACCINE and 3×GM-CSF+VACCINE groups could induce significant higher level of CTL (at 45%) against HBV compared with other groups in HBV infected mice (FIG. 17HI).

Figure 18:
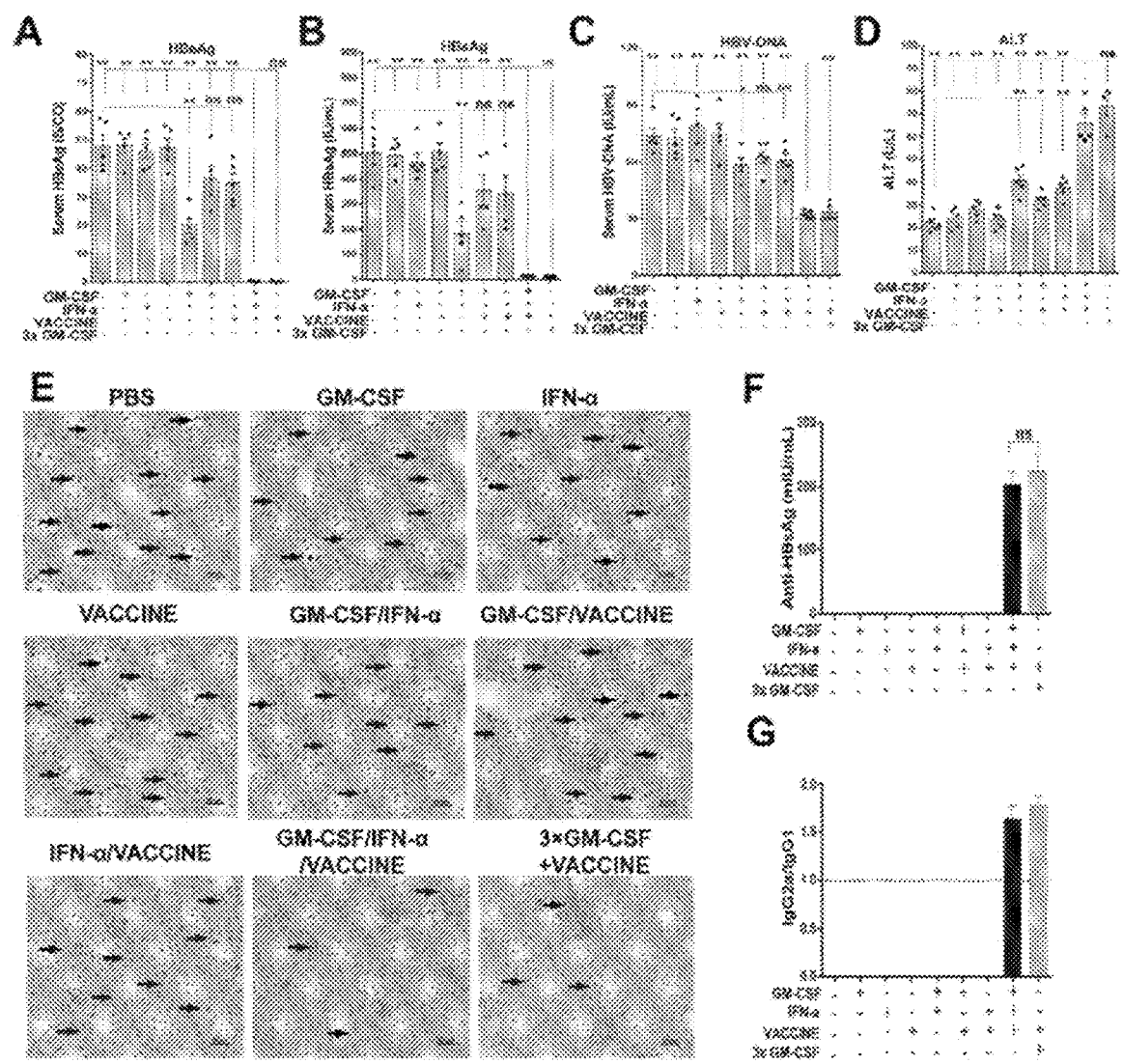
FIG. 18 is a set of graphs and images showing that immunotherapeutic pharmaceutical compositions treatments improve humoral immunity of rAAV8-1.3HBV hepatitis B mice: Fourteen days after the 4th immunization, the peripheral blood was taken and serum was separated.

2.8 Effect of GM-CSF/IFN-α/VACCINE Regimen on Humoral Response in HBVHBV Infected Mice To examine effect of GM-CSF/IFN-α/VACCINE regimen on humoral immune response in the rAAV8-1.3HBV infected mice, animals were immunized with various regimens 4 times with biweekly intervals, tested for their anti-HBV antibody responses, and analyzed for concentrations of HBeAg (FIG. 18A) and HBsAg (FIG. 18B) and HBV-DNA (FIG. 18C). We observed that both levels of HBeAg and HBsAg were cleared, serum level of HBV-DNA was below the limit of detection and the serum ALT was increased about 3-fold after 4 immunizations with either GM-CSF/IFN-α/VACCINE or 3×GM-CSF+VACCINE compared with other groups. It was also noted that the combination of GM-CSF and IFN-α induced higher level of ALT, suggesting that such combination induces higher inflammation in liver. Analysis of liver immunohistochemistry was revealed that the HBcAg-positive cells in the liver were significantly reduced after GM-CSF/IFN-α/VACCINE and 3×GM-CSF+VACCINE immunizations (FIG. 18E). In addition, anti-HBsAg antibodies could be only induced in the GM-CSF/IFN-α/VACCINE and 3×GM-CSF+VACCINE immunized groups. Further examination of the antibody subtypes showed that IgG2a:IgG1>1, suggesting that a strong cellular immune responses was induced.

2.9 Effect of Blockage of Ly6C$^{hi}$CCR2$^{hi}$ Monocytes on GM-CSF/IFN-α/VACCINE Regimen Since the GM-CSF/IFN-α/VACCINE could promote CD11b$^+$Ly6G$^-$Ly6C$^{hi}$CCR2$^{hi}$ monocytes in peripheral blood in the rAAV8-1.3HBV infected animals, and strong associated with cellular and humoral responses, which ultimately HBV clearance. To test if the Ly6C$^{hi}$CCR2$^{hi}$ monocyte is particularly important in the context of immune activation and break immune tolerance, we used CCR2 inhibitor to block CCR2 function in the same animal model.

Figure 19:
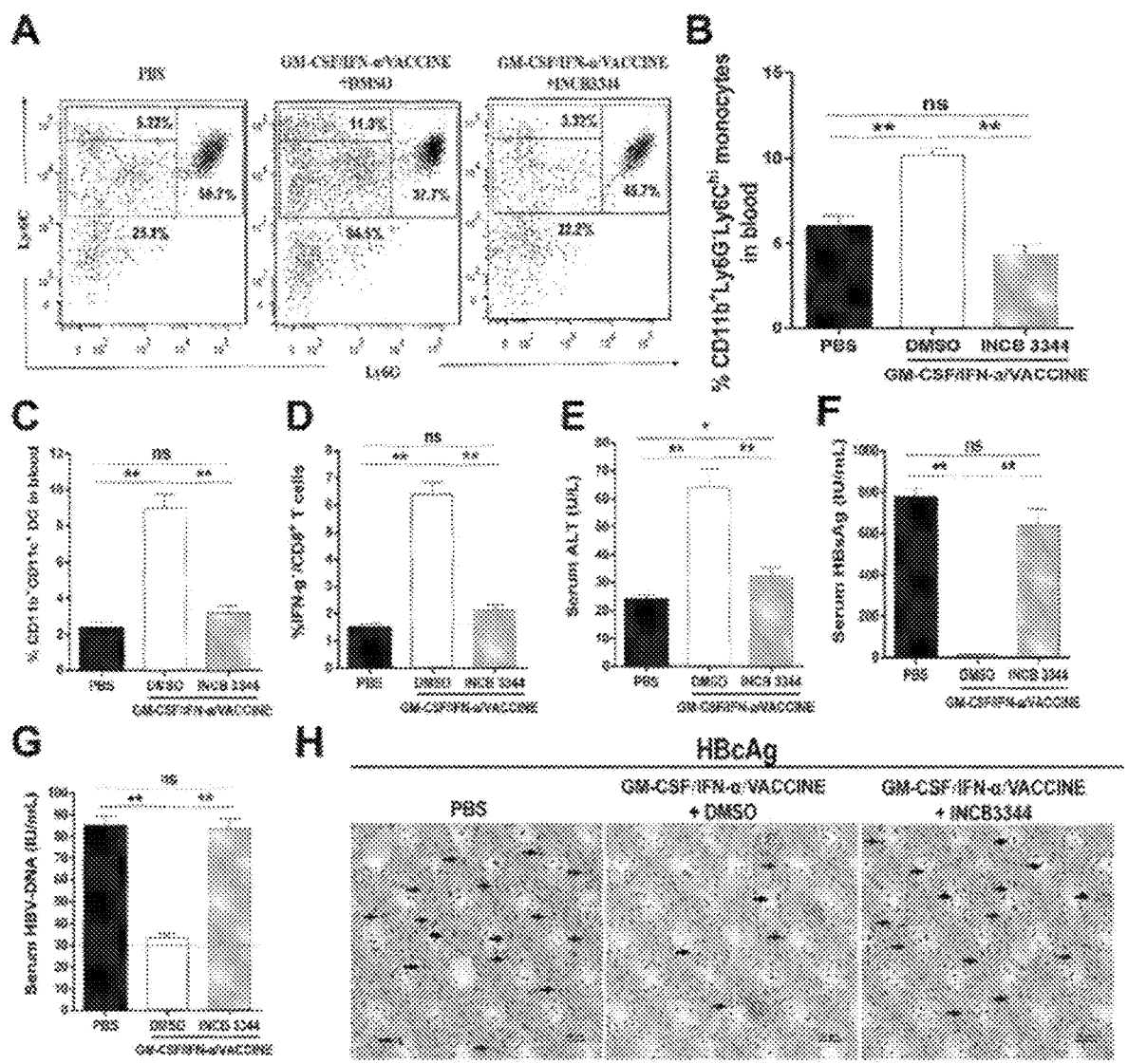
FIG. 19 is a set of graphs and images showing the effect of blocking CCR2 on the efficacy of immunotherapeutic pharmaceutical compositions treatments: The CCR2 blocker INCB 3344 was injected at a dose of 30 μg/kg 3 times, 1 h before injection of GM-CSF/IFN-α/VACCINE, 24 h and 48 h after injection, respectively. Flow cytometry and statistical analysis of CD11 b$^+$Ly6C$^{hi}$CCR2$^{hi}$ monocytes in peripheral blood after 3 days (FIG. 19A) and (FIG. 19B) respectively.

We first found that the ratio of CD11b$^+$Ly6C$^{hi}$CCR2$^{hi}$ monocytes and CD11b$^+$CD11c$^+$DC from peripheral blood were significantly lower in the in vivo blocked with CCR2 inhibitor (INCB3344) than those of non-blocked group (FIG. 19A-B). Meanwhile, IFN-γ-producing CD8+ T cells and serum ALT were significantly lower in animals treated with CCR2 inhibitor than those un-blocked groups. Furthermore, we also found that serum level of HBsAg and HBV-DNA was slightly changed in animals treated with CCR2 inhibitor or PBS control group. Finally, the results of liver immunohistochemistry exhibited that the clearance of HBcAg-positive cells were severely inhibited in animals treated with CCR2 inhibitor compared with non-blocked groups.

Example 3

To demonstrate that effects of GM-CSF/IFNα-2b/VACCINE on the antitumor immune responses, we selected one of the prostate cancer epitopic peptide sequence (PAP, sequence is: CMSAMTNLAALFPPEG, as shown in SEQ ID NO.1) to be the vaccine antigen. The selected prostate cancer epitope peptide (PAP) was first conjugated with Keyhole Limpet Hemocyanin (KLH) or albumin from bovine serum (BSA). After its purification, the conjugated antigen at 50 μg was mixed with 10 μg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 μg of the conjugated antigen was formulated in aluminum adjuvant and immunized subcutaneously BALB/c mice twice a week for 2 times. The prostate cancer epitope peptide (PAP) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 μg conjugated antigen for delayed type hypersensitivity (DTH) assay. We observed that the levels of antibodies (FIG. 20A) and DTH (FIG. 20B) against prostate tumor antigen was significantly higher in the animals immunized with GM-CSF/IFNα-2b/conjugated PAP vaccine than the control group.

Example 4

To demonstrate that effects of GM-CSF/IFNα-2b/VACCINE on the antitumor immune responses, we selected one of the breast cancer epitopic peptide (WT1, sequence: CYTWNQMNLSLGEQQYSV, as shown in SEQ ID NO. 2) to be the vaccine antigen. The selected breast cancer epitope peptide (WT1) was first conjugated with Keyhole Limpet Hemocyanin (KLH) or albumin from bovine serum (BSA). After its purification, the conjugated antigen at 50 μg was mixed with 10 μg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 μg of the conjugated antigen was formulated in aluminum adjuvant and immunized subcutaneously BALB/c mice twice a week for 2 times. The breast cancer epitopic peptide (WT1) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 μg conjugated antigen for delayed type hypersensitivity (DTH) assay. We observed that the levels of antibodies (FIG. 21A) and DTH (FIG. 21B) against the breast cancer antigen was significantly higher in the animals immunized with GM-CSF/IFNα-2b/conjugated WT1 vaccine than the control group.

Example 5

To demonstrate that effects of GM-CSF/IFNα-2b/VACCINE on the antitumor immune responses, we selected one of the colorectal cancer epitopic peptide (CEA, the sequence is: YLSGADLNLC, as shown in SEQ ID NO.3) to be the vaccine antigen. The selected breast cancer epitopic peptide (CEA) was first conjugated with Keyhole Limpet Hemocyanin (KLH) or albumin from bovine serum (BSA). After its purification, the conjugated antigen at 50 μg was mixed with 10 μg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 μg of the conjugated antigen was formulated in aluminum adjuvant and immunized subcutaneously BALB/c mice twice a week for 2 times. The colorectal cancer epitopic peptide (CEA) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 μg conjugated antigen for delayed type hypersensitivity (DTH) assay. We observed that the levels of antibodies (FIG. 22A) and DTH (FIG. 22B) against the colorectal cancer antigen was significantly higher in the animals immunized with GM-CSF/IFNα-2b/conjugated CEA vaccine than the control group.

Example 6

To demonstrate that effects of GM-CSF/IFNα-2b/VACCINE on the antitumor immune responses, we selected one of the colorectal cancer epitopic peptide (E6, the sequence is: DKKQRFHNIRGRWTGRCMSCCRSSRTRRETQLC, as shown in SEQ ID NO. 4) to be the vaccine antigen. The selected colorectal cancer epitopic peptide (E6) was first conjugated with Keyhole Limpet Hemocyanin (KLH) or albumin from bovine serum (BSA). After its purification, the conjugated antigen at 50 µg was mixed with 10 µg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 µg of the conjugated antigen was formulated in aluminum adjuvant and immunized subcutaneously BALB/c mice twice a week for 2 times. The colorectal cancer epitopic peptide (E6) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 µg conjugated antigen for delayed type hypersensitivity (DTH) assay. We observed that the levels of antibodies (FIG. 23A) and DTH (FIG. 23B) against the colorectal cancer antigen was significantly higher in the animals immunized with GM-CSF/IFNα-2b/conjugated E6 vaccine than the control group.

Example 7

To demonstrate that effects of GM-CSF/IFNα-2b/VACCINE on the antitumor immune responses, we selected one of the hepatocellular carcinoma (HCC) epitopic peptide (Trp, the sequence of which is: CRPGWRAACNQKIL, as shown in SEQ ID NO. 5) to be the vaccine antigen. The selected hepatocellular carcinoma epitopic peptide (Trp) was first conjugated with Keyhole Limpet Hemocyanin (KLH) or albumin from bovine serum (BSA). After its purification, the conjugated antigen at 50 µg was mixed with 10 µg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 µg of the conjugated antigen was formulated in aluminum adjuvant and immunized subcutaneously BALB/c mice twice a week for 2 times. The hepatocellular carcinoma epitope peptide (Trp) was conjugated with BSA and formulated as described above GM-CSF/IFNα-2b and alum adjuvant. The modality of immunizations was as above mentioned schedule and route. Two weeks after the immunizations, the serum samples of mice were taken for ELISA assay to examine the level of antigen specific humoral response, footpad injected with 10 µg conjugated antigen for delayed type hypersensitivity (DTH) assay. We observed that the levels of antibodies (FIG. 24A) and DTH (FIG. 24B) against the HCC cancer antigen was significantly higher in the animals immunized with GM-CSF/IFNα-2b/conjugated HCC vaccine than the control group.

Example 8

To demonstrate that effects of GM-CSF/IFNα-2b/VACCINE on the antitumor immune responses, we selected one of the multiple myeloma epitopic peptide (MAGE-A3, sequence: KVAELVHFLFLWGPRALVC, as shown in SEQ ID NO. 6) to be the vaccine antigen. The selected the multiple myeloma epitopic peptide (MAGE-A3) was first conjugated with Keyhole Limpet Hemocyanin (KLH) or albumin from bovine serum (BSA). After its purification, the conjugated antigen at 50 µg was mixed with 10 µg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 µg of the conjugated antigen was formulated in aluminum adjuvant and immunized subcutaneously BALB/c mice twice a week for 2 times. The multiple myeloma epitopic peptide (MAGE-A3) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 µg conjugated antigen for delayed type hypersensitivity (DTH) assay. We observed that the levels of antibodies (FIG. 25A) and DTH (FIG. 25B) against the multiple myeloma cancer antigen was significantly higher in the animals immunized with GM-CSF/IFNα-2b/conjugated MAGE-A3 vaccine than the control group.

Example 9

To demonstrate that effects of GM-CSF/IFNα-2b/VACCINE on the antitumor immune responses, we selected one of the Renal cell carcinoma antigen epitope peptide (hTERT, sequence: EARPALLTSRLRFIPKC, shown as SEQ ID NO: 7) to be the vaccine antigen.

The selected colorectal cancer epitopic peptide (hTERT) was first conjugated with Keyhole Limpet Hemocyanin (KLH) or albumin from bovine serum (BSA). After its purification, the conjugated antigen at 50 µg was mixed with 10 µg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 µg of the conjugated antigen was formulated in aluminum adjuvant and immunized subcutaneously BALB/c mice twice a week for 2 times. The colorectal cancer epitope peptide (hTERT) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 µg conjugated antigen for delayed type hypersensitivity (DTH) assay. We observed that the levels of antibodies (FIG. 26A) and DTH (FIG. 26B) against the Renal cell carcinoma cancer antigen was significantly higher in the animals immunized with GM-CSF/IFNα-2b/conjugated hTERT vaccine than the control group.

Example 10

To demonstrate that effects of GM-CSF/IFNα-2b/VACCINE on the antitumor immune responses, we selected one of the type A *Streptococcus* antigen epitope peptide (J8, the sequence of which is: QAEDKVKQSREAKKQVEKALKQLEDKVQC, as shown in SEQ ID NO. 8) to be the vaccine antigen. The selected type A *Streptococcus* antigen epitope peptide (J8) was first conjugated with Keyhole Limpet Hemocyanin (KLH) or albumin from bovine serum (BSA). After its purification, the conjugated antigen at 50 µg was mixed with 10 µg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 µg of the conjugated antigen was formulated in aluminum adjuvant and immunized subcutaneously BALB/c mice twice a week for 2 times. The type A *Streptococcus* antigen epitope peptide (J8) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 μg conjugated antigen for delayed type hypersensitivity (DTH) assay. We observed that the levels of antibodies (FIG. 27A) and DTH (FIG. 27B) against the type A *Streptococcus* antigen was significantly higher in the animals immunized with GM-CSF/IFNα-2b/conjugated J8 vaccine than the control group.

Example 11

To demonstrate that effects of GM-CSF/IFNα-2b/VACCINE on the antitumor immune responses, we selected one of the HIV epitope peptide (C4-V3, the sequence of which is: KQIINMWQEVGKAMYARPNCNTRKSIHIGPGRAFYTTGEIIC, as shown in SEQ ID NO. 9) to be the vaccine antigen. The selected HIV epitope peptide (C4-V3) was first conjugated with Keyhole Limpet Hemocyanin (KLH) or albumin from bovine serum (BSA). After its purification, the conjugated antigen at 50 μg was mixed with 10 μg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 μg of the conjugated antigen was formulated in aluminum adjuvant and immunized subcutaneously BALB/c mice twice a week for 2 times. The HIV epitope peptide (C4-V3) was conjugated with BSA and formulated as described above GM-CSF/IFNα-2b and alum adjuvant. The modality of immunizations was the same as above mentioned schedule and route. Two weeks after the immunizations, the serum samples of mice were taken for ELISA assay to examine the level of antigen specific humoral response, footpad injected with 10 μg conjugated antigen for delayed type hypersensitivity (DTH) assay. We observed that the levels of antibodies (FIG. 28A) and DTH (FIG. 28B) against the HIV antigen was significantly higher in the animals immunized with GM-CSF/IFNα-2b/conjugated C4-V3 vaccine than the control group.

Example 12

To demonstrate that effects of GM-CSF/IFNα-2b/VACCINE on the antitumor immune responses, we selected two additional HBV polypeptides (codon optimized PreS as shown in SEQ ID NO. 10, and its cDNA sequence as shown in SEQ ID NO. 11, and codon optimized PreS1 as shown in SEQ ID NO. 12) to be the vaccine antigen. The conjugated antigen at 50 μg was mixed with 10 μg GM-CSF and 10,000 IU IFNα-2b at 4° C., subsequently formulated with aluminum hydroxide adjuvant. The formulated vaccine was used to immunize BALB/c mice subcutaneously twice a week for 2 times. As a control group, the 50 μg of the conjugated antigen was formulated in aluminum adjuvant and immunized subcutaneously BALB/c mice twice a week for 2 times.

The 1 ug of PreS or 1 ug of PreS1, respectively, mixed with 10 μg GM-CSF and 10,000 IU IFNα-2b at 4° C., subsequently formulated with aluminum hydroxide adjuvant. Female Balb/c mice at 6-8 weeks old were immunized biweekly intervals for 3 times subcutaneously with GM-CSF/IFN-α/PreS or GM-CSF/IFN-α/PreS1, respectively. The control groups were immunized either with PreS, or with PreS1 alone. The level of humoral response was detected by ELISA before and after each immunization. The level of anti-PreS1 or PreS specific antibodies were significantly higher than that of controls as shown in FIG. 29.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. An immunotherapeutic pharmaceutical composition comprises at least an antigen and an immune enhancer, wherein the immune enhancer comprises at least a recombinant interferon and a granulocyte-macrophage colony-stimulating factor, wherein the ratio of the content of the recombinant interferon to the content of the recombinant granulocyte- macrophage colony-stimulating factor is (about $0.5\times10^4$ IU-about $5\times10^4$ IU) to (about 5 μg-about 50 μg), and the recombinant interferon is interferon alpha.

2. The immunotherapeutic pharmaceutical composition of claim 1, wherein the antigen comprises a recombinant protein antigen.

3. The immunotherapeutic pharmaceutical composition of claim 1, wherein the ratio of the content of the recombinant interferon to the content of the recombinant granulocyte-macrophage colony-stimulating factor is (about $0.5\times10^4$ IU-about $1.5\times10^4$ IU) to (about 5 μg- about 20 μg).

4. The immunotherapeutic pharmaceutical composition of claim 1, wherein the ratio of the content of the recombinant interferon to the content of the recombinant granulocyte-macrophage colony-stimulating factor is about $1\times10^4$ IU to about 10μg.

5. The immunotherapeutic pharmaceutical composition of claim 2, wherein the recombinant protein antigen is at least one of a viral antigen, a bacterial antigen, a fungal antigen, a parasite antigen, and a tumor antigen.

6. The immunotherapeutic pharmaceutical composition of claim 5, wherein the viral antigen is at least one of HBV antigens, herpesvirus antigens, HPV antigens, HIV antigens, Merkel cell virus antigens, influenza antigens and RSV antigens.

7. The immunotherapeutic pharmaceutical composition of claim 2, wherein the recombinant protein antigen is an inactivated vaccine antigen, an attenuated vaccine antigen or a subunit vaccine antigen.

8. The immunotherapeutic pharmaceutical composition of claim 2, wherein the recombinant protein antigen is a genetically engineered recombinant antigen.

9. The immunotherapeutic pharmaceutical composition of claim 1, wherein the immunotherapeutic pharmaceutical composition further comprises pharmaceutically or immunologically acceptable carriers or excipients.

10. A method for preparing the immunotherapeutic pharmaceutical composition of claim 1, wherein the method comprises the steps of:
mixing the antigen, the recombinant interferon, the granulocyte-macrophage colony-stimulating factor, and the pharmaceutically or immunologically acceptable carriers or excipients under aseptic conditions to produce the immunotherapeutic pharmaceutical composition.

11. A method of administration of immunotherapeutic pharmaceutical compositions, said method comprising administration of a safe and therapeutically effective amount of the immunotherapeutic pharmaceutical compositions of claim 5 to a subject in need thereof in order to 1) promoting monocytes production; 2) promoting expression of monocyte CCR2; 3) promoting differentiation of Ly6C$^{hi}$CCR2+ monocytes into DCs with phenotype CD11b$^+$ CD11c$_+$; 4) improving the cellular immunity and CM cytolytic functions of a subject; 5) promoting the humoral immunity of the subject and production of one or several protective antibodies.

12. The method of claim 11, wherein the method comprises inhibiting or treating one or more of viral infections, bacterial infections, fungal infections, parasitic infections, and tumors.

13. The method of claim 12, wherein the viral infections comprise one or more of human hepatitis virus infection, herpes virus infection, human papilloma virus infection, human immunodeficiency virus infection, Merkel cell virus infection, influenza virus infection and respiratory syncytium virus infection.

14. The method of claim 12, wherein the viral infection is chronic hepatitis B virus infection.

15. The method of claim 11, wherein the antigen is a hepatitis B surface antigen and the immunotherapeutic pharmaceutical composition can break down immune tolerance and eliminate infected hepatocytes, HBeAg and HBsAg, while generating anti-HBs Ab.

16. The method of claim 11, wherein the antigen is a tumor antigen and the immunotherapeutic pharmaceutical composition induces an anti-tumor immune response.

17. The method of claim 16, wherein the tumor antigen comprises at least one of a prostate cancer antigen polypeptide or epitopic peptide, a breast cancer antigen polypeptide or epitopic peptide, a colorectal cancer antigen polypeptide or epitopic peptide, a cervical cancer polypeptide or epitopic peptide, a liver cancer polypeptide or epitopic peptide, multiple myeloma polypeptide or epitopic peptide, and renal cell carcinoma polypeptide or epitopic peptide.

18. The method of claim 11, wherein the antigen is a streptococcal antigen and the immunotherapeutic pharmaceutical composition induces an antibacterial immune response.

19. The method of claim 18, wherein the streptococcal antigen is a modified Streptococcus Type A epitope peptide.

20. The method of claim 11, wherein the antigen is an HIV antigen and the immunotherapeutic pharmaceutical composition induces an anti-HIV immune response.

21. The method of claim 20, wherein the HIV antigen is an HIV epitope peptide.

22. The method of claim 11, wherein the antigen is a Merkel cell viral antigen and the immunotherapeutic pharmaceutical composition induces an anti-Merkel cell virus immune response.

23. The method of claim 22, wherein the Merkel cell viral antigen is a Merkel cell polypeptide.

24. The immunotherapeutic pharmaceutical composition of claim 1, wherein the antigen is a hepatitis B antigen, a hepatitis B virus (HBV) pre-surface (PreS) protein as shown in SEQ ID NO:10 or a HBV PreS1 protein as shown in SEQ ID NO:12 and the immunotherapeutic pharmaceutical composition can break down the immune tolerance and eliminate infected hepatocytes, hepatitis B e antigen (HBeAg) and hepatitis B s antigen (HBsAg), while generating anti-HBsAg antibodies (HBs Ab).

25. The immunotherapeutic pharmaceutical composition of claim 1, wherein the recombinant interferon is interferon alpha-2b.

\* \* \* \* \*